(12) United States Patent
Raychaudhuri et al.

(10) Patent No.: US 6,280,734 B1
(45) Date of Patent: Aug. 28, 2001

(54) SIMIAN-HUMAN HAV HAVING A CHIMERIC 2C PROTEIN

(75) Inventors: Gopa Raychaudhuri, Kensington; Suzanne U. Emerson, Bethesda; Robert H. Purcell, Boyds, all of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/171,387

(22) PCT Filed: Apr. 18, 1997

(86) PCT No.: PCT/US97/06506

§ 371 Date: Mar. 24, 1999

§ 102(e) Date: Mar. 24, 1999

(87) PCT Pub. No.: WO97/40166

PCT Pub. Date: Oct. 30, 1997

Related U.S. Application Data

(60) Provisional application No. 60/015,642, filed on Apr. 19, 1996.

(51) Int. Cl.[7] .................... A61K 39/29; A61K 31/7088; C12N 7/01; C12N 15/51; C12N 5/10

(52) U.S. Cl. ................ 424/189.1; 424/226.1; 435/235.1; 435/325; 435/975; 514/44; 536/23.72

(58) Field of Search .............. 536/23.72, 23.4; 514/44; 424/189.1, 192.1, 199.1, 226.1; 435/235.1, 325, 975

(56) References Cited

U.S. PATENT DOCUMENTS 5,476,658 * 12/1995 Tsarev et al. .............. 424/226.1

OTHER PUBLICATIONS

Emerson et al Journal of Infectious Diseases 173(3): 592–597, Mar. 1996.*
Emerson et al Journal of Virology 66(11):6649–6654, 1992.*
McDonnell et al New England Journal of Medicine 334(1): 42–45, Jan. 1996.*

* cited by examiner

*Primary Examiner*—Mary E. Mosher
(74) *Attorney, Agent, or Firm*—Morgan & Finnegan LLP

(57) ABSTRACT

The present invention discloses simian-human hepatitis A virus chimeric genomes which encode a hepatitis A virus having a chimeric 2C protein. The invention further discloses the use of these viruses or the nucleic acid sequence encoding them as vaccines.

33 Claims, 31 Drawing Sheets

HAV/7

AGM-27

GR2

FIG. 4A  FIG. 4B  FIG. 4C
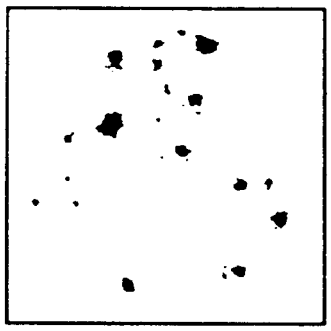 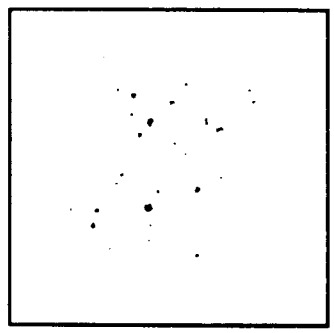 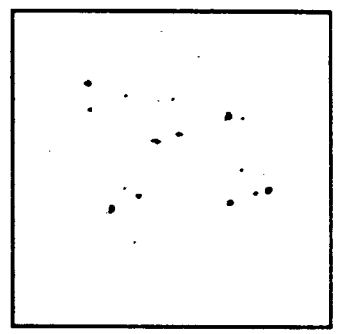
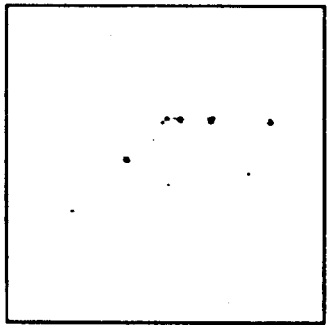 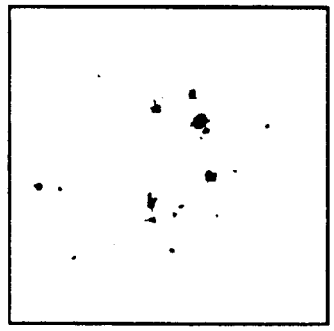 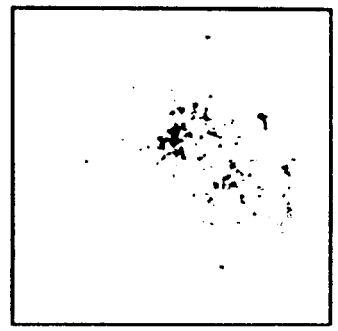
FIG. 4D  FIG. 4E  FIG. 4F

```
GAAGCAGTAGAATCATGAGTGAACTATCTGGAACTCCATCCCATTTTGGCACAGCTCTTATCAATACTATCATTATTCCAAGCATTTGCTGTATAACTGTTGTTACCATGTCTGTGGT
 E  A  G  R  I  M  S  E  L  S  G  T  P  S  H  F  G  T  A  L  I  N  T  I  I  Y  S  K  H  L  L  Y  N  C  C  Y  H  V  C  G
       6750                                            6800                                           6850
TCAATGCCCTCTCCTCTGGGTCTCCCTGTACAGCTTTGCTAAATTCAATTATTAATAATGTCAATTTGTATTATGTTTTCCAAGATATTTGGAAAAGTCTCCAGTTTTCTTTTGTCAGGCTTTG
 S  M  P  S  G  S  P  C  T  A  L  L  N  S  I  I  N  N  V  N  L  Y  Y  V  F  S  K  I  F  G  K  S  P  V  F  F  C  Q  A  L
                             6900                                          6950                                         7000
AAGATTCTGTTGGAGATGATGTTTTCTCTCGAGATGTTCAGATTGATAATCTTGATTTGGACAAAAAATTGTAGATGAGTTTAAGAAACTTGGCATGACAGCT
 K  I  L  C  C  Y  G  D  D  V  L  I  V  F  S  R  D  V  Q  I  D  N  L  D  L  I  G  Q  K  I  V  D  E  F  K  K  L  G  M  T  A
                         7050                                         7100                                          7200
ACTTCTGCTGACAAGAATGTACCTCAGTGAAACCAGTTTCGGAATTGACTTTTTCTCAAAAGATCTTTCAATTGGTAGAGGATAGAATTAGACCTGCAATTTCGGAAAAAACAATTTGG
 T  S  A  D  K  N  V  P  Q  L  K  P  V  S  E  L  T  F  F  L  K  R  S  F  N  L  V  E  D  R  I  R  P  A  I  S  E  K  T  I  W
                          7250                                         7300
TCTTTAATAGCATGGCAGAGAAGATGATAGAACAGACTTAAATCTTATGAGTTTATCAGAAATTTATTATTTGTTCAGTCC
 S  L  I  A  W  Q  R  S  N  A  E  F  E  Q  N  L  E  N  A  Q  W  F  A  F  M  H  G  Y  E  F  Y  Q  K  F  Y  Y  F  V  Q  S
                      7350                                          7400  3D >
TGTTTGGAGAAAGAGATGATAGAACAGACTTAAATCTTATGATTGGTGGAGAATGAGATTTATGACCTTTCATTTGTGACCTTCATTTGTTAAACAAATTTTCTTAAA
 C  L  E  K  E  M  I  E  Y  R  L  K  S  Y  D  W  R  M  R  F  Y  D  Q  C  F  F  I  C  D  L  S  •
            7450                                         7475
ATTTCTGAGGTTTGTTTATTTCTTTTATCAGTAAATAAAAAAAAAAAAAAAA
```

FIG. 13G

| Nucleotide position | Location in HAV | Nucleotide WT | Nucleotide Attenuated | Amino Acid WT | Amino Acid Attenuated |
|---|---|---|---|---|---|
| 124 | 5′ | T | C | | |
| 131 | 5′ | T | d | | |
| 132 | 5′ | T | d | | |
| 133 | 5′ | T | d | | |
| 134 | 5′ | G | d | | |
| 152 | 5′ | A | G | | |
| 203-207 | 5′ | T | d | | |
| 964 | VP2 | A | G | Lys | Arg |
| 1742 | VP3 | G | A | | |
| 3025 | VP1 | A | T | Glu | Val |
| 3196 | 2A | A | G | Asn | Ser |
| 3889 | 2B | C | T | Ala | Val |
| 3919 | 2B | G | C | Gly | Ala |
| 4043 | 2C | T | C | | |
| 4087 | 2C | A | T | Lys | Met |
| 4185 | 2C | G | A | Glu | Lys |
| 4222 | 2C | T | C | Phe | Ser |
| 4563 | 2C | G | A | Val | Ile |
| 5204 | 3A | G | A | | |
| 5232 | 3B | C | T | His | Tyr |
| 6147 | 3D | G | A | Asp | Asn |
| 6522 | 3D | T | A | Ser | Thr |
| 7032 | 3D | T | C | | |
| 7430 | 3′ | A | G | | |

FIG. 14

| | | | | | |
|---|---|---|---|---|---|
| CTTGATACCT | CACCGCCGTT | TGCCTAGGCT | ATAGGCTTCT | TCCCTACACC | CTTGTTTGTT | 60 |
| TTTTTTTTTT | TTTTTTGTGT | GTTTGTAAAT | ATTAATTCCT | GCAGGTTCAG | GGTTCTTAAT | 120 |
| TTGTTCTGCT | ATACAGACAC | TCTTTTCACG | CTTTCTGTCA | TCTTATTTCC | TGGGCTCTCC | 180 |
| CCTTGCCCAA | GGCTCTGGCC | GTTGCGCCCG | GCGGGGTCAA | CTCCATGGTT | AGCATGGAGC | 240 |
| TGTAGGAGTC | TAAATTGGGG | ACGCAGATGC | TAGGAACGTC | GCCCTGCAGT | GTTAACCTGG | 300 |
| CTTTCATGAA | GCTCTTTGAT | CTTCTACAAG | AGGTAGGCTA | CGGGTGAAAC | CTCTTAGATT | 360 |
| AATACTCCTA | TGGAGAGATA | TCTTGAATAG | GGTAACAGCG | GTGGATATTG | GTGAGTTCCT | 420 |
| TTGGGACAAA | AACCATTCAA | CACCGGAGGA | CTGACTCTCA | TTCAGTAGTT | GCATTGAGTG | 480 |
| AATTGTCTGT | CAGGGCTGTC | TTTGGGTTTA | ATTCCTGGCC | TCTCTGTGCT | TAGGGCAAAC | 540 |
| CATTTCCTGG | CCTTAAATGG | AGTTCTGTGA | GAGGGAACTC | CTCCTTTATA | TGCTGGACAT | 600 |
| ATTTTGGGGC | CTTAGGGTTA | TGGTTTGCCT | CTGAGGTACT | CAGGGGCATT | TAGGTTTTTC | 660 |
| CTCATTTATA | TGTTTATGAT | GATGAATATG | TCTAAACAAG | GTATTTTCCA | GACTGTTGGG | 720 |
| AGTGGCCTTG | ACCACATACT | GTCTTTAGCA | GATGTGGAGG | AAGAGCAAAT | GATACAGTCA | 780 |
| GTGGACAGGA | CAGCTGTCAC | TGGTGCTTCT | TATTTTACTT | CTGTAGACCA | ATCTTCAGTT | 840 |
| CATACGGCAG | AAGTTGGTGC | ACATCAGACA | GAGCCTCTTA | AGACATCAGT | AGATAAACCA | 900 |
| GGTTCAAAGA | AAACCCAAGG | AGAGAAATTT | TTCCTAATAC | ATTCTGCAGA | TTGGTTAACA | 960 |
| ACACATGCTT | TGTTTCATGA | AGTCGCCAAA | TTGGATGTTG | TTAGTTTGTT | GTACAATGAA | 1020 |
| CAATTTGCTG | TACAGGGTTT | GTTGAGATAC | CATACTTATG | CTAGATTTGG | AATTGAAATT | 1080 |
| CAAGTCCAGA | TTAATCCCAC | TCCCTTTCAG | CAGGGAGGTC | TTATTTGTGC | AATGGTTCCA | 1140 |
| GGAGACCAAG | GTTATGGTTC | CATAGCCTCA | TTGACAGTTT | ATCCACATGG | TCTCTTGAAT | 1200 |
| TGCAACATTA | ACAATGTTGT | TAGAATCAAA | GTTCCATTCA | TTTATACTAG | AGGTGCTTAT | 1260 |
| CATTTCAAAG | ATCCACAGTA | TCCAGTCTGG | GAGTTAACTA | TTCGTGTTTG | GTCAGAATTA | 1320 |
| AATATAGGAA | CTGGTACTTC | TGCTTATACA | TCATTGAATG | TCTTGGCTAG | ATTCACTGAT | 1380 |
| TTAGAGCTTC | ATGGATTGAC | ACCATTATCT | ACACAAATGA | TGAGGAATGA | ATTTAGAGTG | 1440 |
| AGTACAACTG | AAAATGTGGT | TAATTTGTCA | AATTACGAGG | ATGCTAGAGC | AAAGATGTCT | 1500 |
| TTTGCACTTG | ATCAGGAAGA | TTGGAAAACA | GATCCCTCGC | AAGGAGGAGG | AATCAAAATC | 1560 |
| ACTCATTTTA | CAACATGGAC | TTCAATTCCC | ACGCTTGCTG | CACAGTTTGC | ATTTAATGCT | 1620 |

FIG. 15A

```
TCTGCATCTG TGGGGCAGCA AATTAAGGTG ATCCCTGTTG ATCCTTATTT TTATCAGATG  1680
ACCAATTCAA ATCCAGACCA AAAGTGTATT ACTGCTTTAG CTTCTGTCTG TCAGATGTTC  1740
TGCTTTTGGA GGGGAGATCT TGTTTTTGAT TTTCAGGTTT TCCCCACAAA ATATCACTCT  1800
GGGAGGTTGT TATTTTGTTT TGTGCCAGGG AATGAGTTGA TAGATGTTTC AGGTATAACC  1860
CTGAAGCAGG CAACTACTGC ACCCTGTGCT GTTATGGATA TAACAGGAGT TCAGTCAACA  1920
TTGAGATTTA GAGTGCCTTG GATCTCTGAT ACACCTTACA GAGTGAATAG ATACACAAAA  1980
TCAGCTCACC AGAAAGGAGA GTATACAGCT ATTGGGAAGT TGATTGTTTA TTGTTATAAT  2040
AGGCTTACCT CACCCTCAAA TGTTGCTTCC CATGTTAGGG TTAATGTTTA TCTTTCTGCA  2100
ATAAATTTGG AATGTTTTGC ACCCCTATAT CATGCAATGG ATGTGACATC ACAGACAGGT  2160
GATGATTCAG GTGGGTTTTC AACTACAGTT TCTACAGAAC AGAATGCTCC TGATCCTCAA  2220
GTTGGAATTA CCACTATTAA GGATTTAAAA GGGAAGGCAA ATAGAGGAAA GATGGATGTT  2280
TCTGGCATTC AAGCACCAGT GGGTGCTATT ACAACCATTG AGGATCCAGT GTTAGCTAAA  2340
AAAGTTCCTG AGACTTTTCC AGAATTGAGA CCAGGTGAAT CTAGACATAC TTCAGATCAT  2400
ATGTCTATTT ACAAATTTAT GGGGAGGTCA CACTTTCTTT GTACATTTAC TTTCAATGCA  2460
AACAATAGGG AGTATACTTT TCCAATAACA CTGTCCTCTA CATCGAATCC ACCTCATGGT  2520
TTACCATCAA CACTGAGGTG GTTTTCAAC CTTTTTCAAT TGTATAGAGG GCCATTGGAC  2580
TTGACTATTA TAATTACAGG TGCTACTGAT GTGGATGGCA TGGCTTGGTT TACTCCTGTG  2640
GGCCTAGCTG TGGATACTCC CTGGGTTGAA AAGCAATCAG CGTTGACTAT TGATTATAAA  2700
ACTGCTCTTG GGGCTATTAG GTTTAACACT AGGAGAACAG GAAATATTCA GATTAGACTT  2760
CCTTGGTATT CATACCTTTA TGCTGTTTCT GGCGCTTTGG ATGGACTTGG GGACACTACT  2820
GATTCGACTT TCGGGTTGGT CTCTATTCAG ATTGCCAATT ATAATCATTC AGATGAATAT  2880
CTGTCATTCA GTTGTTATCT TTCAGTTACT GAACAATCAG AATTTTATTT TCCAAGGGCT  2940
CCTCTCAATT CTAATGCTAT GATGGTTTCT GAGTCCATGC TAGATCGCAT TGCAAGTGGA  3000
GATTTAGAAT CATCAGTTGA TGACCCAAGA TCAGCAGAGG ACAAAAGGTT TGAAAGTCAT  3060
ATTGAGCAGG GCAAGCCATA CAAAGAATTA AGAATGGAAG TTGGGAAGCA GAGATTGAAA  3120
TATGCCATGG AGGAGTTATC AAATGAAATT TTACCACCTC CTCGGAAAGT GAAAGGACTG  3180
TTTTCTCAAG CTAAAATTTC TTTATTTTAT ACAGAAGACC ATGAAATTGT GAAGCTTTCA  3240
```

FIG. 15B

```
TGGAAAGGTC TCACAGCTGA TACAAGAGCT CTCAGGAGAT ATGGTTTTTC TCTTGCTGCT    3300
GGAAGAAGTG TGTGGACTCT TGAGATGGAA GCTGGAGTTC TGACTGGAAG GATGATCAGA    3360
TTGAATGATG AAAAGTGGAC TGAGATTAAG GATGATAAGA TAGTGGCTTT GGTAGAGAAA    3420
TTTACATCTA ATAAGAATTG GTCTAAAGTC AATTTTCCAC ATGGGATGCT AGATTTGGAA    3480
GAGATAGCAT CAAATTCAAA GGATTTTCCT AATATGTCTG AGACTGACTT GTGTTTTCTT    3540
TTACATTGGT TGAATCCTAA GAAGATAAAT CTAGCTGATA GAATGCTTGG ATTGTCTGGT    3600
GTTCAGGAAA TTAAGGAACA GGGTGTTGGC TTAATAGCTG AATGTAGAAC ATTTTTAGAT    3660
TCTATAGCTG GCACTTTGAA ATCAATGATG TTTGGGTTTC ATCAGTCTGT TACTGTGGAA    3720
ATAATTAATA CTGTCTTGTG TTTTGTTAAG AGTGGGATCC TTCTTTATGT TATTCAGCAA    3780
TTGAATCAAA ATGAACACTC TCATATTATA GGGCTTTTAC AGGTGATGAA TTATGCAGAC    3840
ATTGGTTGCT CTGTGATTTC TTGTGGAAAG ATATTCTCAA AAATGTTAGA AACAGTCTTT    3900
AATTGGCAGA TGGATTCTAG AATGATGGCT CTTAGAACAC AGAGTTTCTC TAATTGGTTG    3960
AGAGACATAT GTTCGGGGAT AACCATTTTC AAAAATTTTA AGGATGCTAT TTTCTGGCTG    4020
TACACTAAAT TAAAGGATTA TTATGATTCT AACTATGGGA AAAAGAAGGA TGTTCTGAAT    4080
GTTTTAAAAG AAAATCAGCA TAGGATTGAG AAAGCCATTG AAGAGGCTGA TCAGTTCTGT    4140
GTTTTGCAGA TTCAGGACGT TGAGAAGTCA GAGCAATATC AGAAGGGAGT TGAACTCATT    4200
CAGAAATTGA GAACAGTTCA TTCCCTGGCC CAGGTCGACT CTAGTTTGAT GTCTCATTTG    4260
TCACCACTGA GAGATTGTAT TGCTAGAGTC CATCAAAAAC TTAAGAATTT AGGCTCAATT    4320
AATCAGGCTA TGGTGACTAG GTGTGAACCT GTGGTCTGTT ATTTATATGG TAAGAGAGGT    4380
GGAGGAAAGA GTTTAACTTC TATTGCATTG CAACAAAAAA TTTGCAAACA TTATGGTGTT    4440
GAACCAGAAA AGAATATATA TACAAAACCT GTTGCTTCAG ACTACTGGGA TGGATATAGT    4500
GGTCAATTGG TTTGTATCAT TGATGACATT GGTCAAAATA CTACAGATGA AGATTGGTCA    4560
GATTTTTGTC AATTGGTGTC TGGTTGTCCT ATGAGGTTAA ATATGGCTTC TTTGGAAGAG    4620
AAAGGGAGAC ACTTTTCTTC CCCGTTTATA ATTGCCACAT CAAATTGGTC AAATCCAAGT    4680
CCTAAGACTG TTTATGTGAA GGAAGCTATA GATCGCCGCC TTCATTATAA GATTGAAGTC    4740
AAACCAGCAT CTTTTTACAA AAATGCACAC AATGATATGC TCAATGTGAA TCTTGCAAGA    4800
AATAATGATG CCATTAAAGA CATGTCCTGT GTAGATTTAC TGATGGATGG CCATACTGTG    4860
```

FIG. 15C

```
TCTTTATCTG AGCTTTTAAA TTCTCTTGTT ATGACAGTTG AAATTAGAAA ACAAAATATG   4920
TCAGAATTTA TGAAATTGTG GTCACAGGGT GTGTCAGATG ATGATAATGA CAGTGCAGTT   4980
GCTGAGTTCT TCCAGTCTTT TCCATCAGGA GAACCCTCAA ATTCTAAGTT ATCTAGTTTC   5040
TTCAAGGCGG TCACTAATCA TAAGTGGGTT GCTATTGGAG CTGCTGTTGG AGTTCTGGGT   5100
GTCTTAGTGG GAGGTTGGTT TGTGTACAAG CATTTTACCA AAGAAGAACC AATACCAACT   5160
GAAGGAGTGT ATCATGGAGT AACCAAACCT AAACAGGTTA TCAAATTGGA TGCTGATCCT   5220
GTTGACTCCC AATCTACTCT TGAGATAGCT GGACTAGTTA GGAAGAATTT GGTTCAATTT   5280
GGAGTTGGGG AGAAGAATGG ATGTGTTAGG TGGGTCATGA ATGCTTTAGG TATTAAAGAT   5340
GATTGGCTGC TGGTCCCCTC ACATGCATAC AAATTTGAGA AAGATTATCA AATGATGGAG   5400
TTTTATTTTA ATAGAGGAGG AACTTATTAT TCAATTTCTG CTGGTAATGT TGTAATCCAG   5460
TCTTTGGATG TTGGTTTTCA GGATGTTGTT TTGATGAAGG TTCCTACAAT TCCAAAGTTT   5520
AGAGATATAA CTGAGCATTT TATTAAGAAG AATGATGTTC CAAGAGCTTT GAATAGATTG   5580
GCTACACTTG TTACAACAGT TAATGGGACA CCAATGCTGA TTTCCGAAGG TCCACTTAAG   5640
ATGGAAGAAA AGGCCACTTA TGTCCATAAG AGAAATGACG GAACTACTGT TGATTTGACT   5700
GTTGATCAAG CTTGGAGGGG AAAAGGTGAG GGCCTCCCAG GTATGTGTGG TGGAGCTCTG   5760
ATTTCCTCAA ATCAGTCAAT ACAAAATGCC ATTCTTGGGA TTCATGTTGC AGGTGGCAAT   5820
TCTATTTTGG TTGCCAAACT TGTGACTCAG GAAATGTTCC AGAACATTGA ACAAAAAGCA   5880
ATAGAAAGTC AGAGGATAAT GAAAGTGGAA TTCACTCAGT GTTCAATGAA TGTGGTCTCC   5940
AAAACGCTTT TTAAAAAGAG TCCAATTCAT CATCACATTG ATAGGAACAT GATTAATTTT   6000
CCTGCTGTAA TGCCTTTTTC TAAAGCTGAG ATTGATCCTA TGGCTGTTAT GTTGTCTAAG   6060
TATTCTCTTC CTATTGTTGA AGAGCCAGAT GATTATAAGA TGGCTTCCAT TTATTTCCAA   6120
AATAAAGTAA TGGGGAAAAC TTTTCTTGTT GATGACTTTT TGGATATAGA TATGGCAATC   6180
ACAGGTGCTC AGGAATAGA TGCTATTAAT ATGGATTCTT CACCAGGATT TCCTTATGTT   6240
CAGGAGAAGT TGACAAAGAA AGACTTGATC TGGTTGGATG AGAATGGGCT GCTGTTAGGA   6300
GTTCATCCAA GGCTTGCTCA AGAATCTTG TACAACACAG TTATGATGGA GAATTGTTCT   6360
GATCTTGATG TGGTCTTTAC AACATGTCCC AAGGATGAAC TTAGGCCTCT GGACAAAGTA   6420
TTGGAATCAA AGACTAGAGC AATTGATGCT TGTCCATTGG ATTATACAAT TCTTTGTAGG   6480
```

FIG. 15D

```
ATTTATTGGG GTCCTGCTAT TAGTTACTTT CAATTGAATC CTGGATTTCA CACAGGAGTT    6540
GCTATTGGAA TTGATCCGGA TAGACATTGG GACGAGTTGT TTAAAACAAT GGTTAGATTT    6600
GGTGATGTAG GTTTAGACCT TGATTTTTCA TCATTTGATG CTAGTCTTAG TCCTTTTATG    6660
ATAAGAGAGG CAGGGAGAAT TTTGAGTGAA ATGTCAGGGA CACCCTCACA CTTTGGAGAG    6720
GCCTTGATTA ATACAATCAT TTATTCCAAG CATTTGTTGT ACAATTGTTG TTATCATGTT    6780
TATGGTTCCA TGCCATCAGG GTCCCCTTGT ACAGCACTTT TAAATTCAAT TGTAAACAAT    6840
GTTAATTTGT ACTATGTGTT TTCAAAAATT TTTAGGAAGT CTCCTGTTTT CTTTGGAGAT    6900
GCTCTGAAGA TTCTTTGTTA TGGAGATGAT GTCCTCATTG TTTTTTCCAG AAATGTCCAG    6960
ATTGATAATT TGGAATCTAT TGGACAGAAA ATTGTAGATG AGTTTGGAAA ATTAGGCATG    7020
ACTGCAACAT CAGCAGACAA GTCTGTTCCT AAGTTGAAAC CTATTTCTGA GCTCACTTTT    7080
CTTAAAAGAT CATTCAATCT TGTTGAAGAT CGGATTAGAC CTGCAATTTC AGAGAAAACA    7140
ATTTGGTCTC TCGTTGCTTG GCAGAGAAGC AATGCTGAAT TGAACAGAA  TTTGGAAAAT    7200
GCTCAATGGT TTGCTTTTAT GCATGGTTTT GAATTTTATC AGAAATTTTA CCATTTTGTT    7260
CAGTCCTGCC TGGAGAAAGA GATGGTAGAA TACAGATTGA AATCATATGA TTGGTGGAGA    7320
ATGAAGTTTT ATGATCAGTG CTTTGTTTGT GACCTCACAT GATTTGTTTA AACAAACCTT    7380
CTTAAAATTT CTGAGATTTG                                                7400
```

SIMIAN-HUMAN HAV HAVING A CHIMERIC 2C PROTEIN

This application claims the benefit of International Application No. PCT/US97/06506, filed on Apr. 18, 1997, and U.S. Provisional Application No. 60/015,642 filed Apr. 19, 1996.

FIELD OF THE INVENTION

The present invention relates to molecular approaches to the development of a live hepatitis A vaccine. In particular, the invention relates to nucleic acid sequences which encode hepatitis A viruses having a chimeric 2C protein. More specifically, the nucleic acid sequences of the invention comprise a genome of a human hepatitis A virus strain which contains a chimeric 2C gene consisting of sequences from both a human strain and the simian AGM-27 strain. The invention further relates to the use of these viruses, or the nucleic acid sequences encoding them, as vaccines.

BACKGROUND OF THE INVENTION

Hepatitis A virus (HAV) is a picornavirus with a ~7.5 kb positive strand RNA genome and is the sole member of the Hepatovirus genus (Francki, R. I. B., et al. (1991) Classification and Nomenclature of Viruses. (Arch. Virol./Suppl. 2). Springer, Vienna). The clinical manifestations of HAV infection in humans can vary greatly, ranging from asymptomatic infection, commonly seen in young children, to fulminant hepatitis, which in some cases can result in death (Ross, B. C., et al. (1991) Adv. Virus Res., 39:209–253).

In attempting to prevent hepatitis A, three general strategies are possible: 1) increasing hygiene standards; 2) passive immunization of those known to be exposed to HAV with normal human immune globulin; and 3) the development of HAV vaccines. However, because sanitation levels in underdeveloped countries remain low and passive immunization offers little hope for control of endemic hepatitis A since most cases of hepatitis A occur in individuals who do not have a specific exposure history, considerable research efforts have been devoted to the development of either live or killed vaccines.

With respect to killed or inactivated vaccines, numerous laboratories have reported the development of inactivated HAV vaccines (see, for example, Binn, L. N. et al. (1986) J. Inf. Dis., 153:749; Provost, P. J. et al. (1986) J. Med. Virol., 19:23; Flehmig, B. et al. (1989) Lancet i:1039 and Andre, F. E. et al. (1990) Progress in Med. Virol., 37:72) and Smith-Kline Beecham and Merck have recently licensed and sold inactivated HAV vaccines containing different strains of HAV. However, the high cost of inactivated HAV vaccines makes their use in other than high-risk individuals unlikely. In addition, questions concerning the duration of immunity induced by inactivated HAV vaccines suggests that multiple doses may need to be administered to confer continued protection. Thus, for these reasons, the widespread use of live attenuated HAV vaccines in underdeveloped countries where hepatitis A is endemic may be more feasible and more efficacious than use of inactivated vaccines.

In attempting to develop a live attenuated vaccine, numerous investigators have selected attenuated hepatitis A viruses by passage of wild-type HAV strains in cell culture (see, for example, Provost et al. (1986) J. Med. Virol., 20:165–176; Karron, R. A. et al. (1988) J. Infect. Dis., 157:338–345). However, attenuation of HAV strains during adaptation to growth in cell culture has been observed to result in over-attenuation such that the attenuated viruses, when administered as live vaccines, are no longer effective inducers of anti-HAV antibodies in vivo (Provost, P. J. et al. (1986) J. Med. Virol., 20: 165– 175).

A potential alternative approach to the production of a candidate live attenuated vaccine strain which grows sufficiently well in a cell line to make vaccine production economically feasible and which is also infectious, immunogenic and avirulent in humans, is the use of recombinant DNA methodology to construct chimeric HAV genomes.

SUMMARY OF THE INVENTION

The present invention relates to nucleic acid sequences which comprise a genome of a human hepatitis A strain which contains a chimeric 2C gene consisting of sequences from both the human strain and the simian AGM-27 strain. The nucleic acid sequences of the invention are designated "2C chimeric genomes".

It is therefore an object of the invention to provide nucleic acid sequences which encode hepatitis A viruses having a chimeric 2C protein. For the purposes of this application, nucleic acid sequence refers to RNA, DNA, CDNA or any variant thereof capable of directing host organism synthesis of hepatitis A viruses having a chimeric 2C protein.

The invention also relates to hepatitis A viruses encoded by the 2C chimeric genomes. These viruses are designated "2C chimeric hepatitis A viruses."

The invention further provides vaccines for use in immunizing a mammal against hepatitis A. In one embodiment, the vaccine comprises a 2C chimeric hepatitis A virus. In a second embodiment, the vaccine comprises a 2C chimeric genome which encodes a hepatitis A virus having a chimeric 2C protein.

The invention therefore also relates to methods for preventing hepatitis A in a mammal. In one embodiment, the method comprises administering to a mammal an amount of a 2C chimeric genome of the invention effective to induce protective immunity against hepatitis A. In another embodiment, the method of prevention comprises administering to a mammal a 2C chimeric hepatitis A virus in an amount effective to induce protective immunity against hepatitis A.

The invention also provides pharmaceutical compositions comprising the 2C chimeric genome of the invention and/or their encoded hepatitis A viruses.

The invention further provides kits comprising the 2C chimeric nucleic acid sequences of the invention.

The invention further relates to antibodies to 2C chimeric hepatitis A viruses and to pharmaceutical compositions comprising these antibodies.

DESCRIPTION OF FIGURES

FIGS. 4A–4F shows the results of a radioimmunofocus assay comparing focus size of chimeras that differ in the truncated 2B gene sequence and/or the 2C gene sequence. (A) HAV/7, (B) GR2, (C) GR3, (D) GR4, (E) GR15 and (F) GR9.

FIGS. 11A–11D show biochemical, serological (anti-HAV) and histopathological analyses of two chimpanzees, 1558 (FIGS. 11A and 11C) and 1564 (FIGS. 11B and 11D), inoculated with the GR4 chimera. In FIGS. 11A and 11B, the biochemical responses are shown as ICD levels where the ICD serum enzyme levels were measured in international units per ml (IU/ml). In FIGS. 11C and 11D, the biochemical responses are shown as ALT levels where the ALT levels were measured in international units/ml. A + in the row marked "anti-HAV" indicates samples that were positive for anti-HAV antibodies as determined by commercial assay. The histopathology scores correspond to mild hepatitis (1+), mild to moderate hepatitis (2+), moderately severe hepatitis (3+) and severe hepatitis (4+). The "ND" designation signifies that liver histology analysis was not performed for these samples.

Figure 13A:
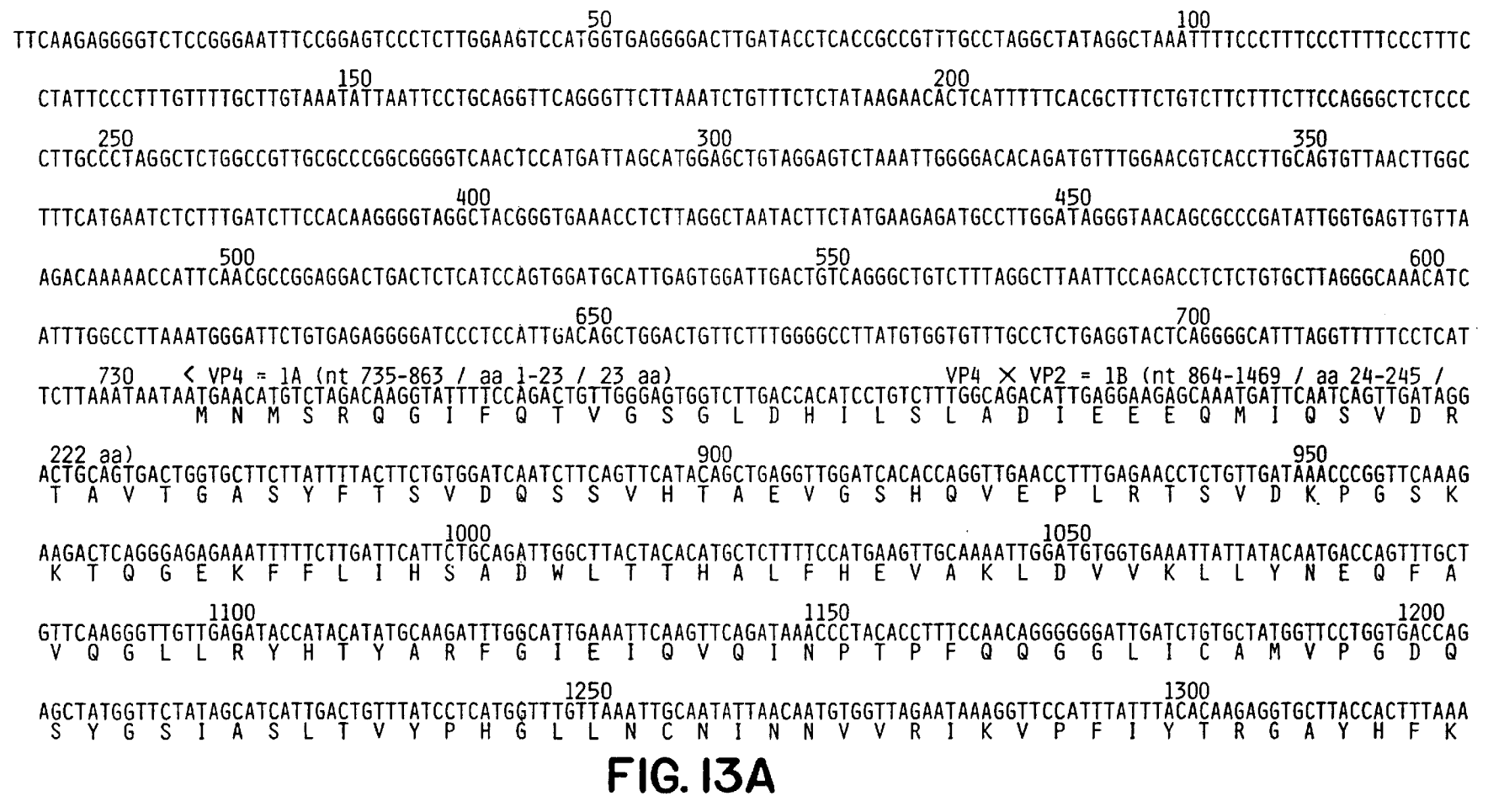
Figure 13B:
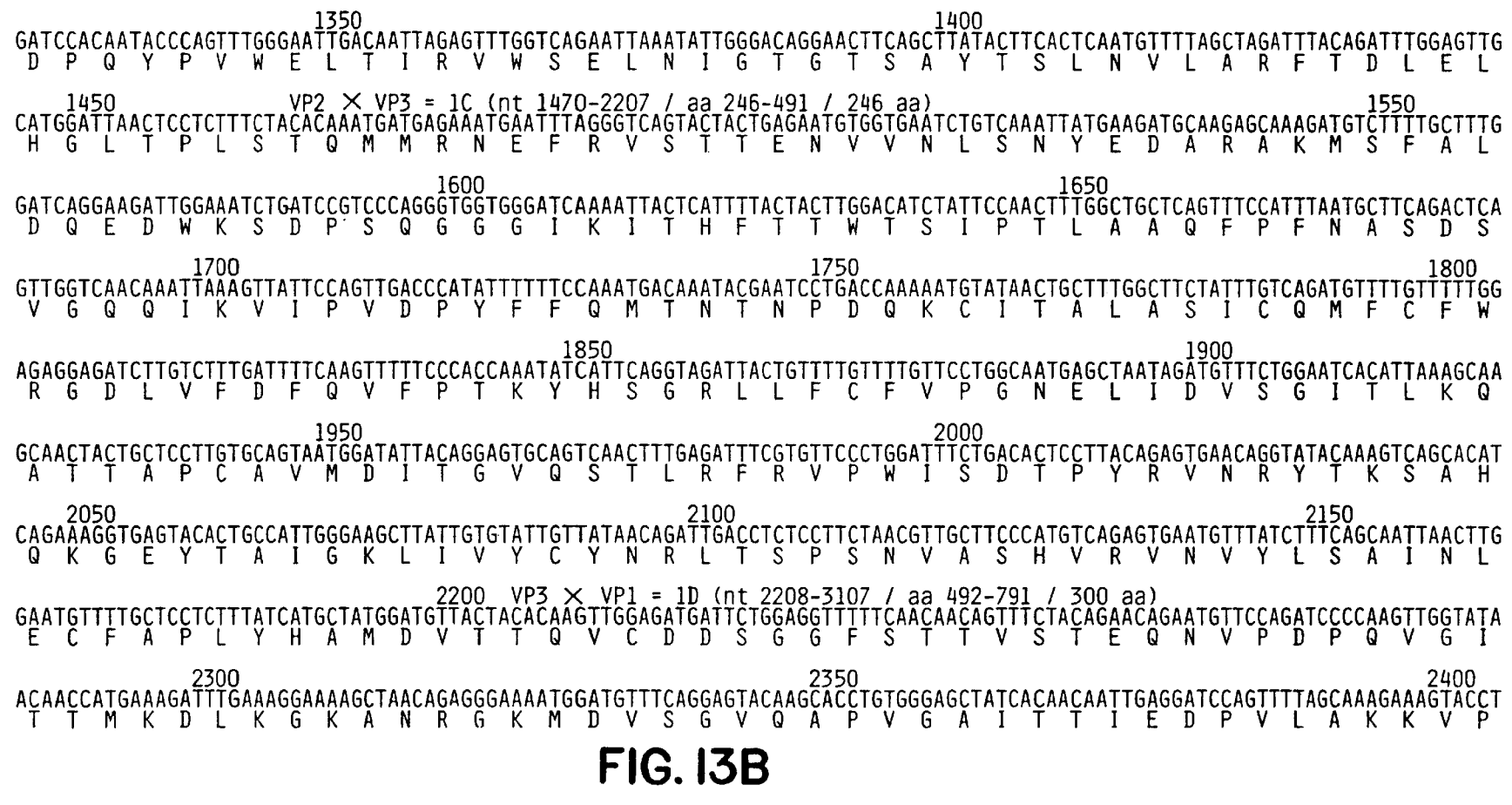
Figure 13C:
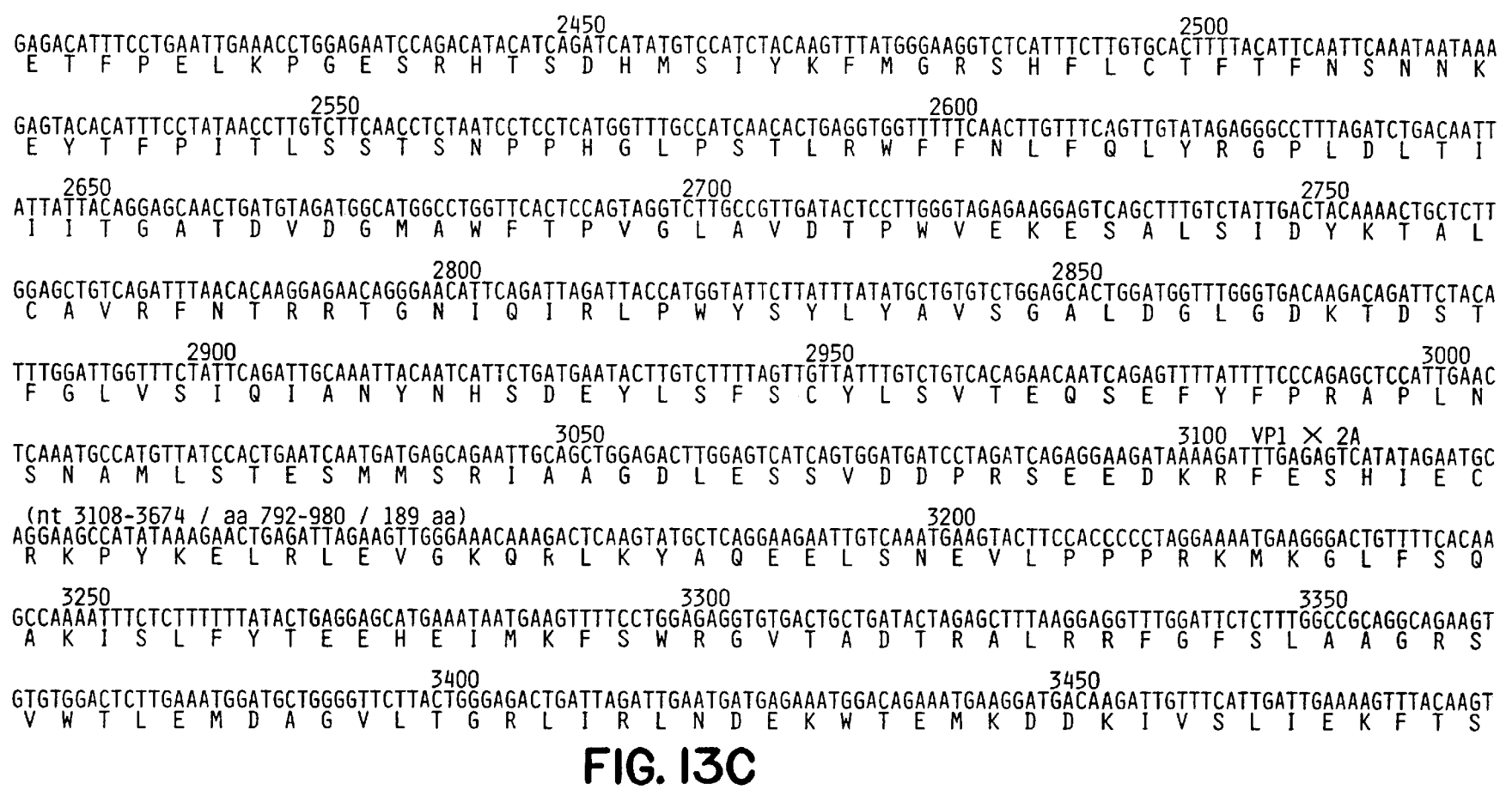
Figure 13D:
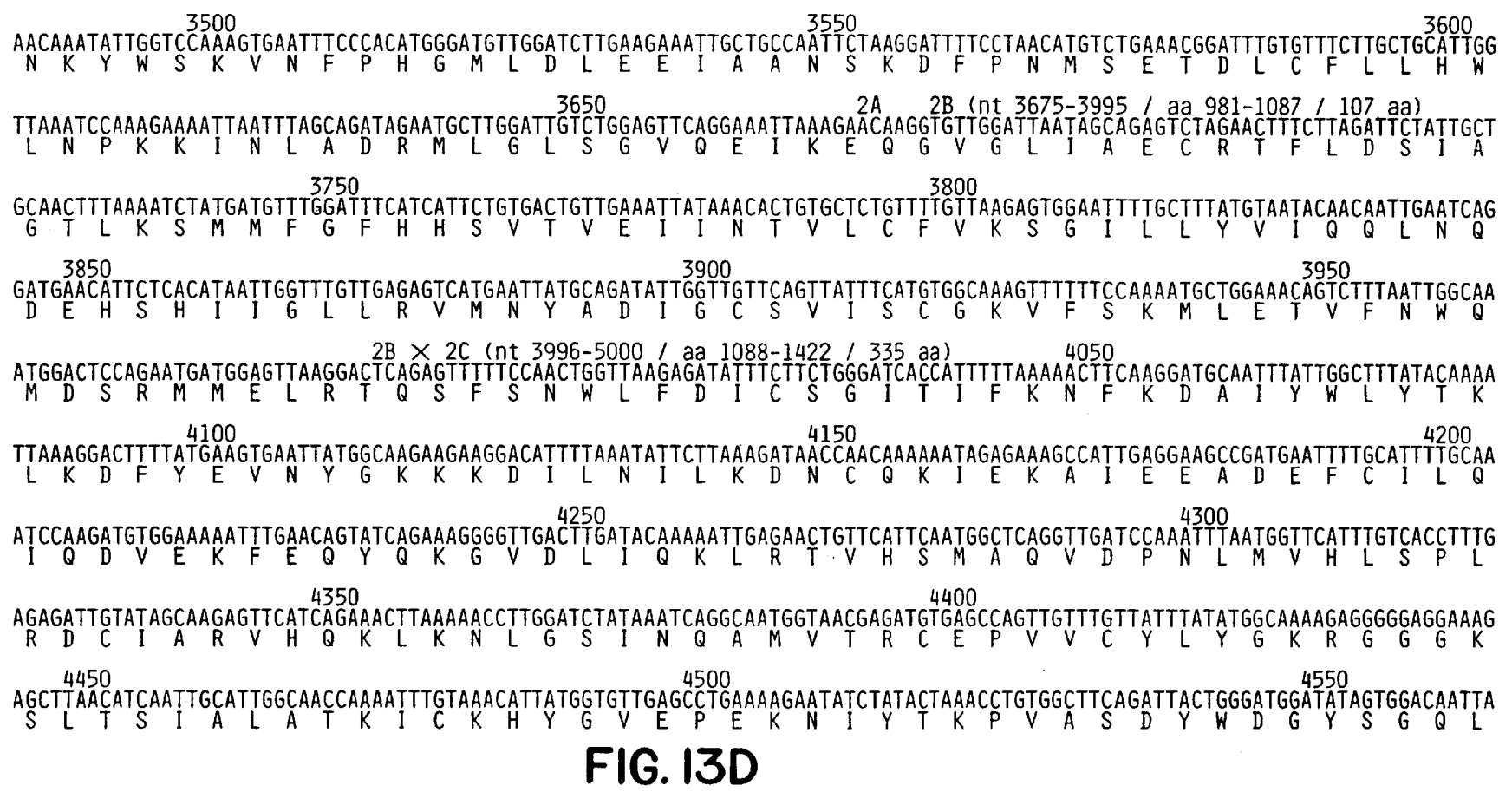
Figure 13E:
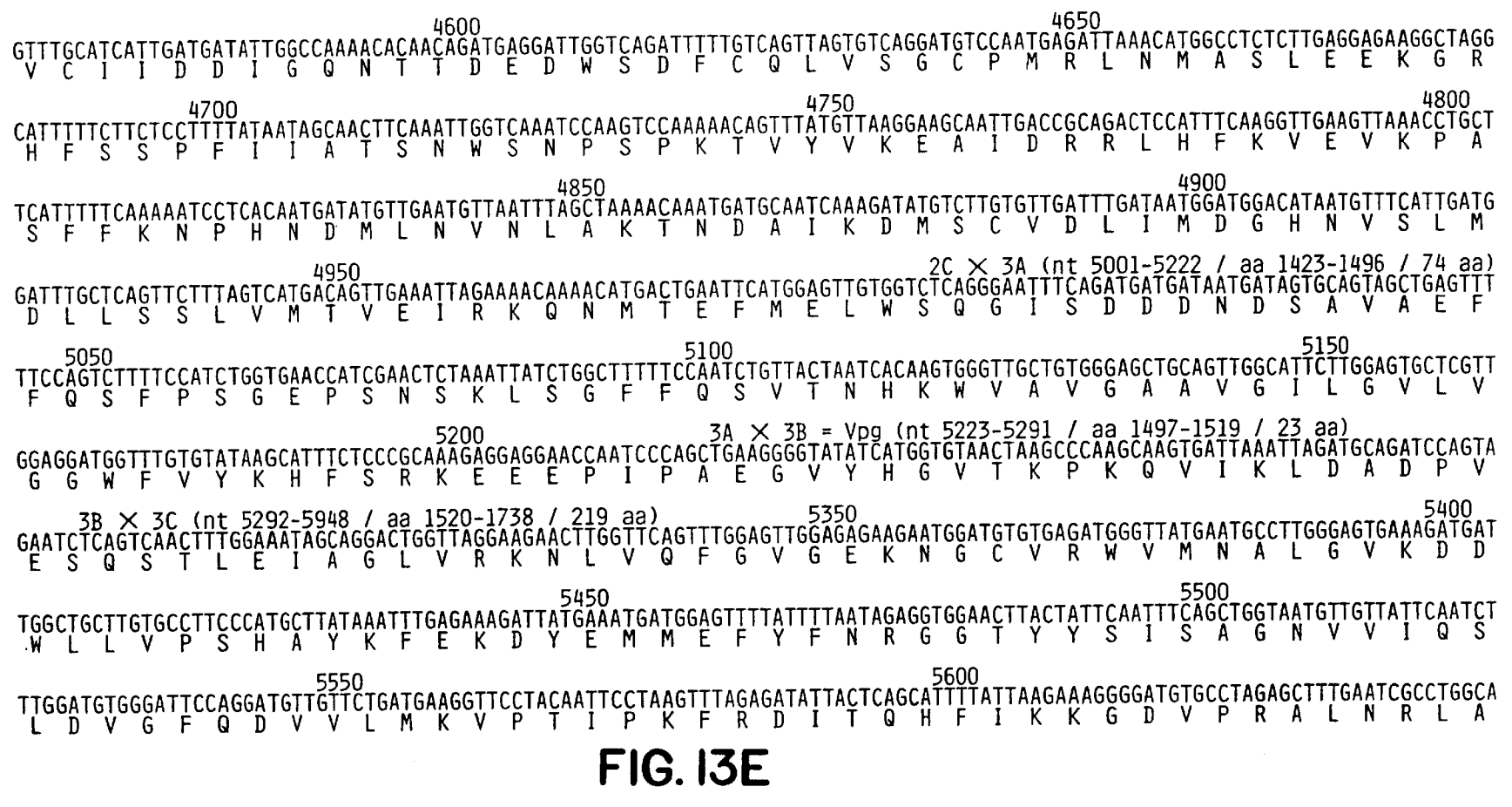
Figure 13F:
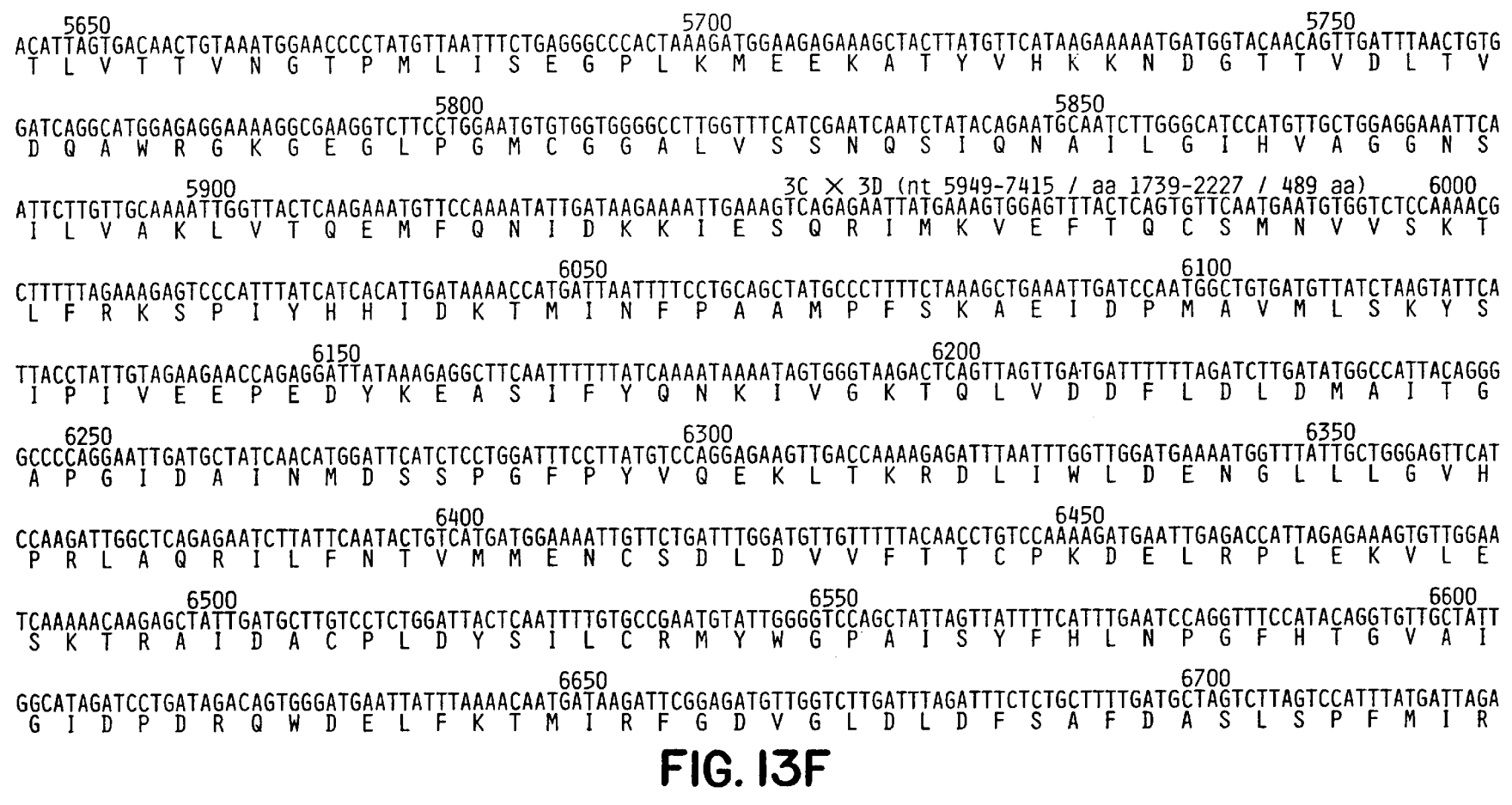

FIGS. 13A–13G show the complete nucleotide (SEQ ID NO: 1) and predicted amino acid sequences for wild-type HAV HM-175.

FIG. 14 shows the results of a comparison between the genome sequences of wild-type (WT) HAV HM-175 (shown in FIGS. 13A–13D) and attenuated (attenuated) cell-culture adapted HAV/7 where the difference between the two genomes are indicated in the columns marked WT and attenuated. Nucleotide positions correspond to numbering for wild-type HM-175 shown in FIGS. 13A–13D.

FIGS. 15A–15E show the nucleotide sequence of greater than 99% of the entire genome of AGM-27 (SEQ ID No: 3). The sequence determined for AGM-27 starts from nucleotide 59 according to the nomenclature for wild-type HM-175.

DESCRIPTION OF INVENTION

Figure 1:
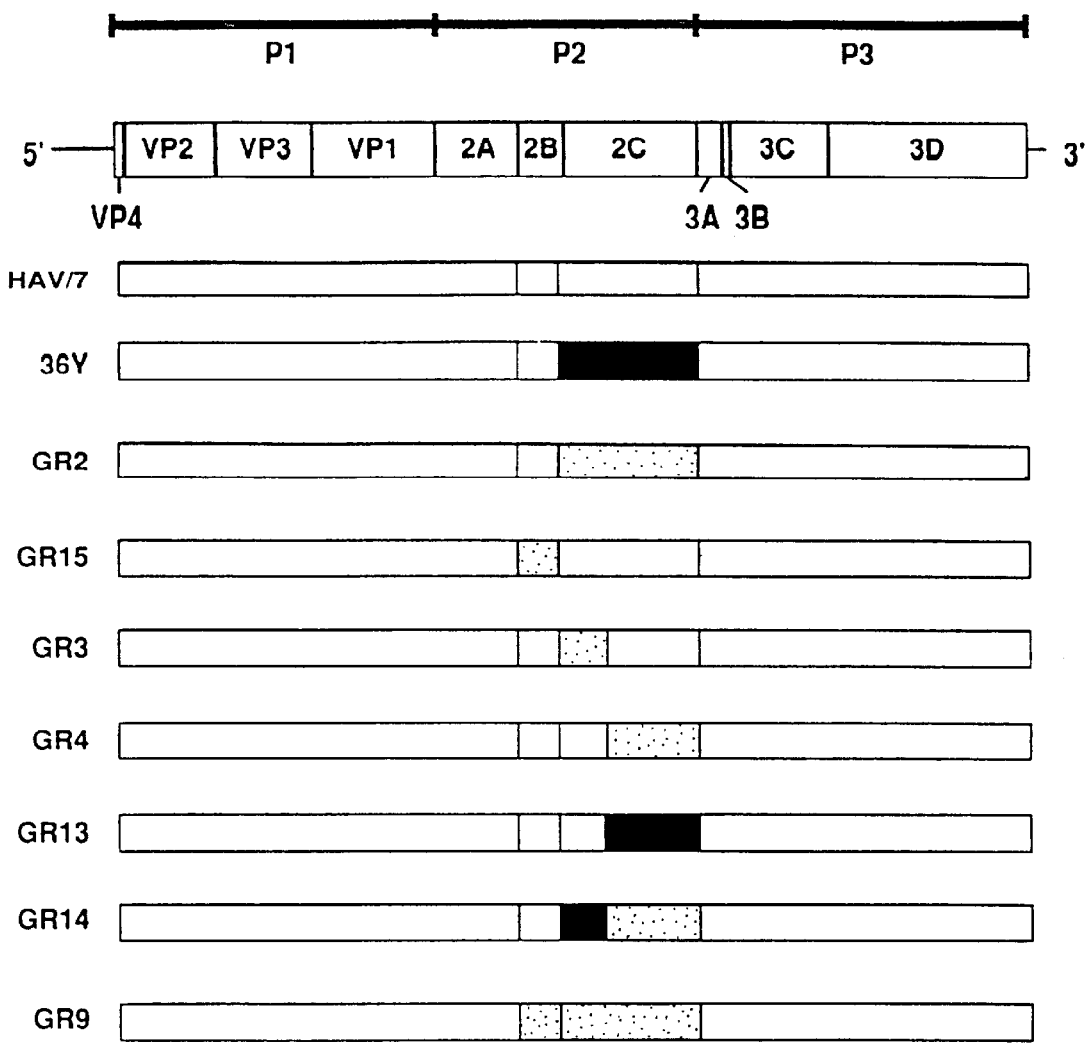
FIG. 1 shows the genomic structure of full-length cDNA clones of chimeras consisting of HAV/7 (white), a cell culture-adapted variant of wild-type HM-175 HAV derived by passage of HM-175 35 times in primary African Green Monkey kidney cells (see Table 1 of Cohen et al (1987) Proc. Nat'l Acad. Sci USA, 84:2497–2501 for HAV/7 sequence), wild-type HM-175 (black) (see FIG. 1 of Cohen et al (1987) J. Virol., 61:50–59 for wild-type HM-175 sequence) and AGM-27 (grey) (see SEQ. ID. NO:1 of U.S. Pat. No. 5,476,658 for AGM-27 sequence) sequences. The chimeras were constructed using DNA fragments from molecular clones of HAV/7 and wild-type HM-175 and fragments of PCR amplified cDNA from the AGM-27 virus. The 2A/2B junctions in the diagrams presented in this application correspond to the cleavage site designation of Cohen et al. (1987) (*J. Virol.,* 61:50–59) at nucleotides 3674/3675. However, recent results have shown that the 2A/2B junction is in fact nucleotides 3242/3243. Thus, when reference is made to the "2B gene" or "2B sequence" in this application it refers to the 2B gene as defined by Cohen et al. (*J. Virol.* 61:50–59) which is in reality a truncated 2B which consists of approximately 42% of the residues at the 3' end of the 2B gene.

The present invention relates to nucleic acid sequences which encode a hepatitis A virus having a chimeric 2C protein. More specifically, the invention relates to nucleic acid sequences which comprise a genome of human hepatitis A strain having a chimeric 2C gene which consists of sequences from both the human strain and the simian AGM-27 strain. In a preferred embodiment, the human hepatitis A strain is an attenuated hepatitis A strain such as MRC5 or HAV/7. In a more preferred embodiment, the attenuated human hepatitis A strain is HAV/7 (Cohen et al. (1987) *Proc. Natl. Acad. Sci. USA,* 84:2497–2501). Thus, in a preferred embodiment, the 2C chimeric genomes of the invention comprise a genome of the HAV/7 strain having a chimeric 2C gene which consists of sequences from both the HAV/7 strain and the simian AGM-27 strain.

Chimeras of the invention can be generated from the pGRI, pGR2 and pHAV/7 full-length clones presented herein in the Examples section through the use of PCR and cloning techniques.

Chimeras of the invention include chimeras 1–18, which are generated by PCR amplification of HAV/7 sequence using primers with engineered restriction sites followed by subcloning into the pGR2 background.

| Chimera # | HAV/7 Region Amplified | AGM-27 2C Amino Acid Sequence in Chimera | # AGM-27-specific 2C Amino Acid Residues in Chimera |
|---|---|---|---|
| 1 | PpuM1 to DraI | residues 48–328 | 23 |
| 2 | PpuM1 to BclI | residues 63–328 | 20 |
| 3 | PpuM1 to XmnI | residues 84–328 | 18 |
| 4 | PpuM1 to Sal I | residues 98–328 | 16 |
| 5 | DraI to AflII | residues 1–49 and 121–328 | 20 |
| 6 | BclI to AflII | residues 1–64 and 121–328 | 24 |
| 7 | XmnI to AflII | residues 1–86 and 121–328 | 26 |
| 8 | SalI to AflII | residues 1–99 and 121–328 | 27 |
| 9 | DraI to EcoR1 | residues 1–49 | 7 |
| 10 | BclI to EcoR1 | residues 1–64 | 11 |
| 11 | XmnI to EcoR1 | residues 1–86 | 13 |
| 12 | SalI to EcoR1 | residues 1–99 | 14 |
| 13 | HinfI to EcoR1 | residues 1–283 | 22 |
| 14 | AflIII to EcoR1 | residues 1–294 | 24 |
| 15 | BalI to EcoR1 | residues 1–304 | 25 |
| 16 | AflII to HinfI | residues 1–120 and 283–328 | 25 |
| 17 | AflII to AflIII | residues 1–120 and 294–328 | 23 |
| 18 | AflII to BalI | residues 1–120 and 303–328 | 22 |

Restriction sites used in AGM-27 for generating these chimeras are:

| | |
|---|---|
| DraI | nucleotides 4136–4141 |
| BclI | nucleotides 4181–4186 |
| XmnI | nucleotides 4245–4254 |
| SalI | nucleotides 4287–4292 |
| HinfI | nucleotides 4841–4845 |
| AflIII | nucleotides 4873–4878 |
| BalI | nucleotides 4901–4906 |
| PflM1 | nucleotides 4205–4215 |

All these sites, with the exception of PflM1, are present in the AGM-27 sequence but not in the HAV/7 sequence. These restriction sites are engineered at the analogous positions in the pHAV/7 2C gene by primer-directed mutagenesis using PCR. Fragments of pHAV/7 2C sequence are amplified by PCR using the primers with engineered restriction sites and the PCR products are then digested with the appropriate restriction enzymes and cloned into the pGR2 background. Where the restriction enzymes to be utilized in constructing the chimeras of the invention recognize multiple sites in the HAV/7 genome, one can subclone the 2C gene into a suitable vector prior to generation of the chimeras. Suitable vectors include, but are not limited to, plasmids, PUC vectors (Gibco-BRL), pCRII (Invitrogen), pGEM vectors (Promega) and pBS vectors (Stratagene).

Additional chimeras of the invention include chimeras 19–21, which are generated by substituting portions of the AGM-27 2C gene for the corresponding portion of the HAV/7 2C gene in, for example, the pGR1 construct.

| Chimera # | pGR2 Region Amplified | AGM-27 2C Amino Acid Sequence in Chimera | # AGM-27-specific 2C Amino Acid Residues in Chimera |
|---|---|---|---|
| 19 | PpuM1 to PflM1 | residues 1–70 | 12 |
| 20 | PflM1 to AflII | residues 74–120 | 5 |
| 21 | PflM1 to EcoR1 | residues 74–328 | 18 |

Chimeras 19–are constructed by engineering a PflM1 site into the AGM-27 2C gene. The appropriate segment of the pGR2 2C gene is then amplified by PCR using a primer with an engineered PflM1 restriction site and the resulting PCR product is digested with the appropriate enzymes and subcloned into the pGR1 background.

Since the HAV 2C gene encodes 335 amino acids, it is understood by those of ordinary skill in the art that the amino acid residues in the chimeras of the invention that are not from AGM-27 are from HAV/7. Thus for example, in chimera #19, 2C amino acids 1–70 are from AGM-27 and amino acids 71–335 are from HAV/7. In one embodiment the chimeras of the present invention encode at least one and no greater than thirty one of the AGM-27 2C amino acid residues which are different from the amino acids present in the corresponding amino acid sequence of HAV/7; in a more preferred embodiment, the chimeras encode between about 5 to about 25 of the AGM-27 2C amino acid residues which are different from the amino acids present in the corresponding amino acid sequence of HAV/7; and in a most preferred embodiment, the chimeras encode between about 10 to about 20 of the AGM-27 2C amino acid residues which are different from the amino acids present in the corresponding amino acid sequence of HAV/7.

In addition, the column marked "#AGM-27-specific 2C Amino Acid Residues in Chimera" indicates the number of AGM-27 2C amino acid residues present in the chimera which are different from the amino acid residues present in the corresponding amino acid sequence of HAV/7.

In an alternative embodiment, 2C chimeric genomes of the invention can be generated using fusion recombinant PCR techniques. For example, a fragment containing HAV/7 sequence corresponding to sequences upstream of the PpuM1 site to any nucleotide in the 2C gene can be generated by PCR amplification of HAV/7 plasmid DNA using appropriate primers. The reverse primer in this reaction would have 5'-add-on sequences corresponding to AGM-27 sequences just 3' to the gene fusion junction. Similarly, AGM-27 sequence corresponding to sequences from the desired gene fusion junction to sequences downstream of the EcoR1 restriction site near the 3' end of the 2C gene can be generated using plasmid pGR2 as a template. The forward primer in this reaction would have 5'-add-on sequences corresponding to HAV/7 sequences just 5' to the gene fusion junction. This primer can be the complement of the reverse primer used for amplification of the HAV/7 sequence. The products of these two PCR reactions would have overlapping sequence which would include the gene fusion junction. The overlapping sequence can be extended by a DNA polymerase to generate a product that is the sum of the two overlapping fragments (i.e. the 2C gene from 5' of the PpuM1 site to sequences just 3' of the EcoR1 site). This gene fusion PCR product can be amplified by standard PCR; the forward primer in this reaction may include the PpuM1 site and the reverse primer may include the EcoR1 site. The PCR amplified fragment containing the intact hybrid 2C gene would then be digested with PpuM1 and EcoR1 and subcloned into a modified HAV/7 clone (e.g. 32Y or pGR1 or pGR2). Using such gene fusion recombinant PCR techniques, chimeras which contain, for example, AGM-27 sequence from amino acid 90–328 (which includes 17 of the 31 amino acid differences in 2C between HAV/7 and AGM-27) or AGM-27 sequence from amino acid 267–328 (which includes 10 of the 31 amino acid differences in 2C between HAV/7 and AGM-27) can be generated.

Alternatively, chimeras containing different amounts of AGM-27 sequence at the amino-terminal end of the 2C protein can also be generated using similar techniques; in this case, the fragment containing the PpuM1 site would be amplified by PCR using pGR2 as a template and the fragment containing the EcoR1 site would be amplified using HAV/7 as a template. Of course, those of ordinary skill in the art would readily understand that the chimeras of the present invention could also be produced by other techniques common to molecular biology such as site-directed mutagenesis.

The present invention further relates to the production of 2C chimeric viruses from the nucleic acid sequences described herein.

In one embodiment, the 2C chimeric genomes of the invention can be inserted into an expression vector that functions in eukaryotic cells. Examples, of such vectors include, but are not limited to, plasmid expression vectors and vaccinia virus vectors.

The 2C chimeric genome contained in the recombinant expression vector can also be transcribed in vitro by methods known to those of ordinary skill in the art in order to produce RNA transcripts which encode the 2C chimeric hepatitis A viruses of the invention. The 2C chimeric hepatitis A viruses of the invention may then be produced by transfecting cells by methods known to those of ordinary skill in the art with either the in vitro transcription mixture containing the RNA transcripts or with the recombinant expression vectors containing the 2C chimeric genome. Such methods include, but are not limited to, electroporation, and lipofection and transfection with DEAE-dextran. Cells suitable for in vitro transfection with the RNA transcripts and recombinant expression vectors of the present invention include eukaryotic cell lines, cells put into primary culture from a host, or cells resulting from passage of the primary culture. Examples of preferred cells are MRC-5, AGMK, FRhK-4 and BSC-1 cells.

The 2C chimeric virus so generated can be tested for virulence phenotype by administering the 2C chimeric virus to tamarins and examining the livers of the tamarins for evidence of pathology and/or the serum for biochemical evidence of hepatitis as measured by levels of liver enzymes such as isocitrate dehydrogenase and alanine aminotransferase and the viruses can be tested for their growth in cell culture by techniques such as RIFA or slot blot hybridization as described in Examples section. The 2C chimeric viruses produced from the chimeric sequences of the invention may be purified or partially purified from the transfected cells by methods known to those of ordinary skill in the art such as those described in Andre et al. (*Prog. Med. Virol.,* (1990) 37:72–95) and Provost et al. (*J. Med. Virol.,* (1986) 19:23–20, both of which are hereby incorporated by reference. In a preferred embodiment, the 2C chimeric viruses are partially purified prior to their use as immunogens in the pharmaceutical compositions and vaccines of the present invention.

The present invention therefore relates to the use of 2C chimeric viruses as immunogens in live vaccines to prevent hepatitis A in a mammal. When used as a live vaccine, the 2C chimeric virus can be administered alone or in a suitable diluent such as saline or water. The vaccine of the invention may be administered to the mammal by a variety of routes including, but not limited to, orally, subcutaneously, intramuscularly or intravenously. A preferred route of administration is orally. Suitable amounts of chimeric hepatitis A virus may range from about approximately $10^3$ to about $10^8$ tissue culture infectious doses (TCID), more preferably, from about $10^4$ to about $10^7$ TCID. Those of ordinary skill in the art would readily understand that suitable concentrations of 2C chimeric virus to include in the vaccines of the invention will vary depending on the route of administration chosen. The immunogens of the invention may be administered once or at periodic intervals until a protective titer of anti-HAV antibody is produced.

In a preferred embodiment, the vaccine of the invention is administered to mammals selected from the group consisting of humans, apes and monkeys.

In an alternative embodiment, the immunogen of the present invention may be a nucleic acid sequence which encodes a 2C chimeric HAV. Where the sequence is a cDNA sequence, the cDNAs and their RNA transcripts may be used to transfect a mammal by direct injection into the liver tissue of the mammal (Emerson, S. U. et al. (1992) *J. Virol.*, 66:6649–6654, incorporated herein by reference).

Alternatively, direct gene transfer may be accomplished via administration of a eukaryotic expression vector containing a nucleic acid sequence of the invention.

Suitable routes of administration for a nucleic acid immunogen include, but are not limited to, intramuscular, subcutaneous or intradermal administration. Eukaryotic expression vectors suitable for producing high efficiency gene transfer in vivo are known to those of ordinary skill in the art and include, but are not limited to, plasmid-based expression vectors and retroviral and adenoviral vectors.

Doses of nucleic acid sequence effective to elicit a protective antibody response against hepatitis A range from about 250 µg to about 5 mg, more preferably from about 1 mg to 2 mg.

The 2C chimeric viruses and the nucleic acid sequences encoding these viruses may be supplied in the form of a kit, alone, or in the form of a pharmaceutical composition.

The administration to mammals of either the 2C chimeric genomes or the 2C chimeric viruses of the invention may be for either a prophylactic or therapeutic purpose. When provided prophylactically, the viruses or nucleic acid sequences are provided in advance of any exposure to HAV or in advance of any symptom due to HAV infection. The prophylactic administration therefore serves to prevent or attenuate any subsequent infection of the mammal with HAV. When provided therapeutically, the viruses or nucleic acid sequences are provided at, or shortly after, the onset of infection or disease caused by HAV. The therapeutic administration of the viruses or nucleic acid sequences of the invention thus attenuates the infection or disease.

In addition to use as a vaccine, the 2C chimeric genomes and 2C chimeric viruses of the invention can be used to prepare antibodies to HAV. These antibodies can be used directly as antiviral agents or they may be used in immunoassays such as ELISA, Western blotting and immunohistochemistry to detect HAV or HAV proteins.

The antibodies of the present invention may be contained in antiserum obtained from a mammal immunized with the 2C chimeric genomes or the 2C chimeric viruses of the invention. Alternatively the antibodies may be polyclonal antibodies purified or partially purified from the antiserum or monoclonal antibodies. The antibodies of the invention may be utilized for pre- or post-exposure passive immunity prophylaxis.

All articles or patents mentioned herein are hereby incorporated by reference. The following examples illustrate various aspects of the invention but are in no way intended to limit the scope thereof.

EXAMPLES

Materials and Methods

Cells

A subclone of the FRhK-4 cell line, 11-1, was used in these studies because growth of HAV in this cloned cell line is more efficient than in the parent cell line (S. U. Emerson, unpublished data). Cells were maintained in Dulbecco's modified Eagle medium (DMEM) supplemented with 10% fetal calf serum, glutamine, non-essential amino acids, 50 µg/ml gentamycin sulfate and 2.5 µg/ml amphotericin B (Fungizone) (10% DMEM).

Reverse Transcription, Polymerase Chain Reaction and DNA Sequencing

An AGM-27 virus stock consisting of 10% (w/v) liver homogenate in phosphate-buffered saline (pH 7.2) (Tsarev, A. A., et al. (1991) *J. Gen. Virol.*, 72:1677–1683) was the source of viral RNA for cloning of cDNA fragments generated by reverse transcription-polymerase chain reaction (RT-PCR). Briefly, RNA was isolated from 5–10 µl of liver homogenate by either the guanidinium isothiocyanate extraction procedure (Chomczymski, P. et al. (1987) *Anal. Biochem.*, 162: 156–159) or with Trizol reagent (Gibco-BRL, Bethesda, Md.) following the manufacturer's instructions. Glycogen (20 µg; Boehringer Mannheim, Indianapolis, Ind.) was added as a carrier prior to precipitation with isopropanol. The RNA was resuspended in 10 µl sterile water to which 1 µl of a 10 µM stock of reverse primer was added. The solution was heated at 65° C. for 3 minutes and cooled at room temperature for 5 minutes to facilitate primer binding to the template. The reverse transcription reaction was performed in a final volume of 20 µl in a reaction mixture consisting of 10 mM Tris-HCl (pH 8.4), 50 mM KCl, 2.5 mM $MgCl_2$, 40 U RNasin (Promega Biotech, Madison, Wis.), 1 mM of each deoxynucleoside triphosphate (dNTP) and 8 U avian myeloblastosis virus reverse transcriptase. After synthesis of cDNA at 42° C. for 60 minutes, PCR amplification was performed in a total volume of 100 µl of 10 mM Tris-HCl (pH 8.4), 50 mM KCl, 2.5 mM $MgCl_2$, 0.2 mM of each dNTP, 4 U Taq polymerase (Perkin-Elmer Corp, Norwalk, CT) and 0.5 mM each of forward and reverse primers. When necessary, silent mutations were incorporated into the primers to generate restriction enzyme sites required for subsequent cloning steps. PCR reaction consisted of 35 cycles of 1 minute of incubation at 94° C., 1 minute of incubation at 45° C. and 1–3 minutes of incubation at 72° C. followed by a single cycle at 72° C. for 10 minutes. A second round of PCR using nested primers was performed if necessary. The PCR products were purified from low melting agarose gels by phenol extraction or with a gel purification kit (Qiagen, Chatsworth, Calif.).

All PCR generated fragments or clones containing PCR generated DNA were sequenced using either Sequence (United States Biochemical Corp., Cleveland, Ohio) following the manufacturer's instructions or the Applied Biosystems 373A automated DNA sequencer using a modified Sanger method.

cDNA Clones

All nucleotide number assignments herein are based on the genomic map of wild-type HM-175 shown in FIG. 12 (which corresponds to FIG. 1 of Cohen et al. (1987) *J. Virol.*, 61:50–59). The pHAV/7 plasmid (Cohen, J. I., et al. (1987) *Proc. Natl. Acad. Sci.*, 84:2497–2501, the pHAV/7 plasmid was deposited with the American Type Culture Collection (ATCC) on August 7, 1987 and has ATCC accession number 67495) was modified by oligonucleotide-directed mutagenesis to include a PpuM1 site at nucleotide (nt) 3987–3993 (plasmid 32Y; S. U. Emerson and Y. K. Huang, unpublished results). In addition, HAV/7 has a naturally occurring EcoRI site at nucleotides 4977–4982 near the 3' end of the 2C gene. As this site was not present in the AGM-27 consensus sequence, an EcoRI site was engineered at the analogous position in the AGM-27 gene (T→C mutation at AGM nt 4982) by primer-directed mutagenesis using PCR. To facilitate cloning of intragenic chimeras in 2C, 32Y was further mutagenized using PCR (AUG mutation at nt 4358) to include an AflII site at nt 4353–4358 (plasmid pGRl). A natural AflII site is present at this position in the AGM-27 consensus sequence. The pGR2 chimera was generated by cloning the PpuM1-EcoRI fragment of the AGM-27 consensus sequence (AGM-27 genomic sequence is disclosed in SEQ. ID. NO:1 in U.S. Pat. No. 5,476,658; the AGM-27 virus was deposited with the ATCC on August 24, 1992 and has ATCC accession number VR 2380) (nt 3996–4981 of AGM-27 2C gene, which encodes amino acids 1–328 of the 2C gene) into the HAV/7 background of p32Y. The 2C gene of pGR2 had three nucleotide differences from the AGM-27 consensus sequence at positions 4211 (C to T transition), 4280 (G to A transition) and 4397 (T to C transition) but none changed the amino acid sequence. Because the EcoR1 site at nt 4977–4982 was used for cloning, the pGR2 plasmid contained a glutamic acid residue which is present in HAV/7 at amino acid position 331 in 2C instead of a lysine residue which is present in the AGM-27 consensus sequence. Thus, of the 31 amino acid differences between the 2C protein of AGM-27 and HAV/7, 30 are present in GR2.

The chimera pGR3 was generated by cloning the PpuM1-AflII fragment from plasmid pGR2 (AGM-27 2C nt sequence 3996–4357, which encodes amino acids 1–121 of the 2C gene) into pGR1. The chimera pGR4 was generated by cloning the AflII-EcoR1 fragment from plasmid pGR2 (AGM-27 2C nt sequence 4354–4981, which encodes amino acids 120–328 of the 2C gene) into pGR1. 17 and 13 of the 31 amino acid differences between the 2C proteins of AGM-27 and HAV/7 are present in GR3 and GR4, respectively.

Similarly, the PpuM1-AflII or AflII-EcoR1 segments of pGR2 were replaced with wild-type HM-175 sequences to generate clones pGR14 and pGR13, respectively (FIG. 1). The pGR15 clone contained AGM-27 sequence of 2B from nt 3758–3988. The pGR9 plasmid contained the truncated AGM-27 2B sequence and 2C sequences from nt 3758–4981 in the HAV/7 background (FIG. 1).

Establishment of Virus Stocks

All full-length cDNAs were cloned in PGEM1 (Promega Biotech). In vitro transcription and transfection assays were performed as described previously by Emerson et al. (Emerson, S. U., et al. (1991) *J. Virol.,* 65:4882–4886) with a few modifications. Briefly, Sp6 polymerase (Promega Biotech) transcripts synthesized from 5 $\mu$g of DNA linearized with HaeII were transfected without purification into 11-1 cells. Transfection of cells was accomplished by the DEAE-dextran method. One week after transfection, half of the cells in each flask were passaged to coverslips and the fraction of cells which contained viral antigen was estimated by immunofluorescence microscopy (Emerson, S. U., et al. (1991) *J. Virol.,* 65:4882–4886). Transfected cells were harvested by trypsinization when >80% of the cells were infected. Viruses were released from the harvested cells by at least three cycles of freeze-thawing to generate the working virus stocks.

Radioimmunofocus Assay (RIFA)

RIFA was used to determine focus size of different chimeric viruses and to quantify virus titers. RIFA was a modification of that described by Lemon et al. (1983) (*J. Clin. Microbiol.,* 17:834–839) and Anderson et al. (1987) ("Positive Strand RNA Viruses" MA Brinton and RR Reichert (ed.) AR Liss Inc. NY) and was essentially performed as previously described (Funkhouser, A. W., et al. (1994) *J. Virol.,* 68:148–157). Cells (11-1) were grown on Thermolux round 25 mm coverslips fixed to the bottom of each well in 6-well plates. Virus was adsorbed to cells for 2–4 hours at 34.5° C. in a $CO_2$ incubator.

Infected cells were overlaid with 5 ml of 0.5% agarose medium and incubated at 34.5° C. in a $CO_2$ incubator for 10 days. Cells were fixed with acetone and were either processed immediately or stored at -20° C. Viral antigen was detected with a primary antibody consisting of chimpanzee hyperimmune serum (S. U. Emerson, unpublished results) and a secondary antibody of $^{125}$I-labelled sheep anti-human IgG F(ab')$_2$ fragment (Amersham Corporation, Arlington Heights, Ill.). Foci were visualized by autoradiography.

Growth Curve Assays

Growth curve assays were performed to evaluate the relative rates of replication of viruses in 11-1 cells. Cell monolayers which were >80% confluent in 96-well plates (Falcon) were infected with 0.2 ml of virus diluted in 10% DMEM at a multiplicity of infection of 6 radioimmunofocus-forming units (RFU) per cell. Cells were incubated with virus for 2–4 hours at 34.5°C. in a $CO_2$ incubator after which the cells were washed 4 times with 10DMEM and overlaid with 0.2 ml 10% DMEM. At various times, the medium overlaying the cells, which contained virus released from cells, was removed and saved and the volume was adjusted to 0.3 ml with 10i DMEM. The adherent cells in the wells were washed once with 0.2 ml trypsin solution at room temperature and were subsequently incubated with 0.1 ml trypsin solution at 34.5° C. until the cells exhibited a rounded morphology. The trypsinized cells were then harvested by vigorous pipetting and combined with the medium that had been previously removed. The total virus sample (0.4 ml) was stored at −80° C. Cells were lysed by at least three cycles of freeze-thawing and virus was quantified either by slot blot hybridization or by RIFA. Either HAV/7 or a modified clone of HAV/7 containing a silent mutation was used as a standard in these experiments to measure growth of the fully cell culture-adapted virus. Since there was no significant difference in the growth properties of these two viruses, they were used interchangeably and for simplicity, are always referred to as HAV/7 in this study.

Slot Blot Hybridization

RNA was isolated from growth curve samples using Trizol reagent (Gibco-BRL) according to the manufacturer's instructions with the following modifications: A 130 $\mu$l aliquot of sample was extracted with an equal volume of Trizol. After the 15 minute centrifugation step to separate the aqueous and organic phases, 100 $\mu$l of the aqueous phase was removed and added to 320 $\mu$l of a 1:1 solution of 10×SSC (1×SSC is 0.15 M NaCl and 0.015 M sodium citrate (pH 7.0)) and formaldehyde. Viral RNA was quantified by slot blot analysis using a negative strand $^{32}$p- labelled RNA probe spanning the complete HAV/7 genome. Hybridization was at 50° C. for at least 16 hours. Blots were washed three times for 30 minutes each with 2×SSPE (1×SSPE is 10 mM sodium phosphate, 0.18 M NaCl, 1 mM EDTA (pH 7.4)) with 0.1% sodium dodecyl sulphate (SDS) at room temperature and once with 0.1×SSPE, 0.1% SDS at 64° C. for one hour. Autoradiography was performed and a Deskscan II scanner (Hewlett Packard) with NIH Image analysis package (Wayne Rasband, public domain software, Bethesda, Md.) was used to quantify viral RNA from each time point in the growth curve. At least two or more sister clones were assayed for each virus construct.

Virulence Studies in Tamarins

The ability of AGM-27 2C chimeras GR2, GR3 and GR4 to cause disease in tamarins was evaluated. Each of two tamarins for each chimera was inoculated intravenously with approximately $10^{3.8}$ tissue culture infectious dose equivalents of the GR2 virus in a 0.5 ml volume of inoculum or with approximately $10^{4.8}$ tissue culture infectious dose equivalents of the GR3 or GR4 viruses in a 0.5 ml volume of inoculum. The estimated number of genome equivalents in the inoculum was determined by RIFA. Blood samples were collected and needle liver biopsies were performed weekly on each animal for at least 2 weeks before and 16 weeks after inoculation with virus. The blood samples were analyzed for seroconversion to anti-HAV with a commercial assay (Abbott Laboratories, North Chicago, Ill.) and for serum alanine amino transferase (ALT) and isocitrate dehydrogenase (ICD) levels with standard techniques (Metpath, Rockville, Md.). Histopathology was determined under code and scored on a scale of 1 to 4 depending on the severity of the hepatitis; 1 corresponded to mild hepatitis and 4 to severe hepatitis.

Stool samples from the GR2, GR3 or GR4-inoculated tamarins were also analyzed for the presence of excreted virus by RT-PCR. Briefly, a 10% (w/v) suspension of stool in 10 mM Tris (pH 7.0) and 0.135 M NaCl was prepared in a and clarified by low-speed centrifugation to remove large particulate matter. Viral RNA was extracted from a 100 μl aliquot of clarified sample with 1 ml of Trizol reagent (Gibco-BRL) following the manufacturer's instructions and RT-PCR was performed to amplify a specific region of the viral genome. The amplified DNA was purified with a PCR fragment purification kit (Qiagen) and was sequenced to determine the identity of the excreted virus.

Virulence Studies In Chimpanzees

Two chimpanzees each were inoculated intravenously with approximately $10^5$ tissue culture infectious dose equivalents of either the GR4 or GR2 virus in a 0.5 ml volume of inoculum. Blood samples were collected and needle liver biopsies were performed weekly on each animal for at least 2 weeks before and 16 weeks after inoculation with virus. The blood samples were analyzed for seroconversion to anti-HAV with commercial assay and for serum alanine amino transferase (ALT) and isocitrate dehydrogenase (ICD) levels. Histopathology was determined under code and scored on a scale of 1 to 4 as for the tamarins.

The housing, maintenance, and care of all animals met or exceeded all requirements for primate husbandry.

Example 1

Construction of Chimeras between AGM-27 and HM-175

Figure 2:
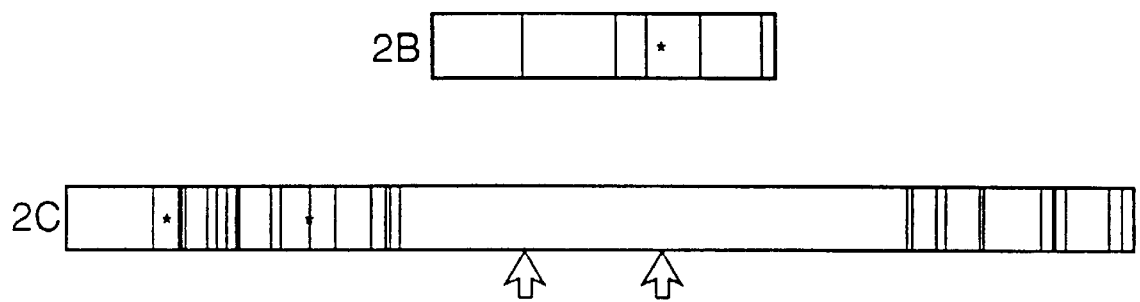
FIG. 2 presents a schematic diagram showing the amino acid sequence differences in the proteins between wild-type HM-175 and AGM-27. The bars mark positions at which the amino acid sequence differs between AGM-27 and wild-type HM-175. There are 30 amino acid differences between the 2C sequences of wild-type HM-175 and AGM-27. Cell culture adaptation of HM-175 to produce HAV/7 resulted in three amino acid changes in 2C at residues 31, 76 and 190. When the comparison is between HAV/7 and AGM-27, there are 31 amino acid differences. Amino acid residues 31 and 190, which are the same in wild-type HM-175 and AGM-27, differ between HAV/7 and AGM-27. Amino acid residue 76, which differs between wild-type HM-175 and AGM-27, is the same in HAV/7 and AGM-27. The asterisks mark the sites of the three mutations that are critical for growth of HAV/7 in cell culture (nts 3889 in 2B and 4087 and 4222 in 2C) (Emerson, S. U., et al. (1992) *J. Virol.,* 66:650–654). The locations of the two conserved putative NTP-binding motifs are shown with arrows. The amino acid sequence differences in 2C between HM-175 (either wild-type or HAV/7) and AGM-27 are clustered at the amino-terminal and carboxy-terminal ends of the protein. The mutation at position 3889 in the 2B gene, which greatly enhances the growth of human HAV in cell culture, is absent in AGM-27.

The 2B and 2C gene products are the most important determinants of efficient growth of HAV in cell culture (Emerson, S. U., et al. (1992) *J. Virol.,* 66:650–654). Chimeras containing the AGM-27 truncated 2B and/or 2C gene in the background of the cell culture-adapted HM-175 virus genome were constructed as described in the methods section and are shown schematically in FIG. 1. The 2C gene was further subdivided and intragenic chimeras between the simian and human 2C genes were generated (FIG. 1, GR3 and GR4). The amino acid sequence differences between the HM-175 (for either wide-type or HAV/7) and AGM-27 2C proteins are clustered at the amino-terminus and carboxy-terminus of the protein (FIG. 2). The intragenic 2C chimeras were constructed in order to evaluate the effect of separating the two clusters of amino acid residues at the ends of the 2C protein, which differ between HM-175 and AGM-27, from each other. Results obtained with these chimeras are described in the following Examples.

Example 2

RIFA of HAV/7, AGM-27 and the GR2 Chimera

Figure 3:
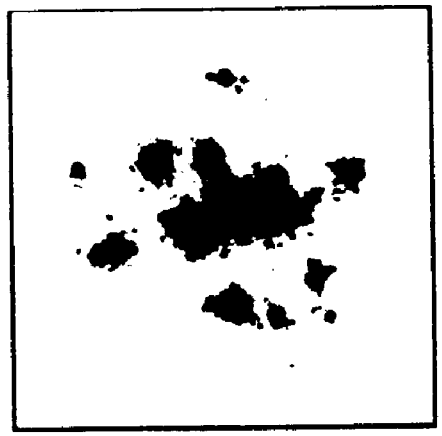
FIG. 3 shows the results of a radioimmunofocus assay comparing the sizes of the foci formed by HAV/7, AGM-27 and the GR2 chimera which contains the AGM-27 2C sequence in the HAV/7 background.
Figure 3:
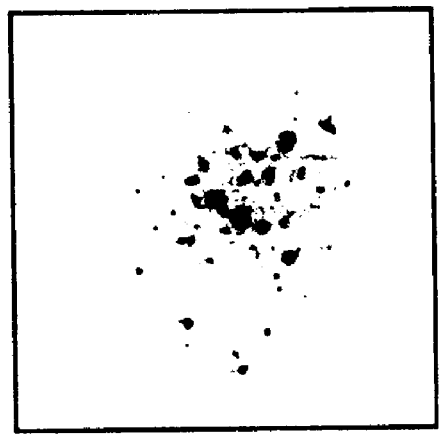
Figure 3:
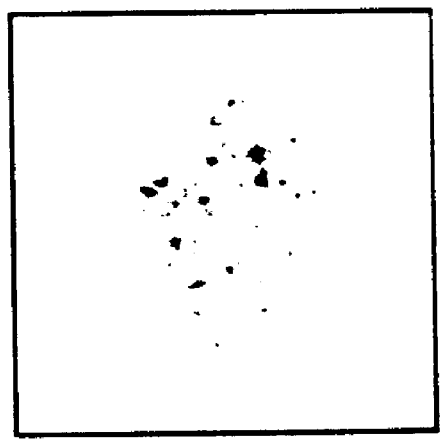

The radioimmunofocus assay is one method which can be used to evaluate the relative growth properties of viruses. The cell culture-adapted HM-175 virus (HAV/7) grew well in cell culture and formed large foci (FIG. 3). AGM-27, which is a wild-type virus, clearly grew in cell culture but had a small focus phenotype (FIG. 3). By comparison, wild-type HM-175 grew so poorly that visible foci were not detected by this assay (data not shown). Replacement of the HAV/7 2C gene with AGM-27 sequences (chimera GR2) drastically reduced the ability of the virus to grow (FIG. 3). The only differences between HAV/7, which formed large foci, and the chimera GR2, which had a small focus phenotype, are in the 2C gene, demonstrating the significant contribution of the sequences in 2C to growth of HAV in cell culture.

Example 3

RIFA of HAV/7 and Chimeras GR2, GR3, GR4. GR15 and GR9

Replacement of the 2C gene of HAV/7 with AGM-27 sequences drastically reduced the size of the foci that were formed (FIG. 4B). The simian-human intragenic 2C chimeras GR3 and GR4 formed intermediate sized foci (FIGS. 4C and 4D). Replacement of the HAV/7 truncated 2B gene with AGM-27 sequences decreased the size of the foci only slightly, if at all (FIG. 4E). However, a chimera containing both the AGM-27 truncated 2B gene and 2C gene in the HAV/7 background formed foci that were even smaller (FIG. 4F) than those formed by the chimera containing only the AGM-27 2C gene, again demonstrating the negative influence of the AGM-27 truncated 2B sequence in the context of the homologous 2C.

Example 4

Kinetic Studies Showing Relative Growth Rates of HAV/7 and the Chimeras

Figure 5:
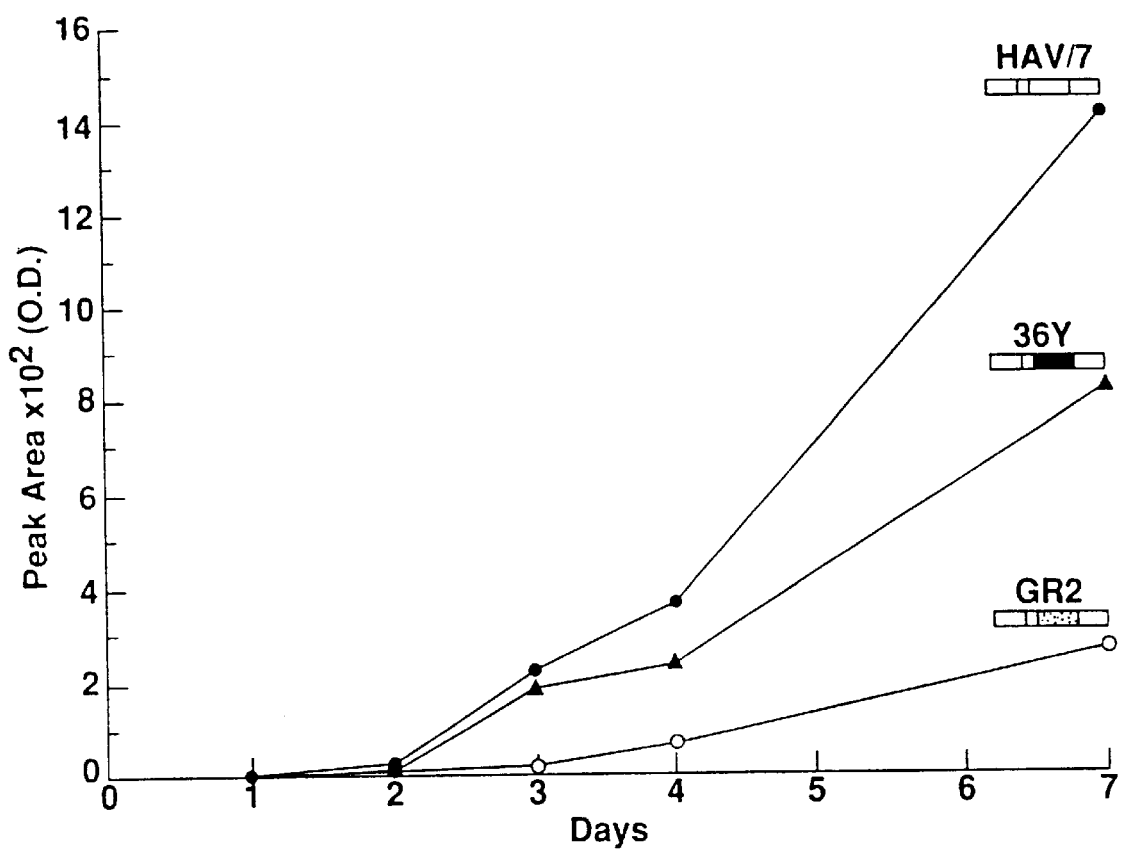
FIG. 5 shows a hybridization assay comparing the growth rates of HAV chimeras which differ only in the sequence of the 2C gene. The chimeras contained either the cell culture-adapted HM-175 (HAV/7), wild-type HM-175 (36Y) or AGM-27 2C sequence in the HAV/7 background (GR2). Viral RNA was quantified by slot blot hybridization followed by autoradiography and densitometry analysis. In the bar diagram identifying the virus genotype, AGM-27 sequences are shaded in grey and the four boxes shown in each diagram indicate from left to right (5'→3'): HAV/7 genomic sequence 5' of the truncated 2B gene, truncated 2B gene, 2C gene and HAV/7 genomic sequence 3' of the 2C gene. The demarcations of the truncated 2B gene and of the 2C gene as shown in the bar diagrams are not drawn to scale.

Kinetic studies were conducted as a quantitative measure of the relative growth efficiencies of HAV/7 and the chimeric viruses. Cells were infected with a high multiplicity of virus (6 radioimmunofocus units (RFU)/cell) to ensure that almost every cell was infected. Increase in virus titer over time was therefore a measure of virus replication. RNA was extracted from samples harvested at each time point and quantified by slot blot hybridization and densitometry. Comparison of growth of HAV/7 with a chimera containing the AGM-27 2C gene in this same background (GR2) shows that consistent with the small focus phenotype for GR2 shown previously (FIG. 3) the AGM-27 2C sequences greatly reduced the ability of the virus to grow (FIG. 5). Substitution of the cell culture-adapted 2C gene with that from the wild-type human virus also reduced the growth potential of the virus (36Y)

although not as drastically as that observed with the simian-human chimera (FIG. 5). The relative rates of growth of HAV/7 and the 2C chimeras as measured by RIFA were similar to that observed by slot blot analysis (data not shown). Both assays were performed for most chimeras studied and there consistently was good correlation between the results obtained by the two assays.

Figure 6:
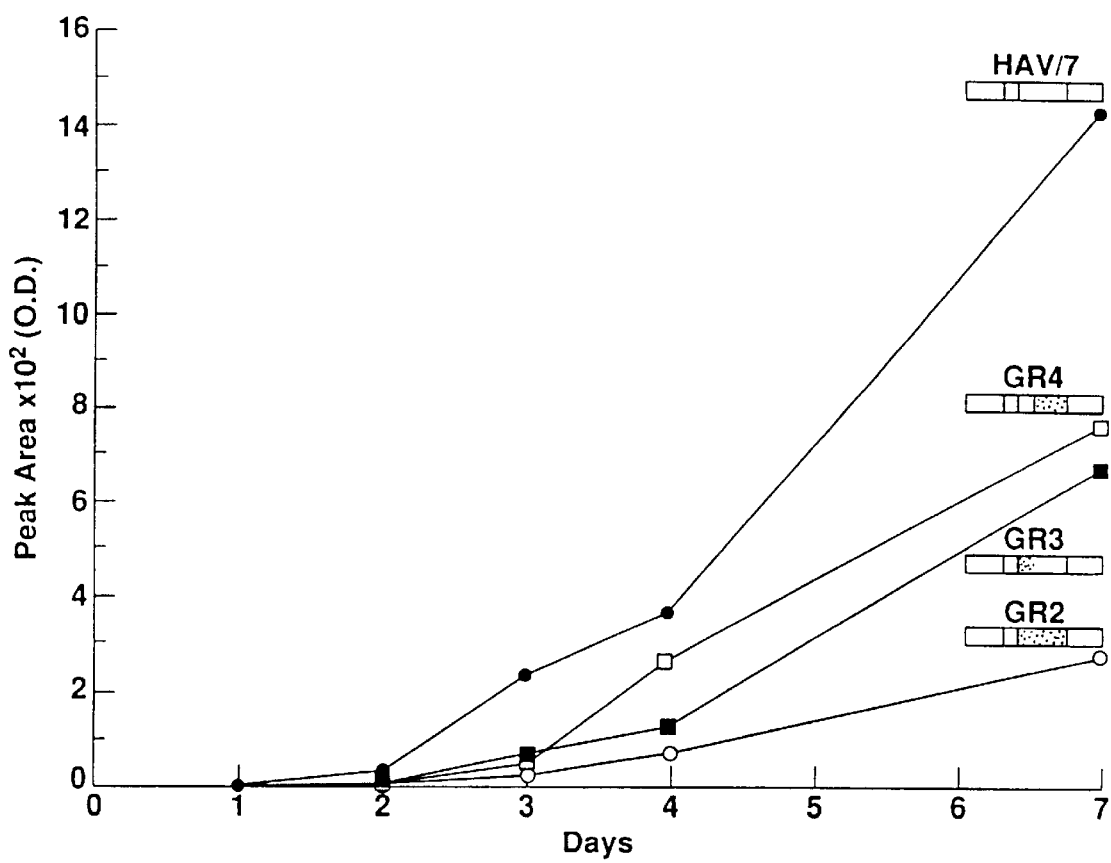
FIG. 6 shows results of a hybridization assay of growth curves of HAV/7, the simian-human chimera GR2, and the intragenic 2C chimeras, GR3 and GR4. Viral RNA was quantified by slot blot hybridization followed by autoradiography and densitometry analysis. In the bar diagram identifying the virus genotype, AGM-27 sequences are shaded in grey and the four boxes shown in each diagram indicate from left to right (51'→3'): HAV/7 genomic sequence 5' of the truncated 2B gene, truncated 2B gene, 2C gene and HAV/7 genomic sequence 3' of the 2C gene. The demarcations of the truncated 2B gene and of the 2C gene as shown in the bar diagrams are not drawn to scale.

Kinetic assays were also performed to evaluate the ability of the intragenic 2C chimeras to grow in cell culture. Quantitation was again by slot blot hybridization and densitometry. Chimeras containing AGM-27 sequences in either half of 2C (GR3 and GR4) had an intermediate growth phenotype (FIG. 6) as they grew less well than HAV/7 but better than the chimera containing the entire AGM-27 2C sequence (GR2). These data demonstrate that the clusters of amino acid residues that are unique to AGM-27 at either end of the 2C protein have a negative effect on growth and that this effect is additive. Growth of the GR4 chimera was especially sensitive to the status of the cells and GR4 grew at a rate slightly greater or less than that of the GR3 chimera in different experiments. In every case however, it grew significantly less well than did HAV/7. Kinetic studies were also performed with chimeras containing wild-type HM-175 sequence in one half and AGM-27 sequences in the other half of 2C in the HAV/7 background (GR13 and GR14; FIG. 1). These chimeras grew but not as well as the analogous chimeras containing HAV/7 sequences instead of wild-type HM-175 sequence (data not shown), again emphasizing the importance of the mutations in 2C that were acquired during passage of HM-175 in cell culture.

Figure 7:
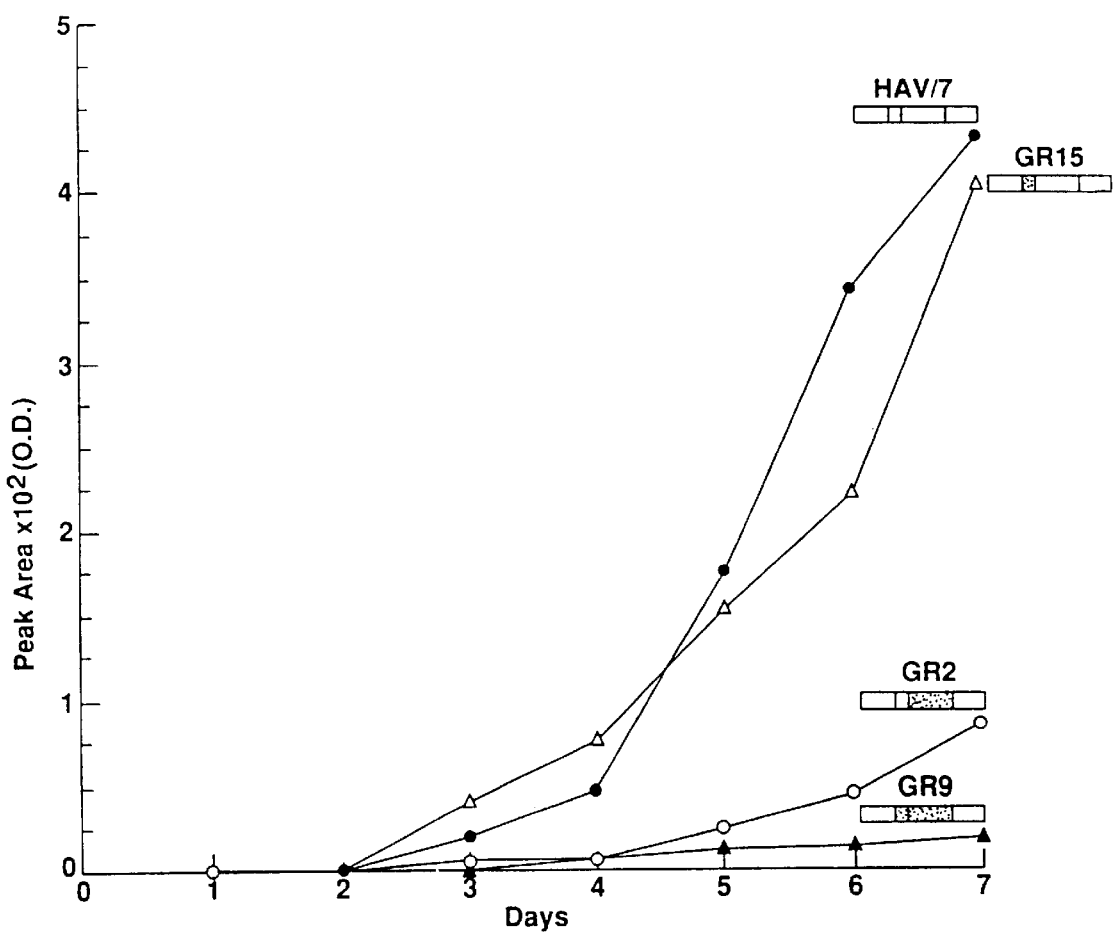
FIG. 7 shows the results of a hybridization assay of growth curves of HAV/7 and chimeras containing the truncated AGM-27 2B gene (GR15), the 2C gene (GR2) or the truncated 2B gene and the 2C gene (GR9) in the HAV/7 background. Viral RNA was quantified by slot blot hybridization followed by autoradiography and densitometry analysis. In the bar diagram identifying the virus genotype, AGM-27 sequences are shaded in grey and the four boxes shown in each diagram indicate from left to right (5'→3'): HAV/7 genomic sequence 5' of the truncated 2B gene, truncated 2B gene, 2C gene and HAV/7 genomic sequence 3' of the 2C gene. The demarcations of the truncated 2B gene and of the 2C gene as shown in the bar diagrams are not drawn to scale.

The truncated AGM-27 2B gene by itself in the HAV/7 background (GR15) had only a minor effect, if any, on virus growth (FIG. 7). However in conjunction with the homologous 2C (GR9), the truncated AGM-27 2B gene consistently had a significant negative effect on virus growth (FIG. 7). The results of the kinetic studies presented in FIGS. 5–7 were consistent with the relative sizes of the foci observed for the different chimeric viruses. Moreover, the RIFA and kinetics studies demonstrated that the 2C gene is a major determinant of the efficiency of growth in cell culture and that the AGM-27 2C gene significantly decreases the ability of HAV/7 to grow in cell culture. In addition, the fact that the intragenic chimeras GR3 and GR4 are viable and grow at intermediate levels suggests that each cluster of sequence differences present at the ends of the 2C gene in AGM-27 has a negative effect on growth.

Example 5

Virulence Studies in Tamarins of the Chimeras GR2, GR3 and GR4

AGM-27 is virulent in tamarins but attenuated in chimpanzees (Emerson, S. U., et al. (1996) *J. Infect. Dis.,* 173:592–597) while HAV/7 has an attenuated phenotype in tamarins (Cohen, J. I., et al. (1989) *J. Virol.,* 63:5364–5370). The GR2, GR3 and GR4 chimeras were each inoculated into two tamarins intravenously and serum liver enzyme levels, antibody titers and liver pathology were evaluated. The pattern of changes in ICD and ALT levels during the course of infection of all animals were similar.

Figure 8A:
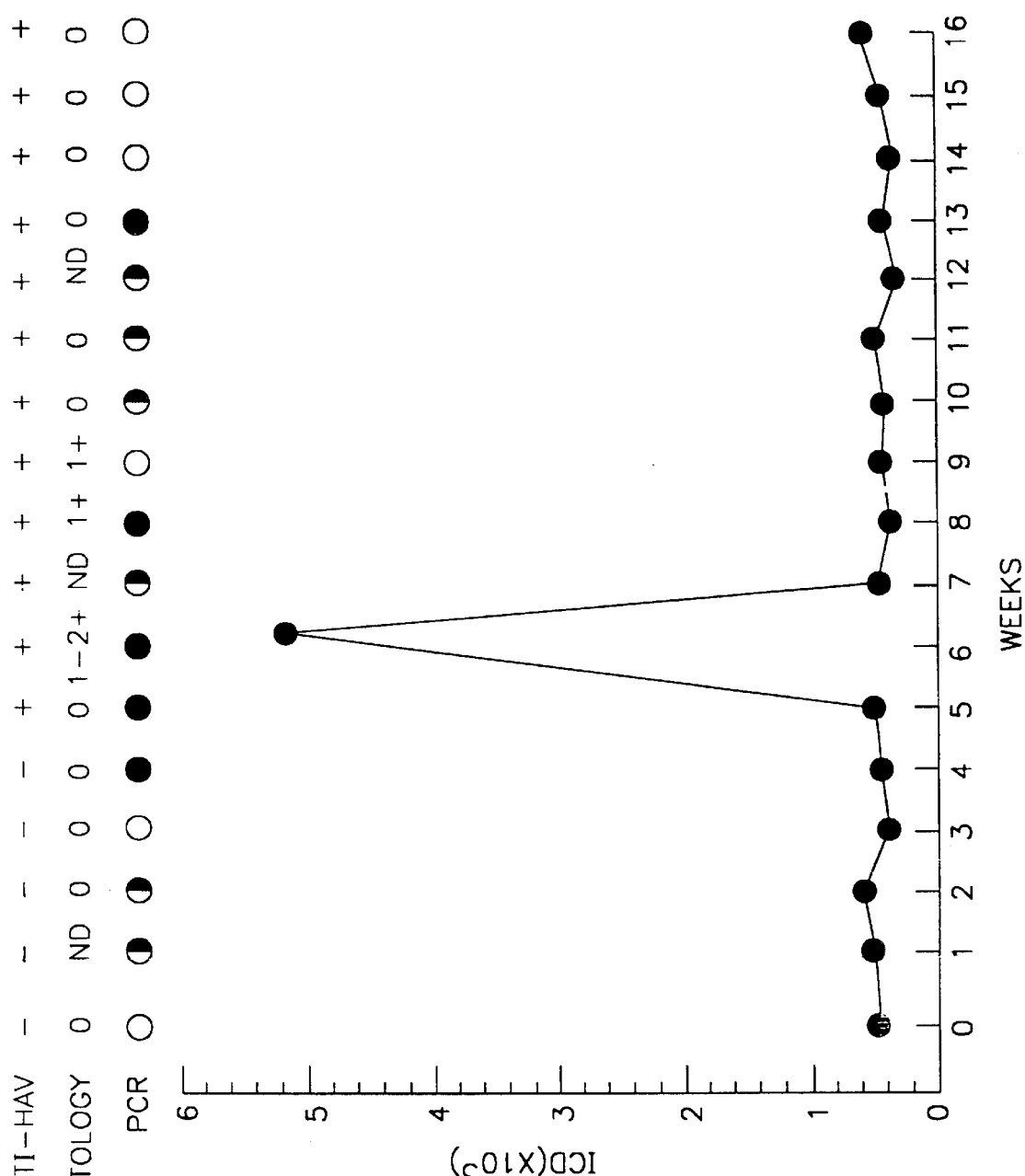
FIGS. 8A and 8B show biochemical (ICD levels), serological (anti-HAV), histopathological and PCR analyses of two tamarins 782 (FIG. 8A) and 783 (FIG. 8B) inoculated with the GR2 chimera which contains the AGM-27 2C gene in the HAV/7 background. The ICD serum enzyme levels were measured in international units per ml (IU/ml). A + in the row marked "anti-HAV" indicates samples that were positive for anti-HAV antibodies as determined by commercial assay. The histopathology scores correspond to mild hepatitis (1+), mild to moderate hepatitis (2+), moderately severe hepatitis (3+) and severe hepatitis (4+). The "ND" designation signifies that liver histology analysis was not performed for these samples. For the PCR analyses, an open circle indicates that the stool sample analyzed was completely negative for HAV after two steps of nested PCR; a half-closed circle indicates that the stool sample was positive for HAV after two steps of nested PCR and a closed circle indicates that the stool sample was positive for HAV after one step of PCR.
Figure 8B:
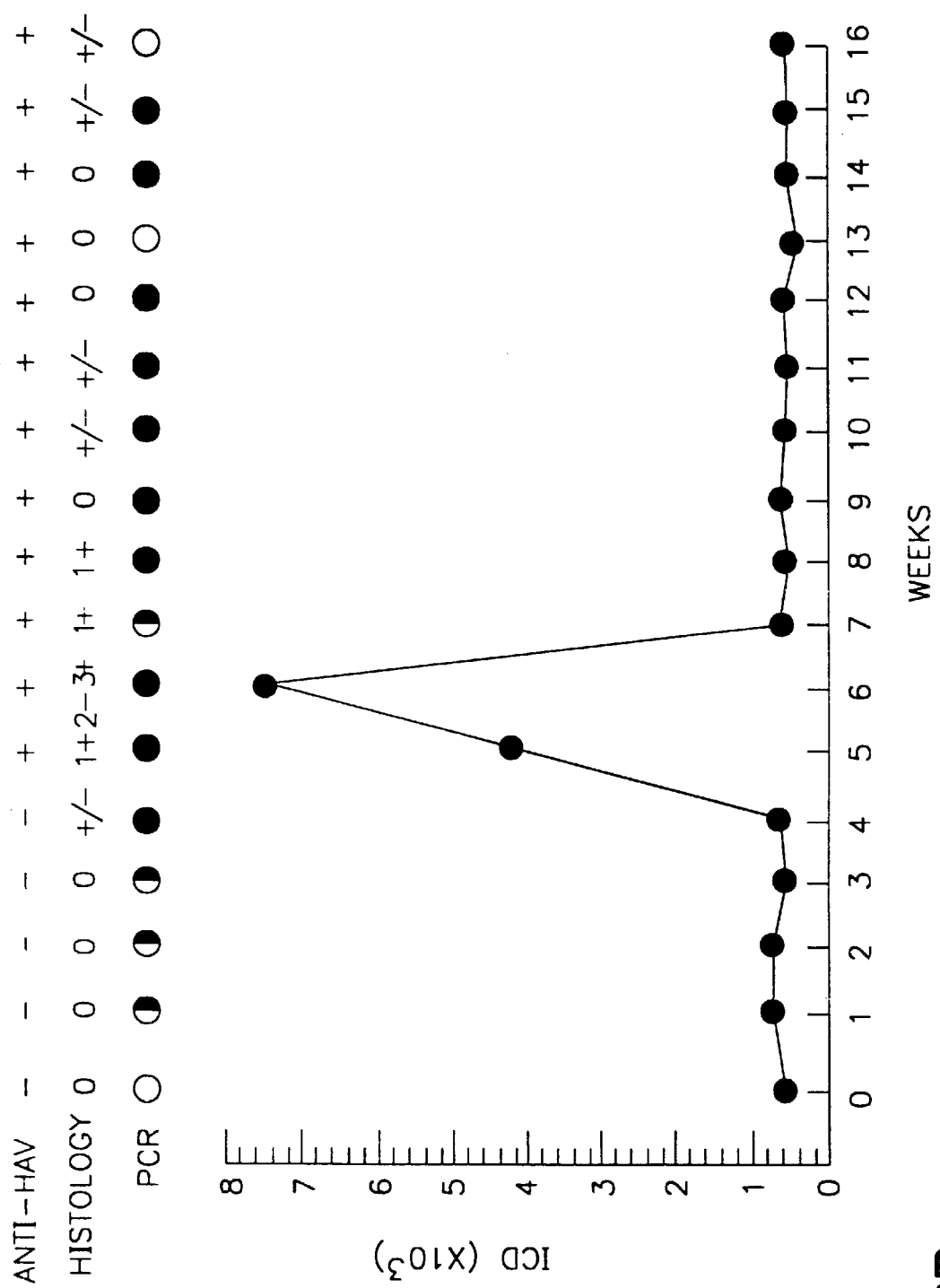

The results presented in FIGS. 8A and 8B show that the GR2 chimera was virulent in tamarins, causing significant increases in serum liver enzyme levels and seroconversion for HAV by week 5 after inoculation. Liver histology showed mild (1+) to moderate (2+) hepatitis 6–9 weeks after inoculation in one animal (FIG. 8A) and mild (1+) to moderately severe (3+) hepatitis 5–8 weeks after inoculation in the second animal (FIG. 8B). Virus specific RT-PCR amplification of fecal samples from weeks 5, 6 and 7 were positive either after one round (weeks 5 and 6) or after two rounds (week 7) of PCR with nested primers. A significant amount of virus was therefore being excreted concurrent with the peak elevation of liver enzyme values in the serum and seroconversion in the animals. Partial sequence analysis of virus genomes amplified from the stool samples showed that the sequence of the excreted virus was the same as that of the chimeric virus in the inoculum. These results demonstrate that the 2C gene of AGM-27 can confer the phenotype of virulence for tamarins to an otherwise attenuated virus (HAV/7).

Figure 9A:
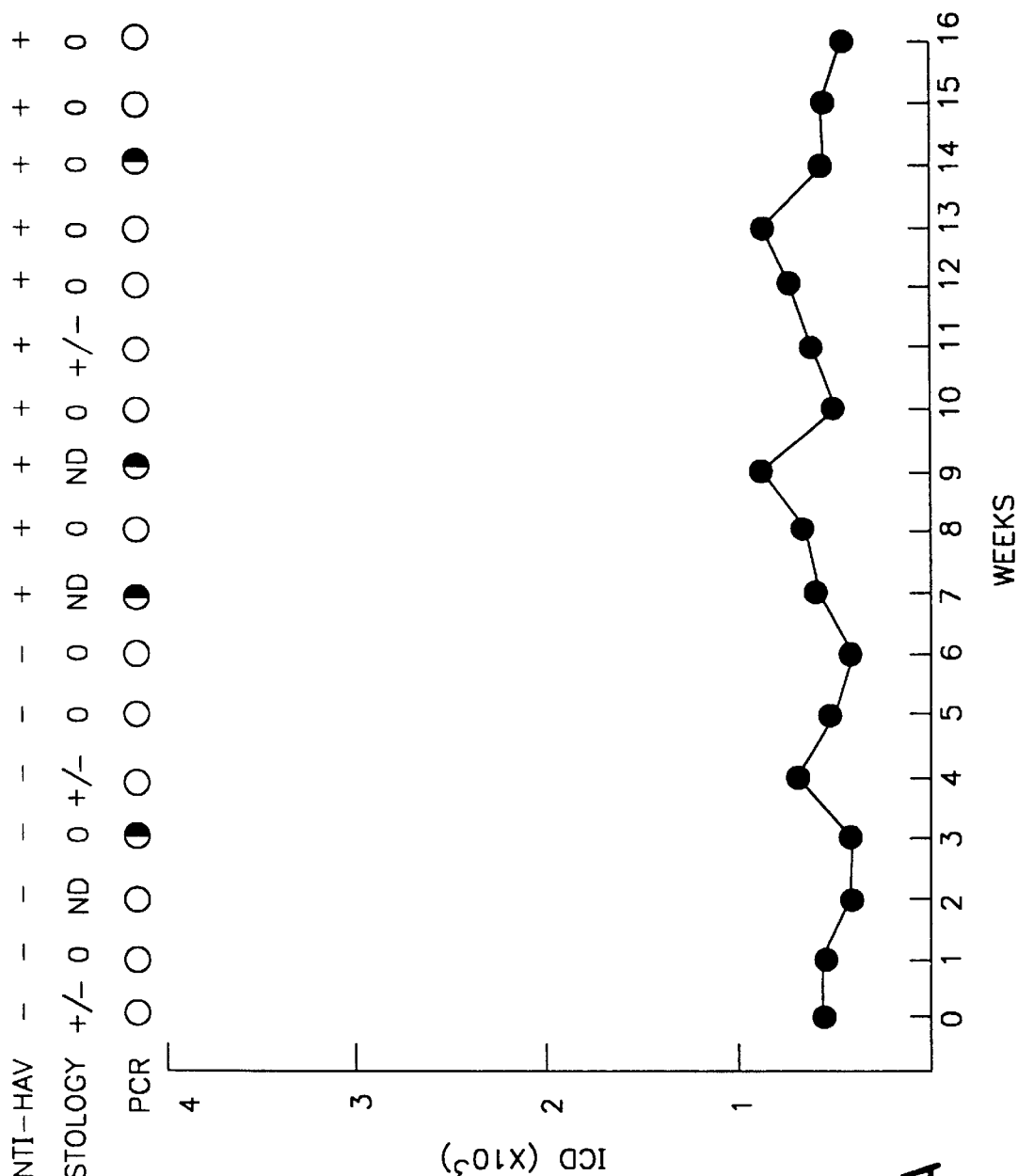
FIGS. 9A and 9B show biochemical (ICD levels) serological (anti-HAV), histopathological and PCR analyses of two tamarins, 808 (FIG. 9A) and 790 (FIG. 9B), inoculated with the GR3 chimera which contains sequence from nt 3996–4357 of the AGM-27 2C gene in the HAV/7 background. The ICD serum enzyme levels were measured in international units per ml (IU/ml). A + in the row marked "anti-HAV" indicates samples that were positive for anti-HAV antibodies as determined by commercial assay. The "ND" designation signifies that liver histology analysis was not performed for these samples. For the PCR analyses, an open circle indicates that the stool sample analyzed was completely negative for HAV after two steps of nested PCR; a half-closed circle indicates that the stool sample was positive for HAV after two steps of nested PCR and a closed circle indicates that the stool sample was positive for HAV after one step of PCR.
Figure 9B:
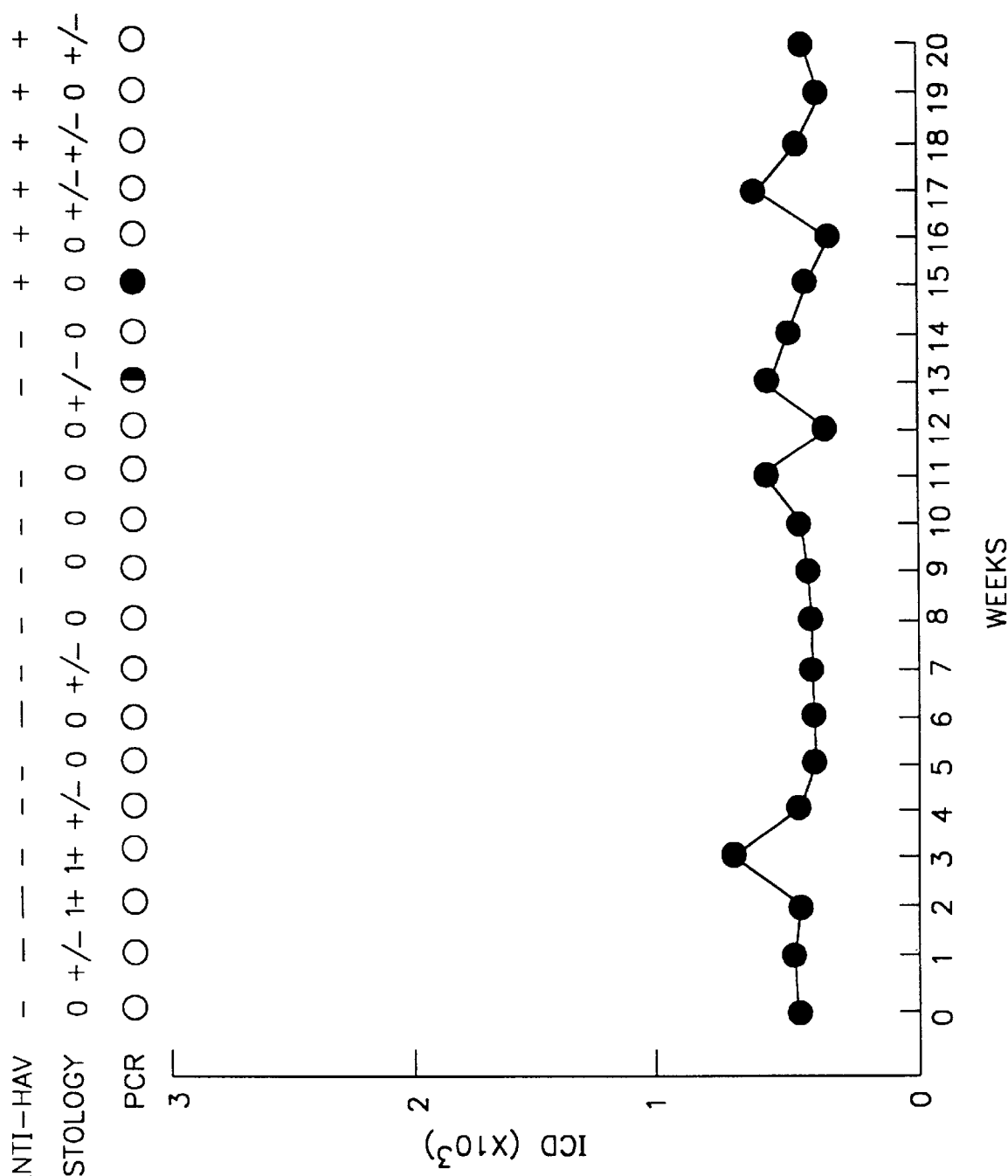

Tamarins inoculated with a chimera containing AGM-27 sequence in the 5' half of the 2C gene in the HAV/7 background (GR3) showed no significant increase in serum liver enzyme levels in either animal (FIGS. 9A and 9B). Seroconversion occurred 7 weeks after inoculation in one animal (FIG. 9A) but the level of anti-HAV antibodies was relatively low. There was seroconversion in the second animal in week 15. (FIG. 9B).

Figure 10A:
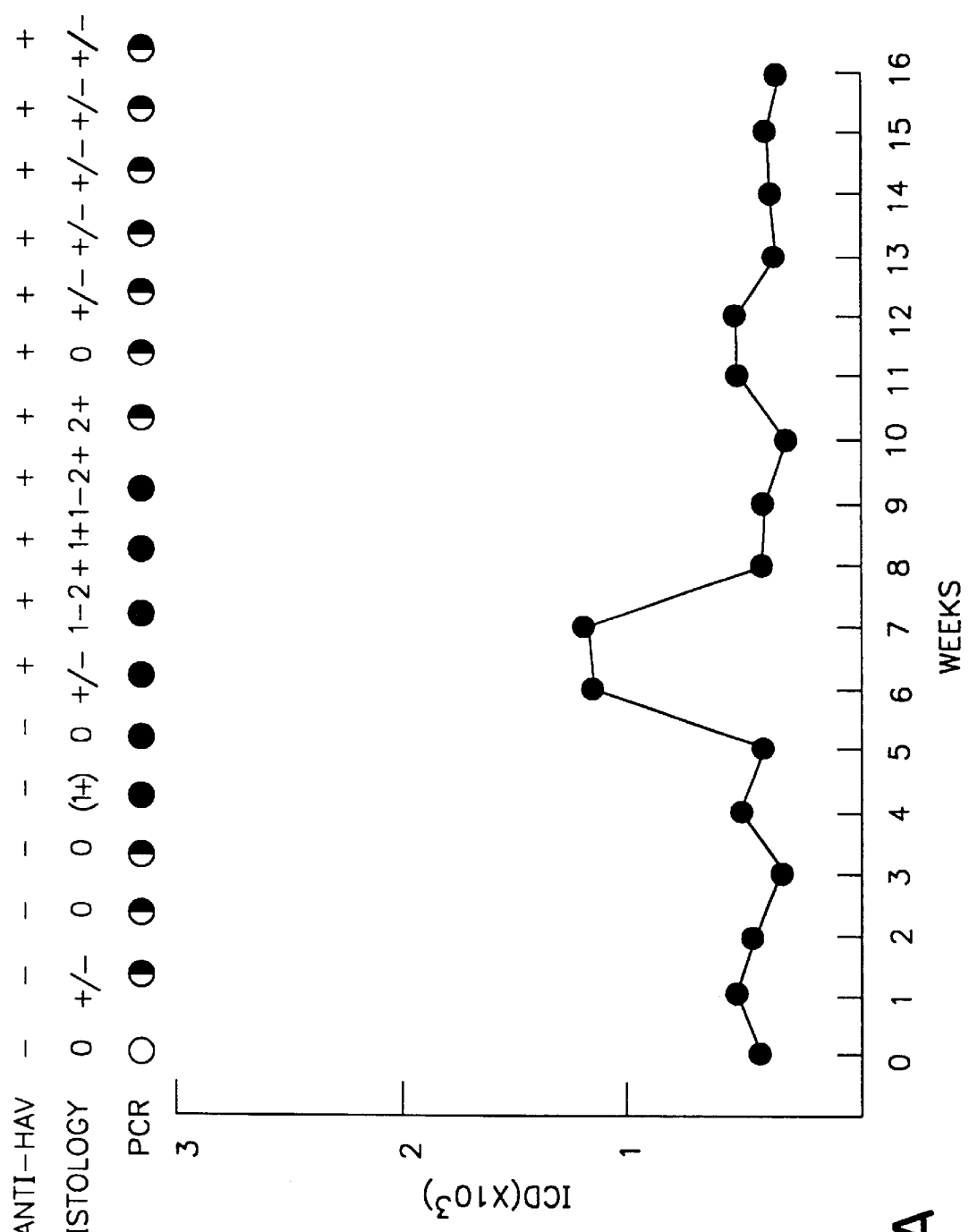
FIGS. 10A and 10B show biochemical (ICD levels), serological (anti-HAV), histopathological and PCR analyses of two tamarins, 799 (FIG. 10A) and 818 (FIG. 10B), inoculated with the GR4 chimera which contains sequence from nt 4354–4981 of the AGM-27 2C gene in the HAV/7 background. The ICD serum enzyme levels were measured in international units per ml (IU/ml). A + in the row marked "anti-HAV" indicates samples that were positive for anti-HAV antibodies as determined by commercial assay. The histopathology scores correspond to mild hepatitis (1+), mild to moderate hepatitis (2+), moderately severe hepatitis (3+) and severe hepatitis (4+). The "ND" designation signifies that liver histology analysis was not performed for these samples. For the PCR analyses, an open circle indicates that the stool sample analyzed was completely negative for HAV after two steps of nested PCR; a half-closed circle indicates that the stool sample was positive for HAV after two steps of nested PCR and a closed circle indicates that the stool sample was positive for HAV after one step of PCR.
Figure 10B:
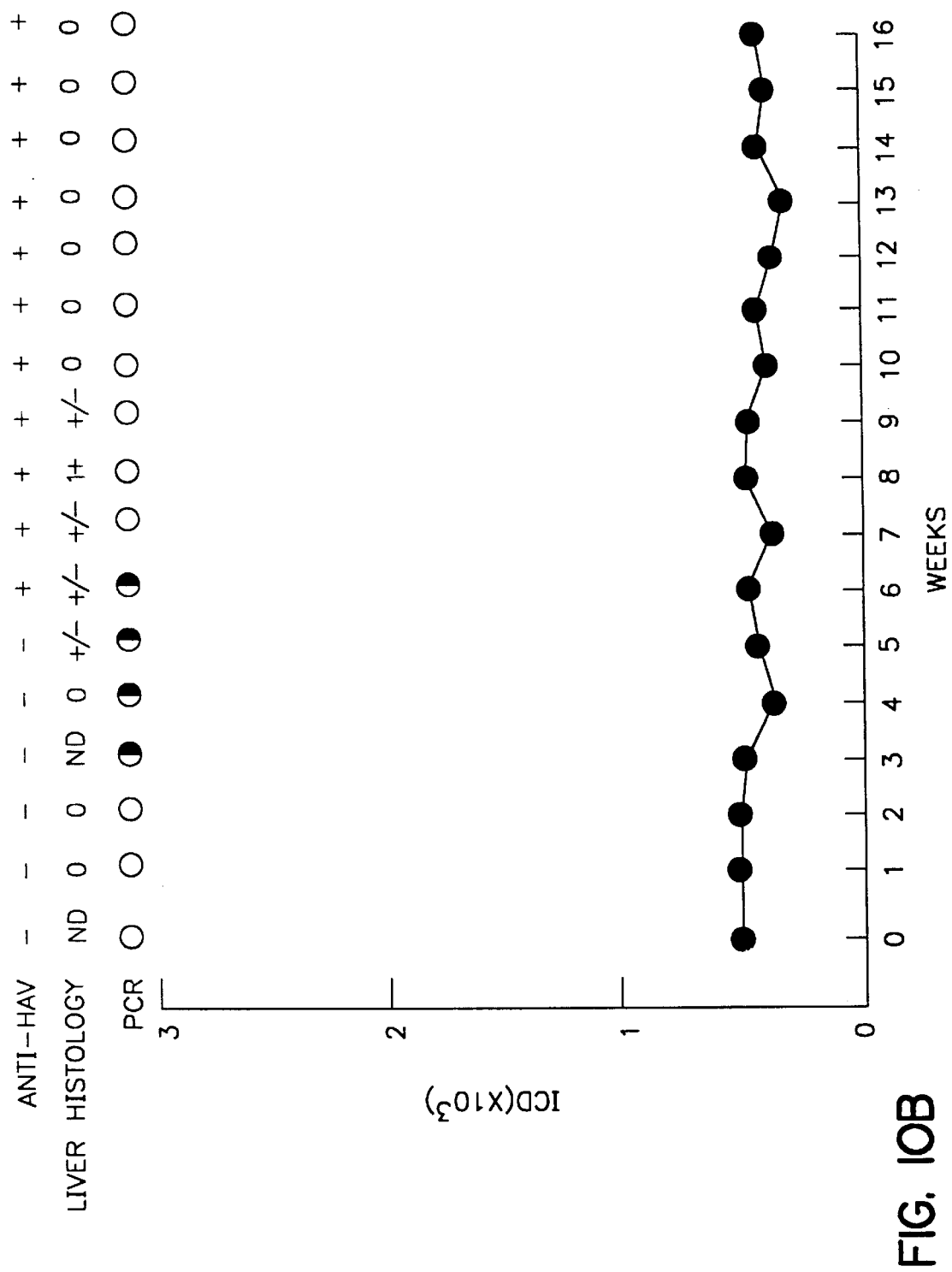
Figure 11A:
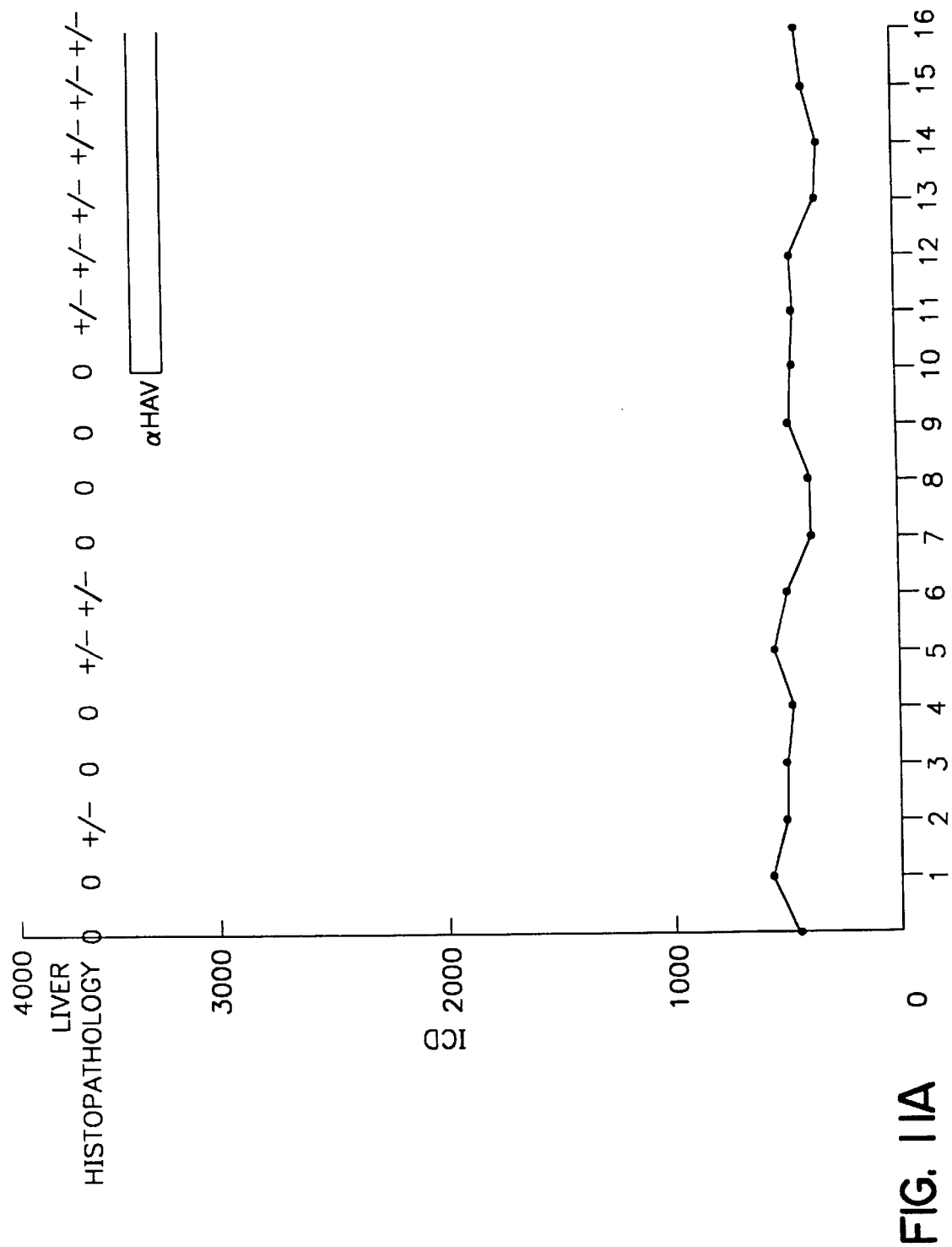
Figure 11B:
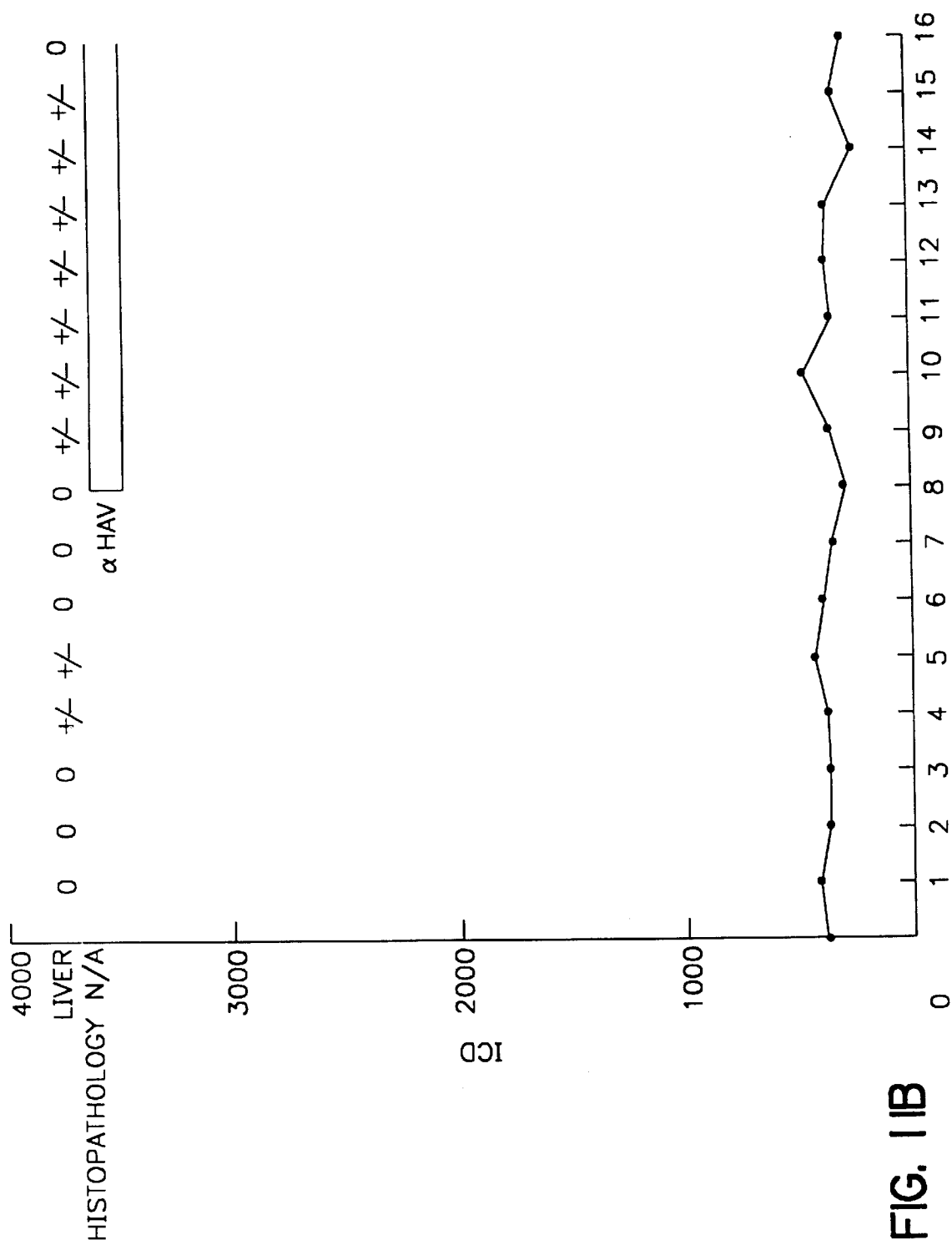
Figure 1I:
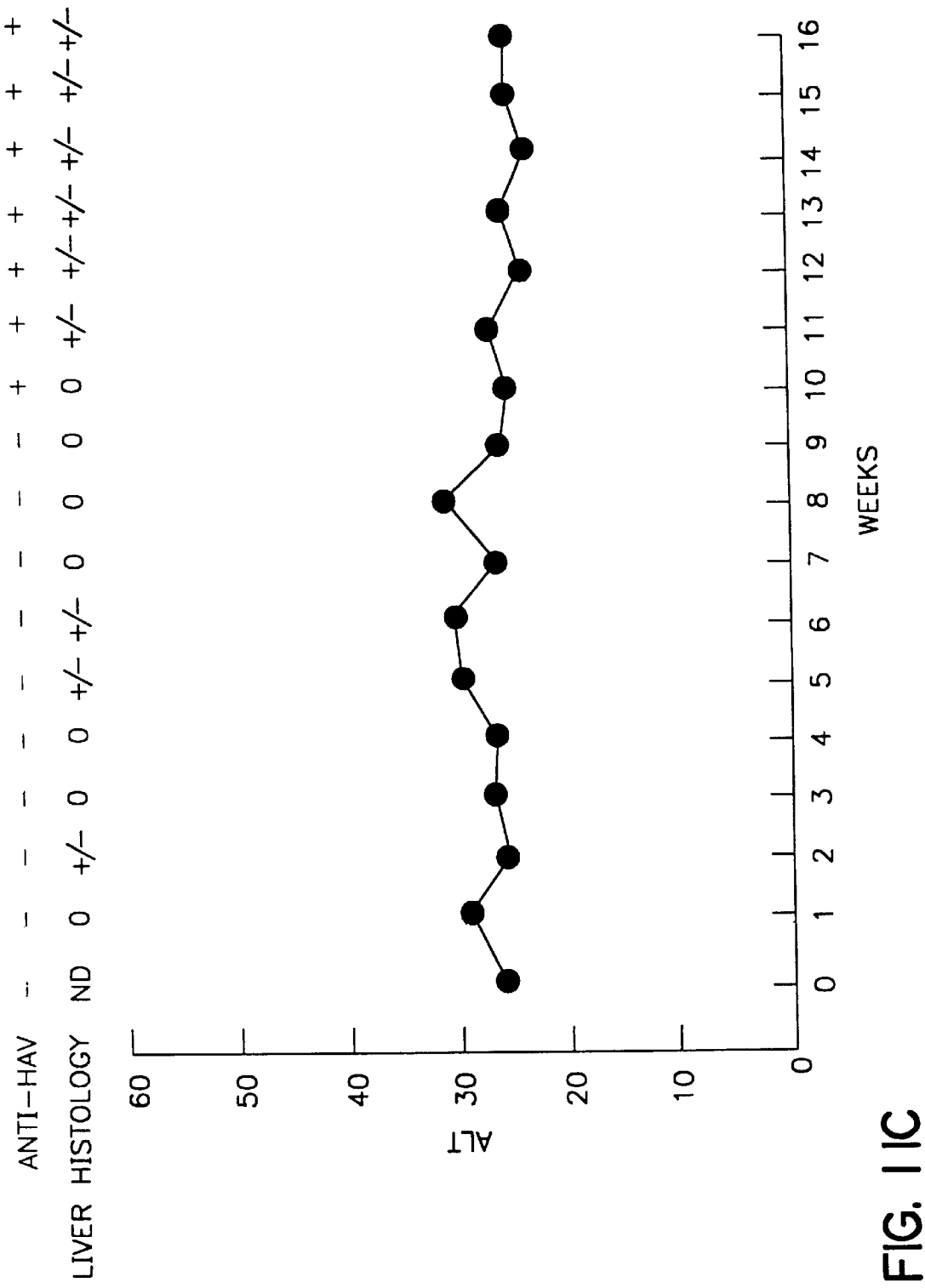
Figure 1D:
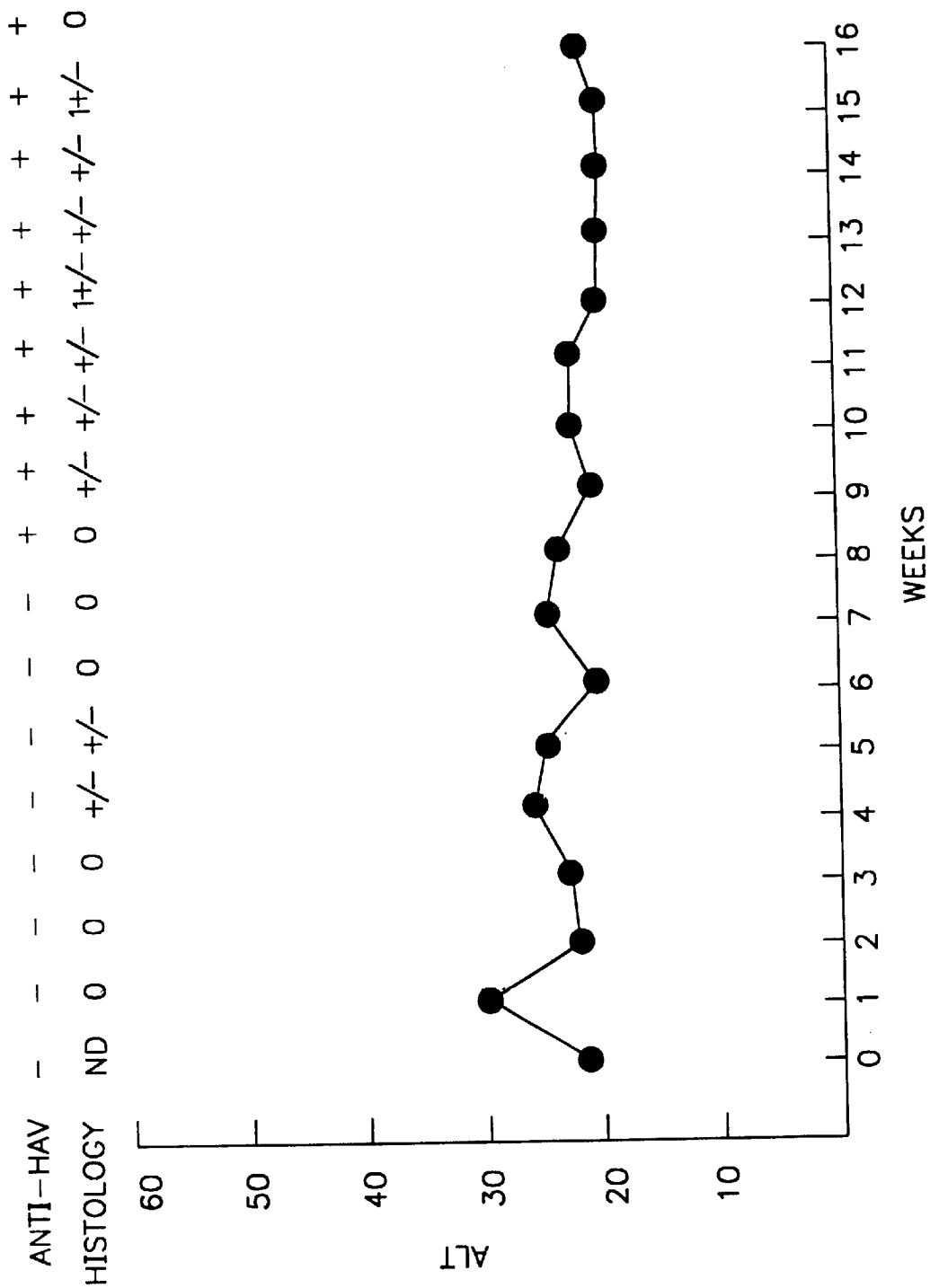

Tamarins inoculated with a chimera containing AGM-27 sequence in the 3' half of the 2C gene in the HAV/7 background (GR4) seroconverted at 6 weeks after inoculation (FIGS. 10A and 10B). The serum liver enzyme level was slightly elevated in one animal (FIG. 10A) and showed no significant increase in the second animal (FIG. 10B).

The data from these tamarin studies suggest that the 2C gene plays a critical role in virulence of HAV in tamarins and that the AGM-27 sequence at the 3' half of the 2C gene appears to make a greater contribution to this phenotype than the AGM-27 sequence at the 5' half of the 2C gene.

Example 6

Virulence of the GR2 and GR4 Chimeras in Chimpanzees

Figure 12A:
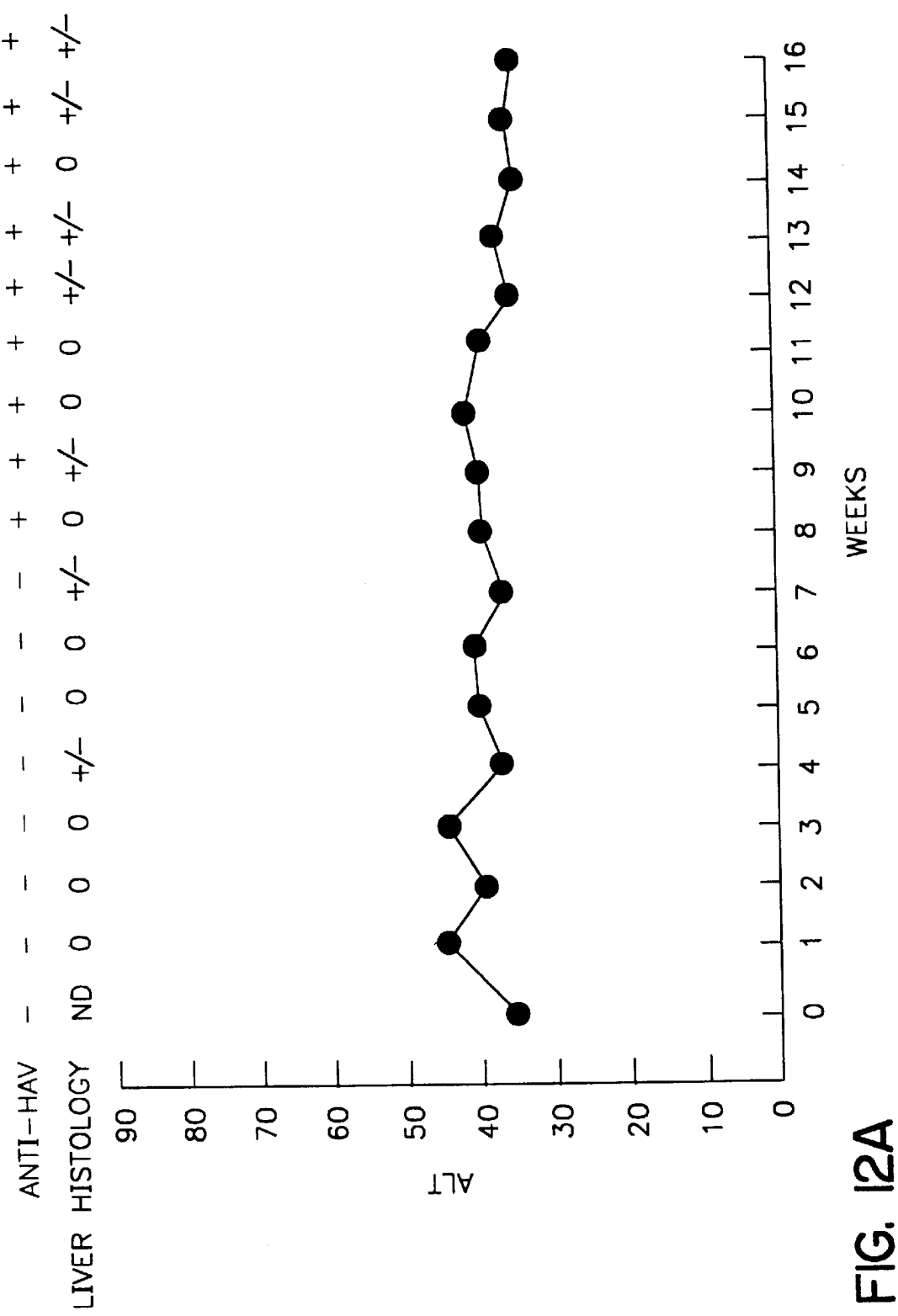
FIGS. 12A and 12B show biochemical (ALT levels), serological (anti-HAV) and histopathological analyses of two chimpanzees 1545 (FIG. 12A) and 1547 (FIG. 12B) inoculated with the GR2 chimera. A + in the row marked "anti-HAV" indicates samples that were positive for anti-HAV antibodies as determined by commercial assay. The histopathology scores correspond to mild hepatitis (1+), mild to moderate hepatitis (2+), moderately severe hepatitis (3+) and severe hepatitis (4+). The "ND" designation signifies that liver histology analysis was not performed for these samples.
Figure 12B:
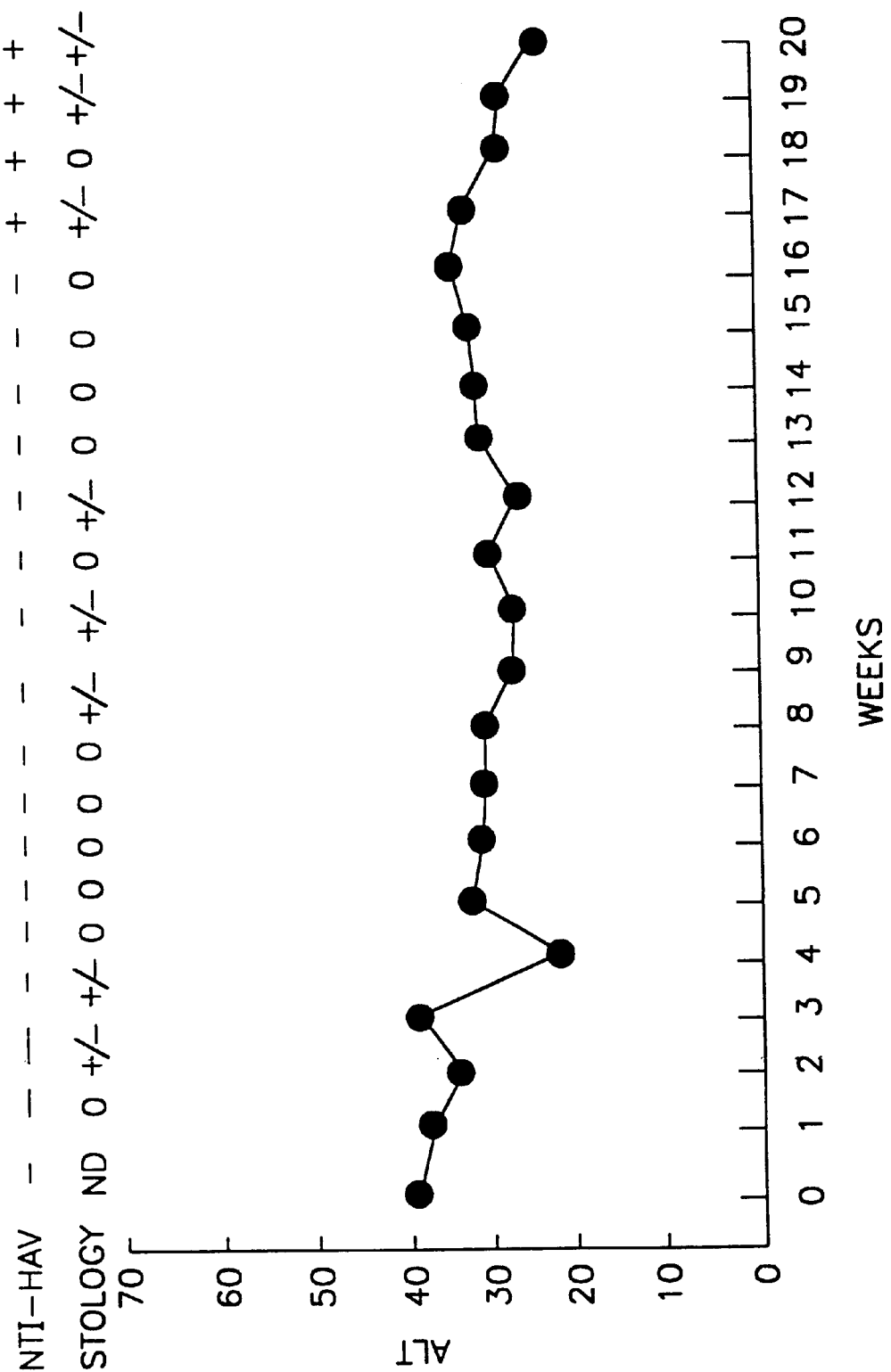

Chimpanzees inoculated with the GR4 chimera seroconverted either 8 or 15 weeks after inoculation (FIGS. 11A–11D) and chimpanzees inoculated with the GR2 chimera seroconverted either 7 or 17 weeks after inoculation (FIGS. 12A and 12B). None of the animals had any increase in serum liver enzyme levels (FIGS. 11A–11D, 12A and 12B).

Example 7

Summary of The Data From the Tamarins and Chimpanzees Inoculated With the HAV/7/AGM-27 Chimeras The data from the tamarin and chimpanzee studies are summarized in Table 1.

TABLE 1

| Tamarin | Virus | Seroconversion (week) | Peak ICD (week) | Peak ICD value | Anti-Hav titer |
|---------|-------|----------------------|-----------------|----------------|----------------|
| 782 | GR2 | 5 | 6 | 5190(1)* | 1:16000 |
| 783 | GR2 | 5 | 6 | 7520(2)* | 1:32000 |
| 808 | GR3 | 7 | none | baseline | 1:200 |
| 790 | GR3 | 15 | none | baseline | 1:1600 |

TABLE 1-continued

| | | | | | |
|---|---|---|---|---|---|
| 799 | GR4 | 6 | 7 | 1236(2)* | 1:8000 |
| 818 | GR4 | 6 | none | baseline | 1:1600 |

| Chimpanzee | Virus | Seroconversion (week) | Peak ALT (week) | Peak ALT value | Peak Anti-Hav titer |
|---|---|---|---|---|---|
| 1545 | GR2 | 8 | none | baseline | 1:200 |
| 1547 | GR2 | 17 | none | baseline | 1:40 |
| 1558 | GR4 | 10 | none | baseline | 1:800 |
| 1564 | GR4 | 8 | none | baseline | 1:40 |

*The number within the brackets refers to the number of weeks that the serum ICD level was above the baseline value.

The GR2 and GR4 chimeras thus appear to be attenuated in both tamarins and chimpanzees. These results suggest that the GR2 and GR4 chimeras may function as live attenuated vaccines to offer protection against challenge with human virulent HAV.

Example 8
Challenge of Chimpanzees Inoculated With AGM-27/HAV/7 Chimera

Chimpanzees are inoculated with $10^5$ tissue culture infectious dose equivalents of GR4 virus either by the oral, intramuscular, intradermal or intravenous route of infection. Blood samples are collected and needle liver biopsies are performed weekly on each animal for at least two weeks before inoculation and for the duration of the study. The blood samples are analyzed for seroconversion to anti-HAV by a commercial assay (Abbott Laboratories, North Chicago Ill.) and for serum alanine amino transferase (ALT) and isocitrate dehydrogenase (ICD) levels with standard techniques. Liver tissue will also be examined for signs of hepatitis. Three months after antibodies are first detected in serum using a commercial assay, the animals are challenged with $10^3$ to $10^4$ chimpanzee dose equivalents of virulent HAV (HM-175 or SD-11). After challenge with the virulent strain of HAV, the animals are protected as measured by biochemical (ALT or ICD), serological (levels of anti-HAV antibodies) and histopathological analyses of the animals for several months after challenge.

What is claimed is:

1. A DNA construct comprising a whole human attenuated hepatitis A virus (HAV) genome sequence wherein at least one fragment of the 2C gene of the human attenuated genome sequence is replaced by the corresponding fragment (s) of the 2C gene of a simian hepatitis A virus AGM-27 genome sequence, wherein the AGM-27 2C gene fragment does not comprise the entire 2C gene and encodes an amino acid sequence which differs in at least one amino acid residue from the amino acid sequence encoded by the corresponding fragment of the 2C gene of the human attenuated hepatitis A virus.

2. The DNA construct of claim 1, wherein the amino acid sequence encoded by the AGM-27 2C gene fragment differs in at least five amino residues from the amino acid sequence encoded by the corresponding fragment of the 2C gene of the human attenuated hepatitis A virus.

3. The DNA construct of claim 1, wherein one fragment of the 2C gene of the human attenuated hepatitis A virus genome sequence is replaced.

4. The DNA construct of claim 3, wherein the AGM-27 2C gene fragment encodes amino acid residues of the 2C protein selected from the group consisting of amino acid residues 48–328, 63–328, 84–328, 98–328, 1–49, 1–64, 1–86, 1–99, 1–283, 1–294, 1–304, 1–120 and 303–328, 1–70, 74–120, 74–328, 120–328, 1–121 and 1–328 of the 2C protein.

5. The DNA construct of claim 4, wherein the AGM-27 2C gene fragment encodes amino acids 120–328 of the 2C protein.

6. The DNA construct of claim 4, wherein the AGM-27 2C gene fragment encodes amino acids 1–121 of the 2C protein.

7. The DNA construct of claim 4, wherein the AGM-27 2C gene fragment encodes amino acids 1–328 of the 2C protein.

8. The DNA construct of claim 1, wherein two fragments of the 2C gene of the human attenuated HAV genome sequence are replaced.

9. The DNA construct of claim 8, wherein the two fragments encode amino acid residues of the 2C protein selected from the group of fragments consisting of amino acid residues 1–49 and 121–328, 1–64 and 121–328, 1–86 and 121–328, 1–99 and 121–328, 1–120 and 283–328, and 1–120 and 294–328 of the 2C protein.

10. An RNA transcript of the DNA construct of claim 1.

11. A cell transfected with the DNA construct of claim 1.

12. A cell transfected with the RNA transcript of claim 10.

13. A hepatitis A virus having a genome comprising a human attenuated hepatitis A virus genome in which at least one fragment of the 2C gene of the attenuated hepatitis A virus genome has been replaced by a corresponding fragment of a 2C gene from a simian AGM-27 hepatitis A virus genome sequence, wherein the AGM-27 2C gene fragment does not comprise the entire 2C gene and encodes an amino acid sequence which differs in at least one amino acid residue from the amino acid sequence encoded by the corresponding fragment of the 2C gene of the human attenuated HAV.

14. The hepatitis A virus of claim 13, wherein the amino acid sequence encoded by the AGM-27 2C gene fragment differs in at least five amino residues from the amino acid sequence encoded by the corresponding fragment of the 2C gene of the human attenuated HAV.

15. The hepatitis A virus of claim 13, wherein one fragment of the 2C gene of the human attenuated HAV is replaced.

16. The hepatitis A virus of claim 15, wherein the AGM-27 2C gene fragment encodes amino acid residues of the 2C protein selected from the group consisting of amino acid residues 48–328, 63–328, 84–328, 98–328, 1–49, 1–64, 1–86, 1–99, 1–283, 1–294, 1–304, 1–120 and 303–328, 1–70, 74–120, 74–328, 120–328, 1–121 and 1–328 of the 2C protein.

17. The hepatitis A virus of claim 16, wherein the AGM-27 2C gene fragment encodes amino acids 120–328 of the 2C protein.

18. The hepatitis A virus of claim 16, wherein the AGM-27 2C gene fragment encodes amino acids 1–121 of the 2C protein.

19. The hepatitis A virus of claim 16, wherein the AGM-27 2C gene fragment encodes amino acids 1–328 of the 2C protein.

20. The hepatitis A virus of claim 13, wherein two fragments of the 2C gene of the human attenuated HAV are replaced.

21. The hepatitis A virus of claim 20, wherein the two fragments encode amino acid residues of the 2C protein selected from the group consisting of amino acid residues 1–49 and 121–328, 1–64 and 121–328, 1–86 and 121–328, 1–99 and 121–328, 1–120 and 283–328, and 1–120 and 294–328 of the 2C protein.

22. A vaccine for preventing hepatitis A in a mammal, said vaccine comprising the DNA construct of claim 1 and a pharmaceutically acceptable carrier.

23. A vaccine for preventing hepatitis A in a mammal, said vaccine comprising the RNA transcript of claim 10 and a pharmaceutically acceptable carrier.

24. A vaccine for preventing hepatitis A in a mammal, said vaccine comprising the hepatitis A virus of claim 13 and a pharmaceutically acceptable carrier.

25. A method for preventing hepatitis A virus in a mammal, said method comprising administering to said mammal the DNA construct of claim 1 in an amount effective to stimulate the production of protective antibodies in said mammal.

26. A method of preventing hepatitis A virus in a mammal, said method comprising administering to said mammal the RNA transcript of claim 10 in an amount effective to stimulate the production of protective antibodies in said mammal.

27. A method of preventing hepatitis A virus in a mammal, said method comprising administering to said mammal the hepatitis A virus of claim 13 in an amount effective to stimulate the production of protective antibodies in said mammal.

28. A pharmaceutical composition comprising the DNA construct of claim 1.

29. A pharmaceutical composition comprising the RNA transcript of claim 10.

30. A kit for the prevention of hepatitis A in a mammal, said kit comprising the DNA construct of claim 1.

31. A kit for the prevention of hepatitis A in a mammal, said kit comprising the RNA transcript of claim 10.

32. A kit for the prevention of hepatitis A in a mammal, said kit comprising the hepatitis A virus of claim 13.

33. A host cell containing the hepatitis A virus of claim 13.

* * * * *

SEQUENCE LISTING (1) GENERAL INFORMATION:

(iii) NUMBER OF SEQUENCES: 3

(2) INFORMATION FOR SEQ ID NO: 1

(i) SEQUENCE CHARACTERISTICS:
      (A) LENGTH: 7493 base pairs
      (B) TYPE: nucleic acid
      (C) STRANDEDNESS: single
      (D) TOPOLOGY: linear (xi) SEQUENCE DESCRIPTION: SEQ ID NO: 1:

```
TTCAAGAGGG GTCTCCGGGA ATTTCCGGAG TCCCTCTTGG                40

AAGTCCATGG TGAGGGACT TGATACCTCA CCGCCGTTTG                 80

CCTAGGCTAT AGGCTAAATT TTCCCTTTCC CTTTTCCCTT               120

TCCTATTCCC TTTGTTTTGC TTGTAAATAT TAATTCCTGC               160

AGGTTCAGGG TTCTTAAATC TGTTTCTCTA TAAGAACACT               200

CATTTTTCAC GCTTTCTGTC TTCTTTCTTC CAGGGCTCTC               240

CCCTTGCCCT AGGCTCTGGC CGTTGCGCCC GGCGGGGTCA               280

ACTCCATGAT TAGCATGGAG CTGTAGGAGT CTAAATTGGG               320

GACACAGATG TTTGGAACGT CACCTTGCAG TGTTAACTTG               360

GCTTTCATGA ATCTCTTTGA TCTTCCACAA GGGGTAGGCT               400

ACGGGTGAAA CCTCTTAGGC TAATACTTCT ATGAAGAGAT               440

GCCTTGGATA GGGTAACAGC GGCGGATATT GGTGAGTTGT               480

TAAGACAAAA ACCATTCAAC GCCGGAGGAC TGACTCTCAT               520

CCAGTGGATG CATTGAGTGG ATTGACTGTC AGGGCTGTCT               560

TTAGGCTTAA TTCCAGACCT CTCTGTGCTT AGGGCAAACA               600

TCATTTGGCC TTAAATGGGA TTCTGTGAGA GGGGATCCCT               640

CCATTGACAG CTGGACTGTT CTTTGGGGCC TTATGTGGTG               680
```

| | |
|---|---|
| TTTGCCTCTG AGGTACTCAG GGGCATTTAG GTTTTTCCTC | 720 |
| ATTCTTAAAT AATAATGAAC ATGTCTAGAC AAGGTATTTT | 760 |
| CCAGACTGTT GGGAGTGGTC TTGACCACAT CCTGTCTTTG | 800 |
| GCAGACATTG AGGAAGAGCA AATGATTCAA TCAGTTGATA | 840 |
| GGACTGCAGT GACTGGTGCT TCTTATTTTA CTTCTGTGGA | 880 |
| TCAATCTTCA GTTCATACAG CTGAGGTTGG ATCACACCAG | 920 |
| GTTGAACCTT TGAGAACCTC TGTTGATAAA CCCGGTTCAA | 960 |
| AGAAGACTCA GGGAGAGAAA TTTTTCTTGA TTCATTCTGC | 1000 |
| AGATTGGCTT ACTACACATG CTCTTTTCCA TGAAGTTGCA | 1040 |
| AAATTGGATG TGGTGAAATT ATTATACAAT GAGCAGTTTG | 1080 |
| CTGTTCAAGG GTTGTTGAGA TACCATACAT ATGCAAGATT | 1120 |
| TGGCATTGAA ATTCAAGTTC AGATAAACCC TACACCTTTC | 1160 |
| CAACAGGGGG GATTGATCTG TGCTATGGTT CCTGGTGACC | 1200 |
| AGAGCTATGG TTCTATAGCA TCATTGACTG TTTATCCTCA | 1240 |
| TGGTTTGTTA AATTGCAATA TTAACAATGT GGTTAGAATA | 1280 |
| AAGGTTCCAT TTATTTACAC AAGAGGTGCT TACCACTTTA | 1320 |
| AAGATCCACA ATACCCAGTT TGGGAATTGA CAATTAGAGT | 1360 |
| TTGGTCAGAA TTAAATATTG GACAGGAAC TTCAGCTTAT | 1400 |
| ACTTCACTCA ATGTTTTAGC TAGATTTACA GATTTGGAGT | 1440 |
| TGCATGGATT AACTCCTCTT TCTACACAAA TGATGAGAAA | 1480 |
| TGAATTTAGG GTCAGTACTA CTGAGAATGT GGTGAATCTG | 1520 |
| TCAAATTATG AAGATGCAAG AGCAAAGATG TCTTTTGCTT | 1560 |
| TGGATCAGGA AGATTGGAAA TCTGATCCGT CCCAGGGTGG | 1600 |
| TGGGATCAAA ATTACTCATT TTACTACTTG GACATCTATT | 1640 |
| CCAACTTTGG CTGCTCAGTT TCCATTTAAT GCTTCAGACT | 1680 |
| CAGTTGGTCA ACAAATTAAA GTTATTCCAG TTGACCCATA | 1720 |
| TTTTTTCCAA ATGACAAATA CGAATCCTGA CCAAAAATGT | 1760 |
| ATAACTGCTT TGGCTTCTAT TTGTCAGATG TTTTGTTTTT | 1800 |
| GGAGAGGAGA TCTTGTCTTT GATTTTCAAG TTTTTCCCAC | 1840 |
| CAAATATCAT TCAGGTAGAT TACTGTTTTG TTTTGTTCCT | 1880 |
| GGCAATGAGC TAATAGATGT TTCTGGAATC ACATTAAAGC | 1920 |
| AAGCAACTAC TGCTCCTTGT GCAGTAATGG ATATTACAGG | 1960 |
| AGTGCAGTCA ACTTTGAGAT TCGTGTTCC CTGGATTTCT | 2000 |
| GACACTCCTT ACAGAGTGAA CAGGTATACA AAGTCAGCAC | 2040 |
| ATCAGAAAGG TGAGTACACT GCCATTGGGA AGCTTATTGT | 2080 |
| GTATTGTTAT AACAGATTGA CCTCTCCTTC TAACGTTGCT | 2120 |
| TCCCATGTCA GAGTGAATGT TTATCTTTCA GCAATTAACT | 2160 |
| TGGAATGTTT TGCTCCTCTT TATCATGCTA TGGATGTTAC | 2200 |
| TACACAAGTT GGAGATGATT CTGGAGGTTT TTCAACAACA | 2240 |

```
GTTTCTACAG AACAGAATGT TCCAGATCCC CAAGTTGGTA        2280

TAACAACCAT GAAAGATTTG AAAGGAAAAG CTAACAGAGG        2320

GAAAATGGAT GTTTCAGGAG TACAAGCACC TGTGGGAGCT        2360

ATCACAACAA TTGAGGATCC AGTTTTAGCA AAGAAAGTAC        2400

CTGAGACATT TCCTGAATTG AAACCTGGAG AATCCAGACA        2440

TACATCAGAT CATATGTCCA TCTACAAGTT TATGGGAAGG        2480

TCTCATTTCT TGTGCACTTT TACATTCAAT TCAAATAATA        2520

AAGAGTACAC ATTTCCTATA ACCTTGTCTT CAACCTCTAA        2560

TCCTCCTCAT GGTTTGCCAT CAACACTGAG GTGGTTTTTC        2600

AACTTGTTTC AGTTGTATAG AGGGCCTTTA GATCTGACAA        2640

TTATTATTAC AGGAGCAACT GATGTAGATG GCATGGCCTG        2680

GTTCACTCCA GTAGGTCTTG CCGTTGATAC TCCTTGGGTA        2720

GAGAAGGAGT CAGCTTTGTC TATTGACTAC AAAACTGCTC        2760

TTGGAGCTGT CAGATTTAAC ACAAGGAGAA CAGGGAACAT        2800

TCAGATTAGA TTACCATGGT ATTCTTATTT ATATGCTGTG        2840

TCTGGAGCAC TGGATGGTTT GGGTGACAAG ACAGATTCTA        2880

CATTTGGATT GGTTTCTATT CAGATTGCAA ATTACAATCA        2920

TTCTGATGAA TACTTGTCTT TTAGTTGTTA TTTGTCTGTC        2960

ACAGAACAAT CAGAGTTTTA TTTTCCCAGA GCTCCATTGA        3000

ACTCAAATGC CATGTTATCC ACTGAATCAA TGATGAGCAG        3040

AATTGCAGCT GGAGACTTGG AGTCATCAGT GGATGATCCT        3080

AGATCAGAGG AAGATAAAAG ATTTGAGAGT CATATAGAAT        3120

GCAGGAAGCC ATATAAAGAA CTGAGATTAG AAGTTGGGAA        3160

ACAAAGACTC AAGTATGCTC AGGAAGAATT GTCAAATGAA        3200

GTACTTCCAC CCCCTAGGAA AATGAAGGGA CTGTTTTCAC        3240

AAGCCAAAAT TTCTCTTTTT TATACTGAGG AGCATGAAAT        3280

AATGAAGTTT TCCTGGAGAG GTGTGACTGC TGATACTAGA        3320

GCTTTAAGGA GGTTTGGATT CTCTTTGGCC GCAGGCAGAA        3360

GTGTGTGGAC TCTTGAAATG GATGCTGGGG TTCTTACTGG        3400

GAGACTGATT AGATTGAATG ATGAGAAATG GACAGAAATG        3440

AAGGATGACA AGATTGTTTC ATTGATTGAA AAGTTTACAA        3480

GTAACAAATA TTGGTCCAAA GTGAATTTCC CACATGGGAT        3520

GTTGGATCTT GAAGAAATTG CTGCCAATTC TAAGGATTTT        3560

CCTAACATGT CTGAAACGGA TTTGTGTTTC TTGCTGCATT        3600

GGTTAAATCC AAAGAAAATT AATTTAGCAG ATAGAATGCT        3640

TGGATTGTCT GGAGTTCAGG AAATTAAAGA ACAAGGTGTT        3680

GGATTAATAG CAGAGTGTAG AACTTTCTTA GATTCTATTG        3720

CTGGAACTTT AAAATCTATG ATGTTTGGAT TTCATCATTC        3760

TGTGACTGTT GAAATTATAA ACACTGTGCT CTGTTTTGTT        3800

AAGAGTGGAA TTTTGCTTTA TGTAATACAA CAATTGAATC        3840
```

| | |
|---|---|
| AGGATGAACA TTCTCACATA ATTGGTTTGT TGAGAGTCAT | 3880 |
| GAATTATGCA GATATTGGTT GTTCAGTTAT TTCATGTGGC | 3920 |
| AAAGTTTTTT CCAAAATGCT GGAAACAGTC TTTAATTGGC | 3960 |
| AAATGGACTC CAGAATGATG GAGTTAAGGA CTCAGAGTTT | 4000 |
| TTCCAACTGG TTAAGAGATA TTTGTTCTGG GATCACCATT | 4040 |
| TTTAAAAACT TCAAGGATGC AATTTATTGG CTTTATACAA | 4080 |
| AATTAAAGGA CTTTTATGAA GTGAATTATG GCAAGAAGAA | 4120 |
| GGACATTTTA ATATTCTTA AAGATAACCA ACAAAAAATA | 4160 |
| GAGAAAGCCA TTGAGGAAGC CGATGAATTT TGCATTTTGC | 4200 |
| AAATCCAAGA TGTGGAAAAA TTTGAACAGT ATCAGAAAGG | 4240 |
| GGTTGACTTG ATACAAAAAT TGAGAACTGT TCATTCAATG | 4280 |
| GCTCAGGTTG ATCCAAATTT AATGGTTCAT TTGTCACCTT | 4320 |
| TGAGAGATTG TATAGCAAGA GTTCATCAGA AACTTAAAAA | 4360 |
| CCTTGGATCT ATAAATCAGG CAATGGTAAC GAGATGTGAG | 4400 |
| CCAGTTGTTT GTTATTTATA TGGCAAAAGA GGGGGAGGAA | 4440 |
| AGAGCTTAAC ATCAATTGCA TTGGCAACCA AAATTTGTAA | 4480 |
| ACATTATGGT GTTGAGCCTG AAAAGAATAT CTATACTAAA | 4520 |
| CCTGTGGCTT CAGATTACTG GGATGGATAT AGTGGACAAT | 4560 |
| TAGTTTGCAT CATTGATGAT ATTGGCCAAA ACACAACAGA | 4600 |
| TGAGGATTGG TCAGATTTTT GTCAGTTAGT GTCAGGATGT | 4640 |
| CCAATGAGAT TAAACATGGC CTCTCTTGAG GAGAAGGGTA | 4680 |
| GGCATTTTTC TTCTCCTTTT ATAATAGCAA CTTCAAATTG | 4720 |
| GTCAAATCCA AGTCCAAAAA CAGTTTATGT TAAGGAAGCA | 4760 |
| ATTGACCGCA GACTCCATTT CAAGGTTGAA GTTAAACCTG | 4800 |
| CTTCATTTTT CAAAAATCCT CACAATGATA TGTTGAATGT | 4840 |
| TAATTTAGCT AAAACAAATG ATGCAATCAA AGATATGTCT | 4880 |
| TGTGTTGATT TGATAATGGA TGGACATAAT GTTTCATTGA | 4920 |
| TGGATTTGCT CAGTTCTTTA GTCATGACAG TTGAAATTAG | 4960 |
| AAAACAAAAC ATGACTGAAT TCATGGAGTT GTGGTCTCAG | 5000 |
| GGAATTTCAG ATGATGATAA TGATAGTGCA GTAGCTGAGT | 5040 |
| TTTTCCAGTC TTTTCCATCT GGTGAACCAT CGAACTCTAA | 5080 |
| ATTATCTGGC TTTTTCCAAT CTGTTACTAA TCACAAGTGG | 5120 |
| GTTGCTGTGG GAGCTGCAGT TGGCATTCTT GGAGTGCTCG | 5160 |
| TTGGAGGATG GTTTGTGTAT AAGCATTTCT CCCGCAAAGA | 5200 |
| GGAGGAACCA ATCCCAGCTG AAGGGGTATA TCATGGTGTA | 5240 |
| ACTAAGCCCA AGCAAGTGAT TAAATTAGAT GCAGATCCAG | 5280 |
| TAGAATCTCA GTCAACTTTG GAAATAGCAG GACTGGTTAG | 5320 |
| GAAGAACTTG GTTCAGTTTG GAGTTGGAGA GAAGAATGGA | 5360 |
| TGTGTGAGAT GGGTTATGAA TGCCTTGGGA GTGAAAGATG | 5400 |

-continued

| | |
|---|---|
| ATTGGCTGCT TGTGCCTTCC CATGCTTATA AATTTGAGAA | 5440 |
| AGATTATGAA ATGATGGAGT TTTATTTTAA TAGAGGTGGA | 5480 |
| ACTTACTATT CAATTTCAGC TGGTAATGTT GTTATTCAAT | 5520 |
| CTTTGGATGT GGGATTCCAG GATGTTGTTC TGATGAAGGT | 5560 |
| TCCTACAATT CCTAAGTTTA GAGATATTAC TCAGCATTTT | 5600 |
| ATTAAGAAAG GGGATGTGCC TAGAGCTTTG AATCGCCTGG | 5640 |
| CAACATTAGT GACAACTGTA AATGGAACCC CTATGTTAAT | 5680 |
| TTCTGAGGGC CCACTAAAGA TGGAAGAGAA AGCTACTTAT | 5720 |
| GTTCATAAGA AAAATGATGG TACAACAGTT GATTTAACTG | 5760 |
| TGGATCAGGC ATGGAGAGGA AAAGGCGAAG GTCTTCCTGG | 5800 |
| AATGTGTGGT GGGGCCTTGG TTTCATCGAA TCAATCTATA | 5840 |
| CAGAATGCAA TCTTGGGCAT CCATGTTGCT GGAGGAAATT | 5880 |
| CAATTCTTGT TGCAAAATTG GTTACTCAAG AAATGTTCCA | 5920 |
| AAATATTGAT AAGAAAATTG AAAGTCAGAG AATTATGAAA | 5960 |
| GTGGAGTTTA CTCAGTGTTC AATGAATGTG GTCTCCAAAA | 6000 |
| CGCTTTTTAG AAAGAGTCCC ATTTATCATC ACATTGATAA | 6040 |
| AACCATGATT AATTTTCCTG CAGCTATGCC CTTTTCTAAA | 6080 |
| GCTGAAATTG ATCCAATGGC TGTGATGTTA TCTAAGTATT | 6120 |
| CATTACCTAT TGTAGAAGAA CCAGAGGATT ATAAAGAGGC | 6160 |
| TTCAATTTTT TATCAAAATA AAATAGTGGG TAAGACTCAG | 6200 |
| TTAGTTGATG ATTTTTTAGA TCTTGATATG CCATTACAG | 6240 |
| GGGCCCCAGG AATTGATGCT ATCAACATGG ATTCATCTCC | 6280 |
| TGGATTTCCT TATGTCCAGG AGAAGTTGAC CAAAAGAGAT | 6320 |
| TTAATTTGGT TGGATGAAAA TGGTTTATTG CTGGGAGTTC | 6360 |
| ATCCAAGATT GGCTCAGAGA ATCTTATTCA ATACTGTCAT | 6400 |
| GATGGAAAAT TGTTCTGATT TGGATGTTGT TTTTACAACC | 6440 |
| TGTCCAAAAG ATGAATTGAG ACCATTAGAG AAAGTGTTGG | 6480 |
| AATCAAAAAC AAGAGCTATT GATGCTTGTC CTCTGGATTA | 6520 |
| CTCAATTTTG TGCCGAATGT ATTGGGGTCC AGCTATTAGT | 6560 |
| TATTTTCATT TGAATCCAGG TTTCCATACA GGTGTTGCTA | 6600 |
| TTGGCATAGA TCCTGATAGA CAGTGGGATG AATTATTTAA | 6640 |
| AACAATGATA AGATTCGGAG ATGTTGGTCT TGATTTAGAT | 6680 |
| TTCTCTGCTT TTGATGCTAG TCTTAGTCCA TTTATGATTA | 6720 |
| GAGAAGCAGG TAGAATCATG AGTGAACTAT CTGGAACTCC | 6760 |
| ATCCCATTTT GGCACAGCTC TTATCAATAC TATCATTTAT | 6800 |
| TCCAAGCATT TGCTGTATAA CTGTTGTTAC CATGTCTGTG | 6840 |
| GTTCAATGCC CTCTGGGTCT CCTTGTACAG CTTTGCTAAA | 6880 |
| TTCAATTATT AATAATGTCA ATTTGTATTA TGTGTTTTCC | 6920 |
| AAGATATTTG GAAAGTCTCC AGTTTTCTTT TGTCAGGCTT | 6960 |
| TGAAGATTCT CTGTTATGGA GATGATGTTT TAATAGTTTT | 7000 |

```
CTCTCGAGAT GTTCAGATTG ATAATCTTGA TTTGATTGGA          7040

CAAAAAATTG TAGATGAGTT TAAGAAACTT GGCATGACAG          7080

CTACTTCTGC TGACAAGAAT GTACCTCAGC TGAAACCAGT          7120

TTCGGAATTA ACTTTTCTCA AAAGATCTTT CAATTTGGTA          7160

GAGGATAGAA TTAGACCTGC AATTTCGGAA AAAACAATTT          7200

GGTCTTTAAT AGCATGGCAG AGAAGTAACG CTGAGTTTGA          7240

GCAGAATTTA GAAAATGCTC AGTGGTTTGC TTTTATGCAT          7280

GGCTATGAGT TTTATCAGAA ATTTTATTAT TTTGTTCAGT          7320

CCTGTTTGGA GAAAGAGATG ATAGAATACA GACTTAAATC          7360

TTATGATTGG TGGAGAATGA GATTTTATGA CCAGTGTTTC          7400

ATTTGTGACC TTTCATGATT TGTTTAAACA AATTTTCTTA          7440

AAATTTCTGA GGTTTGTTTA TTTCTTTTAT CAGTAAATAA          7480

AAAAAAAAAA AAA                                       7493
```

(2) INFORMATION FOR SEQ ID NO: 2

(i) SEQUENCE CHARACTERISTICS:
        (A) LENGTH: 2227 amino acids
        (B) TYPE: amino acid
        (C) STRANDEDNESS: unknown
        (D) TOPOLOGY: unknown (xi) SEQUENCE DESCRIPTION: SEQ ID NO: 2:

```
Met Asn Met Ser Arg Gln Gly Ile Phe Gln Thr Val
 1               5                  10

Gly Ser Gly Leu Asp His Ile Leu Ser Leu Ala Asp
            15                  20

Ile Glu Glu Glu Gln Met Ile Gln Ser Val Asp Arg
 25                  30                  35

Thr Ala Val Thr Gly Ala Ser Tyr Phe Thr Ser Val
            40                  45

Asp Gln Ser Ser Val His Thr Ala Glu Val Gly Ser
 50                  55                  60

His Gln Val Glu Pro Leu Arg Thr Ser Val Asp Lys
                 65                  70

Pro Gly Ser Lys Lys Thr Gln Gly Glu Lys Phe Phe
            75                  80

Leu Ile His Ser Ala Asp Trp Leu Thr Thr His Ala
 85                  90                  95

Leu Phe His Glu Val Ala Lys Leu Asp Val Val Lys
                 100                 105

Leu Leu Tyr Asn Glu Gln Phe Ala Val Gln Gly Leu
      110                 115                 120

Leu Arg Tyr His Thr Tyr Ala Arg Phe Gly Ile Glu
                 125                 130

Ile Gln Val Gln Ile Asn Pro Thr Pro Phe Gln Gln
            135                 140

Gly Gly Leu Ile Cys Ala Met Val Pro Gly Asp Gln
145                 150                 155

Ser Tyr Gly Ser Ile Ala Ser Leu Thr Val Tyr Pro
                 160                 165
```

```
His Gly Leu Leu Asn Cys Asn Ile Asn Asn Val Val
    170                 175                 180

Arg Ile Lys Val Pro Phe Ile Tyr Thr Arg Gly Ala
            185                 190

Tyr His Phe Lys Asp Pro Gln Tyr Pro Val Trp Glu
            195                 200

Leu Thr Ile Arg Val Trp Ser Glu Leu Asn Ile Gly
205                 210                 215

Thr Gly Thr Ser Ala Tyr Thr Ser Leu Asn Val Leu
            220                 225

Ala Arg Phe Thr Asp Leu Glu Leu His Gly Leu Thr
            230                 235                 240

Pro Leu Ser Thr Gln Met Met Arg Asn Glu Phe Arg
                245                 250

Val Ser Thr Thr Glu Asn Val Val Asn Leu Ser Asn
            255                 260

Tyr Glu Asp Ala Arg Ala Lys Met Ser Phe Ala Leu
265                 270                 275

Asp Gln Glu Asp Trp Lys Ser Asp Pro Ser Gln Gly
            280                 285

Gly Gly Ile Lys Ile Thr His Phe Thr Thr Trp Thr
    290                 295                 300

Ser Ile Pro Thr Leu Ala Ala Gln Phe Pro Phe Asn
                305                 310

Ala Ser Asp Ser Val Gly Gln Gln Ile Lys Val Ile
            315                 320

Pro Val Asp Pro Tyr Phe Phe Gln Met Thr Asn Thr
325                 330                 335

Asn Pro Asp Gln Lys Cys Ile Thr Ala Leu Ala Ser
            340                 345

Ile Cys Gln Met Phe Cys Phe Trp Arg Gly Asp Leu
    350                 355                 360

Val Phe Asp Phe Gln Val Phe Pro Thr Lys Tyr His
            365                 370

Ser Gly Arg Leu Leu Phe Cys Phe Val Pro Gly Asn
            375                 380

Glu Leu Ile Asp Val Ser Gly Ile Thr Leu Lys Gln
385                 390                 395

Ala Thr Thr Ala Pro Cys Ala Val Met Asp Ile Thr
            400                 405

Gly Val Gln Ser Thr Leu Arg Phe Arg Val Pro Trp
    410                 415                 420

Ile Ser Asp Thr Pro Tyr Arg Val Asn Arg Tyr Thr
            425                 430

Lys Ser Ala His Gln Lys Gly Glu Tyr Thr Ala Ile
            435                 440

Gly Lys Leu Ile Val Tyr Cys Tyr Asn Arg Leu Thr
445                 450                 455

Ser Pro Ser Asn Val Ala Ser His Val Arg Val Asn
            460                 465

Val Tyr Leu Ser Ala Ile Asn Leu Glu Cys Phe Ala
    470                 475                 480
```

-continued

```
Pro Leu Tyr His Ala Met Asp Val Thr Thr Gln Val
             485                 490
Gly Asp Asp Ser Gly Gly Phe Ser Thr Thr Val Ser
         495             500
Thr Glu Gln Asn Val Pro Asp Pro Gln Val Gly Ile
505                 510                 515
Thr Thr Met Lys Asp Leu Lys Gly Lys Ala Asn Arg
             520                 525
Gly Lys Met Asp Val Ser Gly Val Gln Ala Pro Val
         530             535                 540
Gly Ala Ile Thr Thr Ile Glu Asp Pro Val Leu Ala
             545                 550
Lys Lys Val Pro Glu Thr Phe Pro Glu Leu Lys Pro
         555                 560
Gly Glu Ser Arg His Thr Ser Asp His Met Ser Ile
565                 570                 575
Tyr Lys Phe Met Gly Arg Ser His Phe Leu Cys Thr
             580                 585
Phe Thr Phe Asn Ser Asn Asn Lys Glu Tyr Thr Phe
590                 595                 600
Pro Ile Thr Leu Ser Ser Thr Ser Asn Pro Pro His
             605                 610
Gly Leu Pro Ser Thr Leu Arg Trp Phe Phe Asn Leu
             615                 620
Phe Gln Leu Tyr Arg Gly Pro Leu Asp Leu Thr Ile
625                 630                 635
Ile Ile Thr Gly Ala Thr Asp Val Asp Gly Met Ala
             640                 645
Trp Phe Thr Pro Val Gly Leu Ala Val Asp Thr Pro
         650             655                 660
Trp Val Glu Lys Glu Ser Ala Leu Ser Ile Asp Tyr
             665                 670
Lys Thr Ala Leu Gly Ala Val Arg Phe Asn Thr Arg
             675                 680
Arg Thr Gly Asn Ile Gln Ile Arg Leu Pro Trp Tyr
685                 690                 695
Ser Tyr Leu Tyr Ala Val Ser Gly Ala Leu Asp Gly
             700                 705
Leu Gly Asp Lys Thr Asp Ser Thr Phe Gly Leu Val
         710             715                 720
Ser Ile Gln Ile Ala Asn Tyr Asn His Ser Asp Glu
             725                 730
Tyr Leu Ser Phe Ser Cys Tyr Leu Ser Val Thr Glu
             735                 740
Gln Ser Glu Phe Tyr Phe Pro Arg Ala Pro Leu Asn
745                 750                 755
Ser Asn Ala Met Leu Ser Thr Glu Ser Met Met Ser
             760                 765
Arg Ile Ala Ala Gly Asp Leu Glu Ser Ser Val Asp
         770             775                 780
Asp Pro Arg Ser Glu Glu Asp Lys Arg Phe Glu Ser
             785                 790
His Ile Glu Cys Arg Lys Pro Tyr Lys Glu Leu Arg
```

```
                795                     800
Leu Glu Val Gly Lys Gln Arg Leu Lys Tyr Ala Gln
805                     810                     815

Glu Glu Leu Ser Asn Glu Val Leu Pro Pro Arg
        820                     825

Lys Met Lys Gly Leu Phe Ser Gln Ala Lys Ile Ser
    830                     835                     840

Leu Phe Tyr Thr Glu Glu His Glu Ile Met Lys Phe
                845                     850

Ser Trp Arg Gly Val Thr Ala Asp Thr Arg Ala Leu
        855                     860

Arg Arg Phe Gly Phe Ser Leu Ala Ala Gly Arg Ser
865                     870                     875

Val Trp Thr Leu Glu Met Asp Ala Gly Val Leu Thr
                880                     885

Gly Arg Leu Ile Arg Leu Asn Asp Glu Lys Trp Thr
890                     895                     900

Glu Met Lys Asp Asp Lys Ile Val Ser Leu Ile Glu
                905                     910

Lys Phe Thr Ser Asn Lys Tyr Trp Ser Lys Val Asn
            915                     920

Phe Pro His Gly Met Leu Asp Leu Glu Glu Ile Ala
925                     930                     935

Ala Asn Ser Lys Asp Phe Pro Asn Met Ser Glu Thr
            940                     945

Asp Leu Cys Phe Leu Leu His Trp Leu Asn Pro Lys
950                     955                     960

Lys Ile Asn Leu Ala Asp Arg Met Leu Gly Leu Ser
                965                     970

Gly Val Gln Glu Ile Lys Glu Gln Gly Val Gly Leu
            975                     980

Ile Ala Glu Cys Arg Thr Phe Leu Asp Ser Ile Ala
985                     990                     995

Gly Thr Leu Lys Ser Met Met Phe Gly Phe His His
            1000                    1005

Ser Val Thr Val Glu Ile Ile Asn Thr Val Leu Cys
        1010                    1015                    1020

Phe Val Lys Ser Gly Ile Leu Leu Tyr Val Ile Gln
                1025                    1030

Gln Leu Asn Gln Asp Glu His Ser His Ile Ile Gly
            1035                    1040

Leu Leu Arg Val Met Asn Tyr Ala Asp Ile Gly Cys
1045                    1050                    1055

Ser Val Ile Ser Cys Gly Lys Val Phe Ser Lys Met
            1060                    1065

Leu Glu Thr Val Phe Asn Trp Gln Met Asp Ser Arg
    1070                    1075                    1080

Met Met Glu Leu Arg Thr Gln Ser Phe Ser Asn Trp
                1085                    1090

Leu Arg Asp Ile Cys Ser Gly Ile Thr Ile Phe Lys
            1095                    1100

Asn Phe Lys Asp Ala Ile Tyr Trp Leu Tyr Thr Lys
1105                    1110                    1115
```

-continued

```
Leu Lys Asp Phe Tyr Glu Val Asn Tyr Gly Lys Lys
        1120                1125

Lys Asp Ile Leu Asn Ile Leu Lys Asp Asn Gln Gln
        1130                1135            1140

Lys Ile Glu Lys Ala Ile Glu Glu Ala Asp Glu Phe
        1145                1150

Cys Ile Leu Gln Ile Gln Asp Val Glu Lys Phe Glu
        1155                1160

Gln Tyr Gln Lys Gly Val Asp Leu Ile Gln Lys Leu
1165                1170                1175

Arg Thr Val His Ser Met Ala Gln Val Asp Pro Asn
        1180                1185

Leu Met Val His Leu Ser Pro Leu Arg Asp Cys Ile
        1190                1195                1200

Ala Arg Val His Gln Lys Leu Lys Asn Leu Gly Ser
        1205                1210

Ile Asn Gln Ala Met Val Thr Arg Cys Glu Pro Val
        1215                1220

Val Cys Tyr Leu Tyr Gly Lys Arg Gly Gly Gly Lys
1225                1230                1235

Ser Leu Thr Ser Ile Ala Leu Ala Thr Lys Ile Cys
        1240                1245

Lys His Tyr Gly Val Glu Pro Glu Lys Asn Ile Tyr
        1250                1255                1260

Thr Lys Pro Val Ala Ser Asp Tyr Trp Asp Gly Tyr
        1265                1270

Ser Gly Gln Leu Val Cys Ile Ile Asp Asp Ile Gly
        1275                1280

Gln Asn Thr Thr Asp Glu Asp Trp Ser Asp Phe Cys
1285                1290                1295

Gln Leu Val Ser Gly Cys Pro Met Arg Leu Asn Met
        1300                1305

Ala Ser Leu Glu Glu Lys Gly Arg His Phe Ser Ser
        1310                1315                1320

Pro Phe Ile Ile Ala Thr Ser Asn Trp Ser Asn Pro
        1325                1330

Ser Pro Lys Thr Val Tyr Val Lys Glu Ala Ile Asp
        1335                1340

Arg Arg Leu His Phe Lys Val Glu Val Lys Pro Ala
1345                1350                1355

Ser Phe Phe Lys Asn Pro His Asn Asp Met Leu Asn
        1360                1365

Val Asn Leu Ala Lys Thr Asn Asp Ala Ile Lys Asp
        1370                1375                1380

Met Ser Cys Val Asp Leu Ile Met Asp Gly His Asn
        1385                1390

Val Ser Leu Met Asp Leu Leu Ser Ser Leu Val Met
        1395                1400

Thr Val Glu Ile Arg Lys Gln Asn Met Thr Glu Phe
1405                1410                1415

Met Glu Leu Trp Ser Gln Gly Ile Ser Asp Asp Asp
        1420                1425
```

-continued

```
Asn Asp Ser Ala Val Ala Glu Phe Phe Gln Ser Phe
        1430                1435                1440

Pro Ser Gly Glu Pro Ser Asn Ser Lys Leu Ser Gly
            1445                1450

Phe Phe Gln Ser Val Thr Asn His Lys Trp Val Ala
        1455                1460

Val Gly Ala Ala Val Gly Ile Leu Gly Val Leu Val
1465                1470                1475

Gly Gly Trp Phe Val Tyr Lys His Phe Ser Arg Lys
            1480                1485

Glu Glu Glu Pro Ile Pro Ala Glu Gly Val Tyr His
        1490                1495                1500

Gly Val Thr Lys Pro Lys Gln Val Ile Lys Leu Asp
                1505                1510

Ala Asp Pro Val Glu Ser Gln Ser Thr Leu Glu Ile
            1515                1520

Ala Gly Leu Val Arg Lys Asn Leu Val Gln Phe Gly
1525                1530                1535

Val Gly Glu Lys Asn Gly Cys Val Arg Trp Val Met
            1540                1545

Asn Ala Leu Gly Val Lys Asp Asp Trp Leu Leu Val
        1550                1555                1560

Pro Ser His Ala Tyr Lys Phe Glu Lys Asp Tyr Glu
            1565                1570

Met Met Glu Phe Tyr Phe Asn Arg Gly Gly Thr Tyr
            1575                1580

Tyr Ser Ile Ser Ala Gly Asn Val Val Ile Gln Ser
1585                1590                1595

Leu Asp Val Gly Phe Gln Asp Val Val Leu Met Lys
            1600                1605

Val Pro Thr Ile Pro Lys Phe Arg Asp Ile Thr Gln
        1610                1615                1620

His Phe Ile Lys Lys Gly Asp Val Pro Arg Ala Leu
            1625                1630

Asn Arg Leu Ala Thr Leu Val Thr Thr Val Asn Gly
            1635                1640

Thr Pro Met Leu Ile Ser Glu Gly Pro Leu Lys Met
1645                1650                1655

Glu Glu Lys Ala Thr Tyr Val His Lys Lys Asn Asp
            1660                1665

Gly Thr Thr Val Asp Leu Thr Val Asp Gln Ala Trp
        1670                1675                1680

Arg Gly Lys Gly Glu Gly Leu Pro Gly Met Cys Gly
            1685                1690

Gly Ala Leu Val Ser Ser Asn Gln Ser Ile Gln Asn
            1695                1700

Ala Ile Leu Gly Ile His Val Ala Gly Gly Asn Ser
1705                1710                1715

Ile Leu Val Ala Lys Leu Val Thr Gln Glu Met Phe
            1720                1725

Gln Asn Ile Asp Lys Lys Ile Glu Ser Gln Arg Ile
            1730                1735                1740

Met Lys Val Glu Phe Thr Gln Cys Ser Met Asn Val
```

-continued

```
                    1745                1750
Val Ser Lys Thr Leu Phe Arg Lys Ser Pro Ile Tyr
            1755                1760

His His Ile Asp Lys Thr Met Ile Asn Phe Pro Ala
1765                1770                1775

Ala Met Pro Phe Ser Lys Ala Glu Ile Asp Pro Met
            1780                1785

Ala Val Met Leu Ser Lys Tyr Ser Leu Pro Ile Val
    1790                1795                1800

Glu Glu Pro Glu Asp Tyr Lys Glu Ala Ser Ile Phe
                1805                1810

Tyr Gln Asn Lys Ile Val Gly Lys Thr Gln Leu Val
        1815                1820

Asp Asp Phe Leu Asp Leu Asp Met Ala Ile Thr Gly
1825                1830                1835

Ala Pro Gly Ile Asp Ala Ile Asn Met Asp Ser Ser
            1840                1845

Pro Gly Phe Pro Tyr Val Gln Glu Lys Leu Thr Lys
        1850                1855                1860

Arg Asp Leu Ile Trp Leu Asp Glu Asn Gly Leu Leu
                1865                1870

Leu Gly Val His Pro Arg Leu Ala Gln Arg Ile Leu
            1875                1880

Phe Asn Thr Val Met Met Glu Asn Cys Ser Asp Leu
1885                1890                1895

Asp Val Val Phe Thr Thr Cys Pro Lys Asp Glu Leu
                1900                1905

Arg Pro Leu Glu Lys Val Leu Glu Ser Lys Thr Arg
    1910                1915                1920

Ala Ile Asp Ala Cys Pro Leu Asp Tyr Ser Ile Leu
            1925                1930

Cys Arg Met Tyr Trp Gly Pro Ala Ile Ser Tyr Phe
        1935                1940

His Leu Asn Pro Gly Phe His Thr Gly Val Ala Ile
1945                1950                1955

Gly Ile Asp Pro Asp Arg Gln Trp Asp Glu Leu Phe
            1960                1965

Lys Thr Met Ile Arg Phe Gly Asp Val Gly Leu Asp
        1970                1975                1980

Leu Asp Phe Ser Ala Phe Asp Ala Ser Leu Ser Pro
                1985                1990

Phe Met Ile Arg Glu Ala Gly Arg Ile Met Ser Glu
            1995                2000

Leu Ser Gly Thr Pro Ser His Phe Gly Thr Ala Leu
2005                2010                2015

Ile Asn Thr Ile Ile Tyr Ser Lys His Leu Leu Tyr
        2020                2025

Asn Cys Cys Tyr His Val Cys Gly Ser Met Pro Ser
    2030                2035                2040

Gly Ser Pro Cys Thr Ala Leu Leu Asn Ser Ile Ile
                2045                2050

Asn Asn Val Asn Leu Tyr Tyr Val Phe Ser Lys Ile
        2055                2060
```

```
Phe Gly Lys Ser Pro Val Phe Phe Cys Gln Ala Leu
2065                2070                2075

Lys Ile Leu Cys Tyr Gly Asp Asp Val Leu Ile Val
        2080                2085

Phe Ser Arg Asp Val Gln Ile Asp Asn Leu Asp Leu
    2090                2095                2100

Ile Gly Gln Lys Ile Val Asp Glu Phe Lys Lys Leu
                2105                2110

Gly Met Thr Ala Thr Ser Ala Asp Lys Asn Val Pro
        2115                2120

Gln Leu Lys Pro Val Ser Glu Leu Thr Phe Leu Lys
2125                2130                2135

Arg Ser Phe Asn Leu Val Glu Asp Arg Ile Arg Pro
        2140                2145

Ala Ile Ser Glu Lys Thr Ile Trp Ser Leu Ile Ala
        2150                2155                2160

Trp Gln Arg Ser Asn Ala Glu Phe Glu Gln Asn Leu
                2165                2170

Glu Asn Ala Gln Trp Phe Ala Phe Met His Gly Tyr
        2175                2180

Glu Phe Tyr Gln Lys Phe Tyr Tyr Phe Val Gln Ser
2185                2190                2195

Cys Leu Glu Lys Glu Met Ile Glu Tyr Arg Leu Lys
                2200                2205

Ser Tyr Asp Trp Trp Arg Met Arg Phe Tyr Asp Gln
        2210                2215                2220

Cys Phe Ile Cys Asp Leu Ser
                2225

(2) INFORMATION FOR SEQ ID NO: 3

(i) SEQUENCE CHARACTERISTICS:
         (A) LENGTH: 7400 base pairs
         (B) TYPE: nucleic acid
         (C) STRANDEDNESS: single
         (D) TOPOLOGY: linear (xi) SEQUENCE DESCRIPTION: SEQ ID NO: 3:

CTTGATACCT CACCGCCGTT TGCCTAGGCT ATAGGCTTCT                40

TCCCTACACC CTTGTTTGTT TTTTTTTTTT TTTTTTGTGT                80

GTTTGTAAAT ATTAATTCCT GCAGGTTCAG GGTTCTTAAT               120

TTGTTCTGCT ATACAGACAC TCTTTTCACG CTTTCTGTCA               160

TCTTATTTCC TGGGCTCTCC CCTTGCCCAA GGCTCTGGCC               200

GTTGCGCCCG GCGGGGTCAA CTCCATGGTT AGCATGGAGC               240

TGTAGGAGTC TAAATTGGGG ACGCAGATGC TAGGAACGTC               280

GCCCTGCAGT GTTAACCTGG CTTTCATGAA GCTCTTTGAT               320

CTTCTACAAG AGGTAGGCTA CGGGTGAAAC CTCTTAGATT               360

AATACTCCTA TGGAGAGATA TCTTGAATAG GGTAACAGCG               400

GTGGATATTG GTGAGTTCCT TTGGGACAAA AACCATTCAA               440

CACCGGAGGA CTGACTCTCA TTCAGTAGTT GCATTGAGTG               480

AATTGTCTGT CAGGGCTGTC TTTGGGTTTA ATTCCTGGCC               520
```

| | |
|---|---|
| TCTCTGTGCT TAGGGCAAAC CATTTCCTGG CCTTAAATGG | 560 |
| AGTTCTGTGA GAGGGAACTC CTCCTTTATA TGCTGGACAT | 600 |
| ATTTTGGGGC CTTAGGGTTA TGGTTTGCCT CTGAGGTACT | 640 |
| CAGGGGCATT TAGGTTTTTC CTCATTTATA TGTTTATGAT | 680 |
| GATGAATATG TCTAAACAAG GTATTTTCCA GACTGTTGGG | 720 |
| AGTGGCCTTG ACCACATACT GTCTTTAGCA GATGTGGAGG | 760 |
| AAGAGCAAAT GATACAGTCA GTGGACAGGA CAGCTGTCAC | 800 |
| TGGTGCTTCT TATTTTACTT CTGTAGACCA ATCTTCAGTT | 840 |
| CATACGGCAG AAGTTGGTGC ACATCAGACA GAGCCTCTTA | 880 |
| AGACATCAGT AGATAAACCA GGTTCAAAGA AAACCCAAGG | 920 |
| AGAGAAATTT TTCCTAATAC ATTCTGCAGA TTGGTTAACA | 960 |
| ACACATGCTT TGTTTCATGA AGTCGCCAAA TTGGATGTTG | 1000 |
| TTAGTTTGTT GTACAATGAA CAATTTGCTG TACAGGGTTT | 1040 |
| GTTGAGATAC CATACTTATG CTAGATTTGG AATTGAAATT | 1080 |
| CAAGTCCAGA TTAATCCCAC TCCCTTTCAG CAGGGAGGTC | 1120 |
| TTATTTGTGC AATGGTTCCA GGAGACCAAG GTTATGGTTC | 1160 |
| CATAGCCTCA TTGACAGTTT ATCCACATGG TCTCTTGAAT | 1200 |
| TGCAACATTA ACAATGTTGT TAGAATCAAA GTTCCATTCA | 1240 |
| TTTATACTAG AGGTGCTTAT CATTTCAAAG ATCCACAGTA | 1280 |
| TCCAGTCTGG GAGTTAACTA TTCGTGTTTG GTCAGAATTA | 1320 |
| AATATAGGAA CTGGTACTTC TGCTTATACA TCATTGAATG | 1360 |
| TCTTGGCTAG ATTCACTGAT TTAGAGCTTC ATGGATTGAC | 1400 |
| ACCATTATCT CACAAATGA TGAGGAATGA ATTTAGAGTG | 1440 |
| AGTACAACTG AAAATGTGGT TAATTTGTCA AATTACGAGG | 1480 |
| ATGCTAGAGC AAAGATGTCT TTTGCACTTG ATCAGGAAGA | 1520 |
| TTGGAAAACA GATCCCTCGC AAGGAGGAGG AATCAAAATC | 1560 |
| ACTCATTTTA CAACATGGAC TTCAATTCCC ACGCTTGCTG | 1600 |
| CACAGTTTGC ATTTAATGCT TCTGCATCTG TGGGGCAGCA | 1640 |
| AATTAAGGTG ATCCCTGTTG ATCCTTATTT TTATCAGATG | 1680 |
| ACCAATTCAA ATCCAGACCA AAAGTGTATT ACTGCTTTAG | 1720 |
| CTTCTGTCTG TCAGATGTTC TGCTTTTGGA GGGGAGATCT | 1760 |
| TGTTTTTGAT TTTCAGGTTT TCCCCACAAA ATATCACTCT | 1800 |
| GGGAGGTTGT TATTTGTTT TGTGCCAGGG AATGAGTTGA | 1840 |
| TAGATGTTTC AGGTATAACC CTGAAGCAGG CAACTACTGC | 1880 |
| ACCCTGTGCT GTTATGGATA TAACAGGAGT TCAGTCAACA | 1920 |
| TTGAGATTTA GAGTGCCTTG GATCTCTGAT ACACCTTACA | 1960 |
| GAGTGAATAG ATACACAAAA TCAGCTCACC AGAAAGGAGA | 2000 |
| GTATACAGCT ATTGGGAAGT TGATTGTTTA TTGTTATAAT | 2040 |
| AGGCTTACCT CACCCTCAAA TGTTGCTTCC CATGTTAGGG | 2080 |

```
TTAATGTTTA TCTTTCTGCA ATAAATTTGG AATGTTTTGC          2120

ACCCCTATAT CATGCAATGG ATGTGACATC ACAGACAGGT          2160

GATGATTCAG GTGGGTTTTC AACTACAGTT TCTACAGAAC          2200

AGAATGCTCC TGATCCTCAA GTTGGAATTA CCACTATTAA          2240

GGATTTAAAA GGGAAGGCAA ATAGAGGAAA GATGGATGTT          2280

TCTGGCATTC AAGCACCAGT GGGTGCTATT ACAACCATTG          2320

AGGATCCAGT GTTAGCTAAA AAAGTTCCTG AGACTTTTCC          2360

AGAATTGAGA CCAGGTGAAT CTAGACATAC TTCAGATCAT          2400

ATGTCTATTT ACAAATTTAT GGGGAGGTCA CACTTTCTTT          2440

GTACATTTAC TTTCAATGCA AACAATAGGG AGTATACTTT          2480

TCCAATAACA CTGTCCTCTA CATCGAATCC ACCTCATGGT          2520

TTACCATCAA CACTGAGGTG GTTTTTCAAC CTTTTTCAAT          2560

TGTATAGAGG GCCATTGGAC TTGACTATTA TAATTACAGG          2600

TGCTACTGAT GTGGATGGCA TGGCTTGGTT TACTCCTGTG          2640

GGCCTAGCTG TGGATACTCC CTGGGTTGAA AAGCAATCAG          2680

CGTTGACTAT TGATTATAAA ACTGCTCTTG GGGCTATTAG          2720

GTTTAACACT AGGAGAACAG GAAATATTCA GATTAGACTT          2760

CCTTGGTATT CATACCTTTA TGCTGTTTCT GGCGCTTTGG          2800

ATGGACTTGG GGACACTACT GATTCGACTT TCGGGTTGGT          2840

CTCTATTCAG ATTGCCAATT ATAATCATTC AGATGAATAT          2880

CTGTCATTCA GTTGTTATCT TTCAGTTACT GAACAATCAG          2920

AATTTTATTT TCCAAGGGCT CCTCTCAATT CTAATGCTAT          2960

GATGGTTTCT GAGTCCATGC TAGATCGCAT TGCAAGTGGA          3000

GATTTAGAAT CATCAGTTGA TGACCCAAGA TCAGCAGAGG          3040

ACAAAAGGTT TGAAAGTCAT ATTGAGCAGG GCAAGCCATA          3080

CAAAGAATTA AGAATGGAAG TTGGGAAGCA GAGATTGAAA          3120

TATGCCATGG AGGAGTTATC AAATGAAATT TTACCACCTC          3160

CTCGGAAAGT GAAAGGACTG TTTTCTCAAG CTAAAATTTC          3200

TTTATTTTAT ACAGAAGACC ATGAAATTGT GAAGCTTTCA          3240

TGGAAAGGTC TCACAGCTGA TACAAGAGCT CTCAGGAGAT          3280

ATGGTTTTTC TCTTGCTGCT GGAAGAAGTG TGTGGACTCT          3320

TGAGATGGAA GCTGGAGTTC TGACTGGAAG GATGATCAGA          3360

TTGAATGATG AAAAGTGGAC TGAGATTAAG GATGATAAGA          3400

TAGTGGCTTT GGTAGAGAAA TTTACATCTA ATAAGAATTG          3440

GTCTAAAGTC AATTTTCCAC ATGGGATGCT AGATTTGGAA          3480

GAGATAGCAT CAAATTCAAA GGATTTTCCT AATATGTCTG          3520

AGACTGACTT GTGTTTTCTT TTACATTGGT TGAATCCTAA          3560

GAAGATAAAT CTAGCTGATA GAATGCTTGG ATTGTCTGGT          3600

GTTCAGGAAA TTAAGGAACA GGGTGTTGGC TTAATAGCTG          3640

AATGTAGAAC ATTTTTAGAT TCTATAGCTG GCACTTTGAA          3680
```

```
ATCAATGATG TTTGGGTTTC ATCAGTCTGT TACTGTGGAA                3720

ATAATTAATA CTGTCTTGTG TTTTGTTAAG AGTGGGATCC                3760

TTCTTTATGT TATTCAGCAA TTGAATCAAA ATGAACACTC                3800

TCATATTATA GGGCTTTTAC AGGTGATGAA TTATGCAGAC                3840

ATTGGTTGCT CTGTGATTTC TTGTGGAAAG ATATTCTCAA                3880

AAATGTTAGA AACAGTCTTT AATTGGCAGA TGGATTCTAG                3920

AATGATGGCT CTTAGAACAC AGAGTTTCTC TAATTGGTTG                3960

AGAGACATAT GTTCGGGGAT AACCATTTTC AAAAATTTTA                4000

AGGATGCTAT TTTCTGGCTG TACACTAAAT TAAAGGATTA                4040

TTATGATTCT AACTATGGGA AAAAGAAGGA TGTTCTGAAT                4080

GTTTTAAAAG AAAATCAGCA TAGGATTGAG AAAGCCATTG                4120

AAGAGGCTGA TCAGTTCTGT GTTTTGCAGA TTCAGGACGT                4160

TGAGAAGTCA GAGCAATATC AGAAGGGAGT TGAACTCATT                4200

CAGAAATTGA GAACAGTTCA TTCCCTGGCC CAGGTCGACT                4240

CTAGTTTGAT GTCTCATTTG TCACCACTGA GAGATTGTAT                4280

TGCTAGAGTC CATCAAAAAC TTAAGAATTT AGGCTCAATT                4320

AATCAGGCTA TGGTGACTAG GTGTGAACCT GTGGTCTGTT                4360

ATTTATATGG TAAGAGAGGT GGAGGAAAGA GTTTAACTTC                4400

TATTGCATTG GCAACAAAAA TTTGCAAACA TTATGGTGTT                4440

GAACCAGAAA AGAATATATA TACAAAACCT GTTGCTTCAG                4480

ACTACTGGGA TGGATATAGT GGTCAATTGG TTTGTATCAT                4520

TGATGACATT GGTCAAAATA CTACAGATGA AGATTGGTCA                4560

GATTTTGTC AATTGGTGTC TGGTTGTCCT ATGAGGTTAA                 4600

ATATGGCTTC TTTGGAAGAG AAAGGGAGAC ACTTTTCTTC                4640

CCCGTTTATA ATTGCCACAT CAAATTGGTC AAATCCAAGT                4680

CCTAAGACTG TTTATGTGAA GGAAGCTATA GATCGCCGCC                4720

TTCATTATAA GATTGAAGTC AAACCAGCAT CTTTTTACAA                4760

AAATGCACAC AATGATATGC TCAATGTGAA TCTTGCAAGA                4800

AATAATGATG CCATTAAAGA CATGTCCTGT GTAGATTTAC                4840

TGATGGATGG CCATACTGTG TCTTTATCTG AGCTTTTAAA                4880

TTCTCTTGTT ATGACAGTTG AAATTAGAAA ACAAAATATG                4920

TCAGAATTTA TGAAATTGTG GTCACAGGGT GTGTCAGATG                4960

ATGATAATGA CAGTGCAGTT GCTGAGTTCT TCCAGTCTTT                5000

TCCATCAGGA GAACCCTCAA ATTCTAAGTT ATCTAGTTTC                5040

TTCAAGGCGG TCACTAATCA TAAGTGGGTT GCTATTGGAG                5080

CTGCTGTTGG AGTTCTGGGT GTCTTAGTGG GAGGTTGGTT                5120

TGTGTACAAG CATTTTACCA AGAAGAACC AATACCAACT                 5160

GAAGGAGTGT ATCATGGAGT AACCAAACCT AAACAGGTTA                5200

TCAAATTGGA TGCTGATCCT GTTGACTCCC AATCTACTCT                5240
```

```
TGAGATAGCT GGACTAGTTA GGAAGAATTT GGTTCAATTT        5280

GGAGTTGGGG AGAAGAATGG ATGTGTTAGG TGGGTCATGA        5320

ATGCTTTAGG TATTAAAGAT GATTGGCTGC TGGTCCCCTC        5360

ACATGCATAC AAATTTGAGA AAGATTATCA AATGATGGAG        5400

TTTTATTTTA ATAGAGGAGG AACTTATTAT TCAATTTCTG        5440

CTGGTAATGT TGTAATCCAG TCTTTGGATG TTGGTTTTCA        5480

GGATGTTGTT TTGATGAAGG TTCCTACAAT TCCAAAGTTT        5520

AGAGATATAA CTGAGCATTT TATTAAGAAG AATGATGTTC        5560

CAAGAGCTTT GAATAGATTG GCTACACTTG TTACAACAGT        5600

TAATGGGACA CCAATGCTGA TTTCCGAAGG TCCACTTAAG        5640

ATGGAAGAAA AGGCCACTTA TGTCCATAAG AGAAATGACG        5680

GAACTACTGT TGATTTGACT GTTGATCAAG CTTGGAGGGG        5720

AAAAGGTGAG GGCCTCCCAG GTATGTGTGG TGGAGCTCTG        5760

ATTTCCTCAA ATCAGTCAAT ACAAAATGCC ATTCTTGGGA        5800

TTCATGTTGC AGGTGGCAAT TCTATTTTGG TTGCCAAACT        5840

TGTGACTCAG GAAATGTTCC AGAACATTGA ACAAAAAGCA        5880

ATAGAAAGTC AGAGGATAAT GAAAGTGGAA TTCACTCAGT        5920

GTTCAATGAA TGTGGTCTCC AAAACGCTTT TTAAAAAGAG        5960

TCCAATTCAT CATCACATTG ATAGGAACAT GATTAATTTT        6000

CCTGCTGTAA TGCCTTTTTC TAAAGCTGAG ATTGATCCTA        6040

TGGCTGTTAT GTTGTCTAAG TATTCTCTTC CTATTGTTGA        6080

AGAGCCAGAT GATTATAAGA TGGCTTCCAT TTATTTCCAA        6120

AATAAAGTAA TGGGGAAAAC TTTTCTTGTT GATGACTTTT        6160

TGGATATAGA TATGGCAATC ACAGGTGCTC CAGGAATAGA        6200

TGCTATTAAT ATGGATTCTT CACCAGGATT TCCTTATGTT        6240

CAGGAGAAGT TGACAAAGAA AGACTTGATC TGGTTGGATG        6280

AGAATGGGCT GCTGTTAGGA GTTCATCCAA GGCTTGCTCA        6320

AAGAATCTTG TACAACACAG TTATGATGGA GAATTGTTCT        6360

GATCTTGATG TGGTCTTTAC AACATGTCCC AAGGATGAAC        6400

TTAGGCCTCT GGACAAAGTA TTGGAATCAA AGACTAGAGC        6440

AATTGATGCT TGTCCATTGG ATTATACAAT TCTTTGTAGG        6480

ATTTATTGGG GTCCTGCTAT TAGTTACTTT CAATTGAATC        6520

CTGGATTTCA CACAGGAGTT GCTATTGGAA TTGATCCGGA        6560

TAGACATTGG GACGAGTTGT TTAAAACAAT GGTTAGATTT        6600

GGTGATGTAG GTTTAGACCT TGATTTTTCA TCATTTGATG        6640

CTAGTCTTAG TCCTTTTATG ATAAGAGAGG CAGGGAGAAT        6680

TTTGAGTGAA ATGTCAGGGA CACCCTCACA CTTTGGAGAG        6720

GCCTTGATTA ATACAATCAT TTATTCCAAG CATTTGTTGT        6760

ACAATTGTTG TTATCATGTT TATGGTTCCA TGCCATCAGG        6800

GTCCCCTTGT ACAGCACTTT TAAATTCAAT TGTAAACAAT        6840
```

-continued

```
GTTAATTTGT ACTATGTGTT TTCAAAAATT TTTAGGAAGT              6880

CTCCTGTTTT CTTTGGAGAT GCTCTGAAGA TTCTTTGTTA              6920

TGGAGATGAT GTCCTCATTG TTTTTTCCAG AAATGTCCAG              6960

ATTGATAATT TGGAATCTAT TGGACAGAAA ATTGTAGATG              7000

AGTTTGGAAA ATTAGGCATG ACTGCAACAT CAGCAGACAA              7040

GTCTGTTCCT AAGTTGAAAC CTATTTCTGA GCTCACTTTT              7080

CTTAAAAGAT CATTCAATCT TGTTGAAGAT CGGATTAGAC              7120

CTGCAATTTC AGAGAAAACA ATTTGGTCTC TCGTTGCTTG              7160

GCAGAGAAGC AATGCTGAAT TTGAACAGAA TTTGGAAAAT              7200

GCTCAATGGT TTGCTTTTAT GCATGGTTTT GAATTTTATC              7240

AGAAATTTTA CCATTTTGTT CAGTCCTGCC TGGAGAAAGA              7280

GATGGTAGAA TACAGATTGA AATCATATGA TTGGTGGAGA              7320

ATGAAGTTTT ATGATCAGTG CTTTGTTTGT GACCTCACAT              7360

GATTTGTTTA AACAAACCTT CTTAAAATTT CTGAGATTTG              7400
```